US009487476B2

(12) United States Patent
Jorgensen et al.

(10) Patent No.: US 9,487,476 B2
(45) Date of Patent: Nov. 8, 2016

(54) CATECHOL DIETHERS AS POTENT ANTI-HIV AGENTS

(71) Applicant: YALE UNIVERSITY, New Haven, CT (US)

(72) Inventors: William L. Jorgensen, Deep River, CT (US); Karen S. Anderson, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/348,952

(22) PCT Filed: Oct. 12, 2012

(86) PCT No.: PCT/US2012/059886
§ 371 (c)(1),
(2) Date: Apr. 1, 2014

(87) PCT Pub. No.: WO2013/056003
PCT Pub. Date: Apr. 18, 2013

(65) Prior Publication Data
US 2014/0288017 A1 Sep. 25, 2014

Related U.S. Application Data

(60) Provisional application No. 61/546,285, filed on Oct. 12, 2011.

(51) Int. Cl.
C07C 255/54 (2006.01)
A61K 31/4409 (2006.01)
A61K 45/06 (2006.01)
C07D 239/54 (2006.01)
A61K 31/513 (2006.01)
C07D 239/553 (2006.01)
A61K 31/5377 (2006.01)
A61K 31/277 (2006.01)
A61K 31/536 (2006.01)
A61K 31/505 (2006.01)
C07D 251/42 (2006.01)
A61K 31/53 (2006.01)
C07D 239/10 (2006.01)
C07D 405/12 (2006.01)
C07D 471/04 (2006.01)
A61K 31/4412 (2006.01)
A61K 31/5025 (2006.01)
C07D 213/57 (2006.01)
C07D 213/69 (2006.01)
C07D 487/04 (2006.01)

(52) U.S. Cl.
CPC .......... C07C 255/54 (2013.01); A61K 31/277 (2013.01); A61K 31/4409 (2013.01); A61K 31/4412 (2013.01); A61K 31/505 (2013.01); A61K 31/5025 (2013.01); A61K 31/513 (2013.01); A61K 31/53 (2013.01); A61K 31/536 (2013.01); A61K 31/5377 (2013.01); A61K 45/06 (2013.01); C07D 213/57 (2013.01); C07D 213/69 (2013.01); C07D 239/10 (2013.01); C07D 239/54 (2013.01); C07D 239/553 (2013.01); C07D 251/42 (2013.01); C07D 405/12 (2013.01); C07D 471/04 (2013.01); C07D 487/04 (2013.01)

(58) Field of Classification Search
CPC C07C 255/54; C07D 213/57; C07D 239/54; C07D 239/553; C07D 251/42; C07D 213/69; C07D 487/04; A61K 31/4409; A61K 45/06; A61K 31/513; A61K 31/5377; A61K 31/277; A61K 31/536; A61K 31/505; A61K 31/53; A61K 31/4412; A61K 31/5025
USPC .............. 514/27, 357, 274, 272, 235.8, 520, 514/230.5, 275, 245, 348, 248, 120; 544/314, 313, 123, 211, 236; 558/424; 546/330, 296
See application file for complete search history.

(56) References Cited

U.S. PATENT DOCUMENTS

| | | |
|---|---|---|
| 4,880,784 A | 11/1989 | Robins et al. |
| 5,179,084 A | 1/1993 | Saito et al. |
| 5,491,135 A | 2/1996 | Blough |
| 5,532,215 A | 7/1996 | Lezdey et al. |
| 5,821,242 A | 10/1998 | Colacino et al. |
| 5,891,874 A | 4/1999 | Colacino et al. |
| 6,114,327 A | 9/2000 | Dunlap et al. |
| 6,180,604 B1 | 1/2001 | Fraser et al. |
| 6,232,120 B1 | 5/2001 | Dropulic et al. |
| 6,316,492 B1 | 11/2001 | Young et al. |
| 6,316,505 B1 | 11/2001 | Kabanov et al. |
| 6,340,690 B1 | 1/2002 | Bachand et al. |
| 2008/0249151 A1* | 10/2008 | Sweeney .............. C07D 249/12 514/384 |
| 2010/0273785 A1* | 10/2010 | Ly ........................ C07D 211/96 514/227.5 |

FOREIGN PATENT DOCUMENTS

| | | |
|---|---|---|
| EP | 0538704 A1 | 4/1993 |
| JP | 4500939 BO | 4/1970 |
| JP | 48099182 AO | 12/1973 |
| WO | 2004096761 A1 | 11/2004 |

OTHER PUBLICATIONS

Bollini et al. Computationally-Guided Optimization of a Docking Hit to Yield Catechol Diethers as Potent Anti-HIV Agents. J. Med. Chem. 54:8582-8591, 2011.*

(Continued)

Primary Examiner — Clinton Brooks
Assistant Examiner — Yih-Horng Shiao
(74) Attorney, Agent, or Firm — Henry D. Coleman; R. Neil Sudol

(57) ABSTRACT

The present invention is directed to novel catechol diether compounds, pharmaceutical compositions therefrom and methods for inhibiting reverse transcriptase and treating HIV infections, especially included drug resistant strains of HIV 1 and 2 and/or secondary disease states and/or conditions which occur as a consequence of HIV infection.

39 Claims, 11 Drawing Sheets

(56) References Cited

OTHER PUBLICATIONS

Flexner, C. HIV drug development: the next 25 years. Nature Rev. Drug Disc. 2007, 6, 959-966.

De Clerq, E. The design of drugs for HIV and HCV. Nature Rev. Drug Disc. 2007, 6, 1001-1018.

Jochmans, D. Novel HIV-1 reverse transcriptase inhibitors. Virus Res. 2008, 134, 171-185.

Kohlstaedt L. A.; Wang J.; Friedman J. M.; Rice P.A.; Steitz T. A. Crystal Structure at 3.5 Å Resolution of HIV-1 Reverse Transcriptase Complexed with an Inhibitor. Science 1992, 256, 1783-1790.

Prajapati, D. G.; Ramajayam, R.; Yadav, M. R.; Giridhar, R. The search for potent, small molecule NNRTIs: A review. Bioorg. Med. Chem. 2009, 17, 5744-5762.

Adams, J.; Patel, N.; Mankaryous, N.; Tadros, M.; Miller, C. D. HIV/AIDS: Nonnucleoside Reverse Transcriptase Inhibitor Resistance and the Role of the Second-Generation Agents. Ann. Pharmacotherapy 2010, 44, 157-165.

Richman, D. D.; Margolis, D. M.; Delaney, M.; Greene, W. C.; Hazuda, D.; Pomerantz, R. J. The Challenge of Finding a Cure for HIV Infection. Science 2009, 323, 1304-1307.

Jorgensen, W. L. Efficient Drug Lead Discovery and Optimization. Acc. Chem. Res. 2009, 42, 724-733.

Zeevaart, J. G.; Wang, L.; Thakur, V. V.; Leung, C. S.; Tirado-Rives, J.; Bailey, C. M.; Domaoal, R. A.; Anderson, K. S.; Jorgensen, W. L. Optimization of Azoles as Anti-HIV Agents Guided by Free-Energy Calculations. J. Am. Chem. Soc. 2008, 130, 9492-9499.

Leung, C. S.; Zeevaart, J. G.; Domaoal, R. A.; Bollini, M.; Thakur, V. V.; Spasov, K.; Anderson, K. S.; Jorgensen, W. L. Eastern extension of azoles as non-nucleoside inhibitors of HIV-1 reverse transcriptase; cyano group alternatives. Bioorg. Med. Chem. Lett. 2010, 20, 2485-2488.

Nichols, S. E.; Domaoal, R. A.; Thakur, V. V.; Bailey, C. M.; Wang, L.; Tirado-Rives, J.; Anderson, K. S.; Jorgensen, W. L. Discovery of Wild-type and Y181C Mutant Non-nucleoside HIV-1 Reverse Transcriptase Inhibitors Using Virtual Screening with Multiple Protein Structures. J. Chem. Inf. Model. 2009, 49, 1272-1279.

Hopkins, A. L.; Ren, J.; Esnouf, R. M.; Willcox, B. E.; Jones, E. Y.; Ross, C.; Miyasaka, T.; walker, R. T.; Tanaka, H.; Stammers, D. K.; Stuart, D. I. Complexes of HIV-1 Reverse Transcriptase with Inhibitors of the HEPT Series Reveal Conformational Changes Relevant to the Design of Potent Non-Nucleoside Inhibitors. J. Med. Chem. 1996, 39, 1589-1600.

Ren, J.; Nichols, C.; Bird, L.; Chamberlain, P.; Weaver, K.; Short, S.; Stuart, D. I.; Stammers, D. K. Structural mechanisms of drug resistance for mutations at codons 181 and 188 in HIV-1 reverse transcriptase and the improved resilience of second generation non-nucleoside inhibitors. J. Mol. Biol. 2001, 312, 795-805.

Himmel, D. M.; Das, K.; Clark, A. D.; Hughes, S. H.; Benjahad, A.; Oumouch, S.; Guillemont, J.; Coupa, S.; Poncelet, A.; Csoka, I.; Meyer, C.; Andries, K.; Nguyen, C. H.; Grierson, D. S.; Arnold, E. Crystal structures for HIV-1 reverse transcriptase in complexes with three pyridinone derivatives: a new class of non-nucleoside inhibitors effective against a broad range of drug-resistant strains. J. Med. Chem. 2005, 48, 7582-7591.

Baba, M.; Tanaka, H.; Miyasaka, T.; Yuasa, S.; Ubasawa, M.; De Clercq, E. Hept derivatives: 6-Benzyl-1-ethoxymethyl-5-isopropyluracil (MKC-442). Nucleosides Nucleotides 1995, 14, 575-583.

Jorgensen, W. L. QikProp, v 3.0; Schrodinger LLC: New York, 2006.

McKay, A. F.; Baker, H. A.; Gaudry, R.; Garmaise, D. L.; Ranz R. J. Bacteriostats. VII. Substituted Benzylphenols. J. Med. Chem. 1963, 6, 816-817.

Novikov, M. S.; Ozerov, A. A. The Silyl Method for the Synthesis of 1[-2(Phenoxy)ethyl]uracils. Chem. Het. Comp. 2005, 41, 905-908.

20Frieden, M.; Giraud, M.; Reese, C. B.; Song, Q. Synthesis of 1-[cis-3-(hydroxymethyl)cyclobutyl]-uracil, -thymine and -cytosine. J. Chem. Soc. Perkin Trans. 1998, 1, 2827-2832.

Reese, C. B.: Stewart, J. C. M. Methoxyacetyl as a protecting group in ribonucleoside chemistry. Tetrahedron Lett. 1968, 40, 4273-4276.

Lin, T. S.; Luo, M. Z.; Liu, M. C.; Pai, S. B.; Dutschman,G. E.; Cheng, Y. C. Antiviral activity of 2',3'-dideoxy-α-L-5-fluorocytidine (α-L-EddC) and 2',3'-dideoxy-α-L-cytidine (α-L-ddC) against hepatitis B virus and human immunodeficiency virus type 1 in vitro. Biochem.,Pharmacol. 1994, 47, 171-174.

Ray, A. S.; Yang, Z.; Chu, C. K.; Anderson, K. S. Novel use of a guanosine prodrug approach to convert 2',3'- didehydro-2',3'-dideoxyguanosine into a viable antiviral agent. Antimicrob. Agents Chemother. 2002, 46, 887-891.

Jorgensen, W. L.; Tirado-Rives, J. Molecular Modeling of Organic and Biomolecular Systems Using BOSS and MCPRO. J. Comput. Chem. 2005, 26, 1689-1700.

Jorgensen, W. L.; Thomas, L. T. Perspective on Free-Energy Perturbation Calculations for Chemical Equilibria. J. Chem. Theory Comput. 2008, 4, 869-876.

Jorgensen, W. L.; Maxwell, D. S.; Tirado-Rives, J. Development and Testing of the OPLS All-Atom Force Field on Conformational Energetics and Properties of Organic Liquids. J. Am. Chem .Soc. 1996, 118, 11225-11236.

Jorgensen, W. L.; Tirado-Rives, J. Potential energy functions for atomic-level simulations of water, and organic and biomolecular systems. Proc. Natl. Acad. Sci. U.S.A: 2005, 102, 6665-6670.

Jorgensen, W. L.; Chandrasekhar, J.; Madura, J. D.; Impey, R. W.; Klein, M. L. Comparison of Simple Potential Functions for Simulating Liquid Water. J. Chem. Phys. 1983, 79, 926-935.

Tanaka, H.; Takashima, H.; Ubasawa, M.; Sekiya, K.; Inouye, N.; Baba, M.; Shigeta, S.; Walker, R. T.; De Clerq, E.; Miyasaka, T. Synthesis and Antiviral Activity of 6-Benzyl Analogs of 1-[(2-Hydroxyethoxy)methyl]-5-(phenylthio)thymine (HEPT) as Potent and Selective Anti-HIV-1 Agents. J. Med. Chem. 1995, 38, 2860-2865.

Benjahad, A.; Guillemont, J.; Andries, K.; Nguyen, C. H.; Grierson, D. S. Benjahad, A.; Guillemont, J.; Andries, K.; Nguyen, C. H.; Grierson, D. S. 3-Iodo-4-phenoxypyridinones (IOPY's), a new family of highly potent non-nucleoside inhibitors of HIV-1 reverse transcriptase. Bioorg. Med. Chem. Lett. 2003, 13, 4309-4312.

Brameld, K. A.; Kuhn, B.; Reuter, D. C.; Stahl, M. Small Molecule Conformational Preferences Derived from Crystal Structure Data. A Medicinal Chemistry Focused Analysis. J. Chem. Inf. Model. 2008, 48, 1-24.

Pierce, A. C.; Rao, G.; Bemis, G. W. Breed: Generating Novel Inhibitors through Hybridization of Known Ligands. Application to CDK2, P38, and HIV Protease. J. Med. Chem. 2004, 47, 2768-2775.

Jorgensen, W. L.; Bollini, M.; Thakur, V. V.; Domaoal, R. A.; Spasov, K.; Anderson, K. S., Efficient Discovery of Potent Anti-HIV Agents Targeting the Tyr181Cys Variant of HIV Reverse Transcriptase, J. Am. Chem. Soc. 2011, 133, 15686-15896.

Janssen, P. A. J.; Lewi, P. J.; Arnold, E.; Daeyaert, F.; de Jonge, M.; Heeres, J.; Koymans, L.; Vinkers, M.; Guillemont, J.; Pasquier, E.; Kukla, M.; Ludovici, D.; Andries, K.; de Bethune, M.-P.; Pauwels, R.; Das, K.; Clark, A. D., Jr.; Frenkel, Y. V.; Hughes, S. H.; Medaer, B.; De Knaep, F.; Bohets, H.; De Clerck, F.; Lampo, A.; Williams, P. & Stoffels, P. In search of a novel anti-HIV drug: multidisciplinary coordination in the discovery of 4-[[4[[4-[(1E)-2-cyanoethenyl]-2,6-dimethylphenyl]amino]-2-pyrimidinyl]amino]benzonitrile (R278474, rilpivirine). J. Med. Chem. 2005, 48, 1901-1919.

Das, K.; Bauman, J. D.; Clark, A. D., Jr.; Frenkel, Y. V.; Lewi, P. J.; Shatkin, A. J.; Hughes, S. H.; Arnold, E. High-resolution structures of HIV-1 reverse transcriptase/TMC278 complexes: Strategic flexibility explains potency against resistance mutations. Proc. Nat. Acad. Sci. USA 2008, 105, 1466-1471.

Politzer, P.; Murray, J. S.; Clark, T. Halogen bonding: an electrostatically-driven highly directional noncovalent interaction. Phys. Chem. Chem. Phys. 2010, 12, 7748-7757.

Ibrahim, M. A. A. Molecular Modeling Study of Halogen Bonding in Drug Discovery. J. Comput. Chem. 2011, 32, 2564-2574.

(56) References Cited

OTHER PUBLICATIONS

Hardegger, L. A.; Kuhn, B.; Spinnler, B.; Anselm, L.; Ecabert, R.; Stihle, M.; Gsell, B.; Thoma, R.; Diez, J.; Benz, J.; Plancher, J.-M.; Hartmann, G.; Banner, D. W.; Haap, W.; Diederich, F. Angew. Chem. Int. Ed. 2011, 50, 314-318.

Tucker, T. J.; Saggar, S.; Sisko, J. T.; Tynebor, R. M.; Williams, T. M.; Felock, P. J.; Flynn, J. A.; Lai, M.-T.; Liang, Y.; McGaughey, G.; Liu, M.; Miller, M.; Moyer, G.; Munshi, V.; Perlow-Poehnelt, R.; Prasad, S.; Sanchez, R.; Torrent, M.; Vacca, J. P.; Wan, B.-L.; Yan. Y. The design and synthesis of diaryl ether second generation HIV-1 non-nucleoside reverse transcriptase inhibitors (NNRTIs) with enhanced potency versus key clinical mutations. Bioorg. Med. Chem. Lett. 2008, 18, 2959-2966.

Sweeney, Z. K.; Harris, S. F.; Arora, N.; Javanbakht, H.; Li, Y.; Fretland, J.; Davidson, J. P.; Billedeau, J. R.; Gleason, S. K.; Hirschfeld, D.; Kennedy-Smith, J. J.; Mirzadegan, T.; Roetz, R.; Smith, M.; Sperry, S.; Suh, J. M.; Wu, J.; Tsing, S.; Villasenor, A. G.; Paul, A.; Su, G.; Heilek, G.; Hang, J. Q.; Zhou, A. S.; Jernelius, J. A.; Zhang, F.-J.; Klumpp, K. Design of annulated pyrazoles as inhibitors of HIV-1 reverse transcriptase. J. Med. Chem. 2008, 51, 7449-7458.

Sweeney, Z. K.; Acharya, S.; Briggs, A.; Dunn, J. P.; Elworthy, T. R.; Fretland, J.; Giannetti, A. M.; Heilek, G.; Li, Y.; Kaiser, A. C.; Martin, M.; Saito, Y. D.; Smith, M.; Suh, J. M.; Swallow, S.; Wu, J.; Hang, J. Q.; Zhou, A. S.; Klumpp, K. Discovery and optimization of pyridazinone non-nucleoside inhibitors of HIV-1 reverse transcriptase. Bioorg. Med. Chem. Lett. 2008, 18, 4352-4354.

Pelemans H. ; Esnouf R.; De Clercq E.; Balzarini J.Mol Pharmacol. 2000 57, 954-960.

Auwerx J.; Van Nieuwenhove J.; Rodriguez-Barrios F.; de Castro S.; Velázquez S.; Ceccherini-Silberstein F.; De Clercq E.; Camarasa MJ.; Perno CF.; Gago F.; Balzarini J. FEBS Lett. 2005 , 579, 2294-300.

Nerdinger, S.; Kendall, C.; Cai, X.; Marchart, R.; Riebel, P.; Johnson, M. R.; Yin, C. F.; Eltis, L. D.; Snieckus, V., Combined Directed ortho Metalation/Suzuki-Miyaura Cross-Coupling Strategies. Regiospecific Synthesis of Chlorodihydroxybiphenyls and Polychlorinated Biphenyls. J Org Chem 2007, 72, (16), 5960-5967.

Katz, L.; Cohen, M. S., Benzoxazol Derivatives. I. 2-Mercaptobenzoxazoles. J Org Chem 1954, 19, (5), 758-766.

Halley, F.; Sava, X., Synthesis of 5-Cyanoindazole and 1-Methyl and 1-Aryl-5-Cyanoindazoles. Synthetic Communications 1997, 27, (7), 1199-1207.

Zbinden, K.G.; Banner, D. W.; Hilpert, K.; Himber, J.; Lavé, T,; Riederer, M. A.; Stahl, M.; Tschopp, T. B.; Obst-Sander, U., Dose-dependent antihrombotic activity of an orally active tissue factor/factor Vlla inhibitor without concomitant enhancement of bleeding propensity. Bioorg. Med. Chem. 2006, 14, (15), 5357-5369.

\* cited by examiner synthetic scheme for JLJ 539 and derivatives synthetic scheme for JLJ 547 and derivatives a) NaH, benzenesulfonyl chloride, THF, rt  b) LDA, CH₃I, THF, -78°C  c) 5N NaOH, DME, EtOH, reflux, d) NaH, 0°C, n-BuLi, -78°C, B(OCH₃)₃, r X = H, Cl, Me a) methyl azidoacetate, -40°C, NaOMe, d) xylene, reflux, c) NaOH, HCl, d) oxalyl cloride, DCM, NH₃, H₂O, e) POCl₃, toluene, reflux, e) NaH, 0°C, n-BuLi, -78°C, B(OCH₃)₃, rt.

synthetic scheme for JLJ 550, 555

Synthesis of intermediate 2a

Synthesis of intermediate 2b

CATECHOL DIETHERS AS POTENT ANTI-HIV AGENTS

The present application is a United States national phase application of and claims the benefit of priority of International Application Number PCT/US2012/059886 filed in the United States Receiving Office on Oct. 12, 2012, which claims the benefit of priority of U.S. provisional application Ser. No. 61/546,285, filed Oct. 12, 2011, entitled "Catchol Diethers as Potent Anti-HIV agents, which is incorporated by reference in its entirety herein.

RELATED APPLICATIONS AND GOVERNMENT SUPPORT

The subject matter of this application was supported by grant nos. AI44616, GM32136 and GM49551 of the National Institutes of Health. Consequently, the government retains rights in the invention.

FIELD OF THE INVENTION

The present invention is directed to novel catechol diether compounds, pharmaceutical compositions therefrom and methods for inhibiting reverse transcriptase and treating HIV infections, especially included drug resistant strains of HIV 1 and 2 and/or secondary disease states and/or conditions which occur as a consequence of HIV infection.

BACKGROUND OF THE INVENTION

Though inhibition of multiple HIV proteins is therapeutically viable, HIV reverse transcriptase (RT) has been the key target.[1] Nucleoside RT inhibitors (NRTIs) including AZT are incorporated into the product DNA causing premature strand termination, while the non-nucleoside RT inhibitors (NNRTIs) bind to an allosteric site ca. 10-Å away from the polymerase active site.[2] The present inventors' efforts at discovery of new NNRTIs are intended to address continuing issues concerning the possible emergence of new viral strains, improved dosing, long-term tolerability, and safety.[3] Numerous compounds in multiple series have been prepared that are both potent against the wild-type (WT) virus and that have auspicious computed pharmacological properties.[4,5] Improvement in the performance of these compounds against clinically relevant viral variants is still desired. To address resistance from the outset, docking was done on multiple RT structures to seek consensus high-scoring hits. More than two million compounds from the ZINC library were screened with Glide using a conventional WT structure (1rt4), one with an alternative "down" conformation for Tyr181 (2be2), and a structure that incorporated the troublesome Tyr181Cys mutation (1jla).[6] Though only nine compounds were purchased, three showed 5-12 μM activity against one or both viral strains in infected T-cell assays.

As described here, among the three actives, we have most pursued lead-optimization for compound 1, which showed 4.8 μM potency towards WT HIV-1.[6] 1 bears some structural similarity to the ligands, TNK-651 (2) and R221239 (3), from the 1 jla and 2be2 crystal structures, respectively.[7,8] Their roots can be traced back further to thymine analogs in the HEPT class including emivirine (MKC-442, 4), which progressed to phase III clinical trials.[9] Various attributes of 1 are appealing including that it is a diphenylmethane derivative with a novel terminal uracil group, it likely has diminished metabolic liabilities compared to 3 and better computed aqueous solubility according to QikProp,[10] and refinement of substituents in the phenyl rings can be expected to be productive. Thus, optimization of 1 was initiated using a computationally driven approach, primarily guided by results of free-energy perturbation (FEP) calculations for complexes of the inhibitors with HIV-RT.[4]

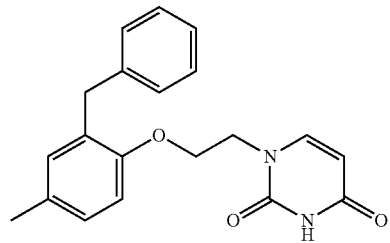

1

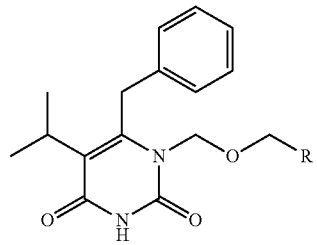

2 TNK-651 (R = Ph)
4 emivirine (R = CH₃)

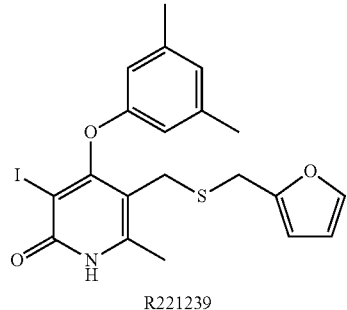

R221239

3

BRIEF DESCRIPTION OF THE INVENTION

Figure 1:
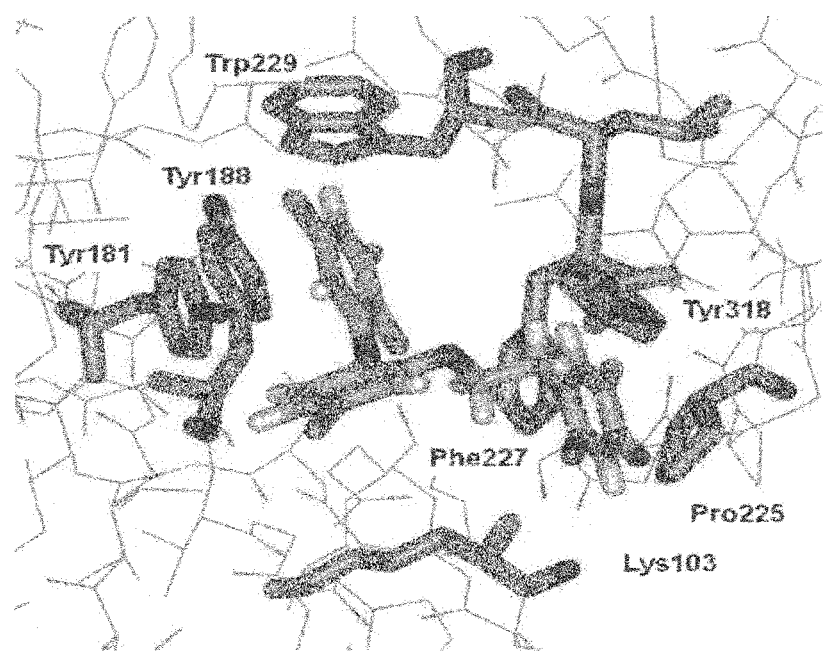
FIG. 1 shows the computed structures of a catechol diether (31) bound to HIV-RT starting from the 2be2 crystal structure. Two possible conformations of the uracilylethoxy sidechain, gaa (A) and aag (B), are illustrated. Carbon atoms of the inhibitor are colored gold.
Figure 1:
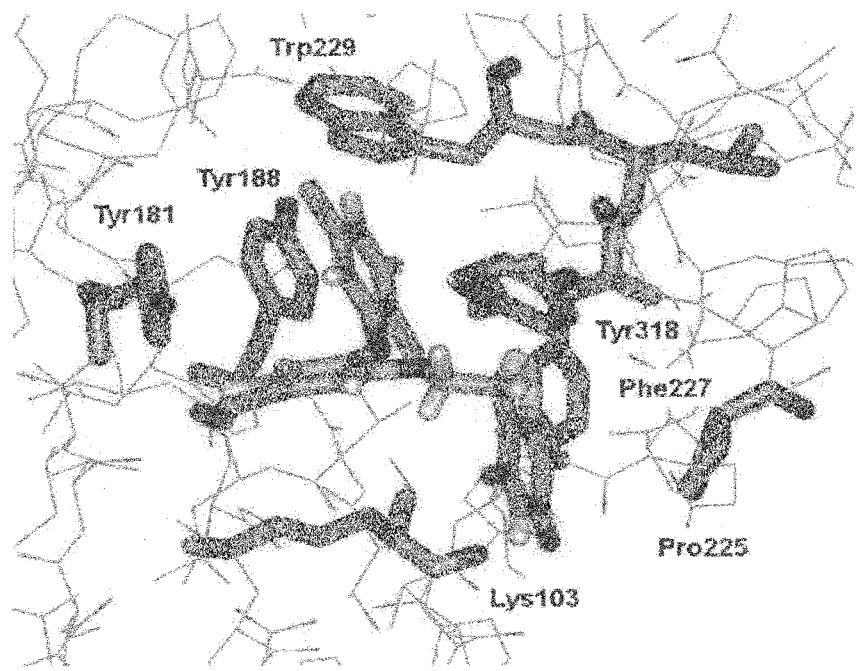

The present invention relates to compounds according to the chemical structure:

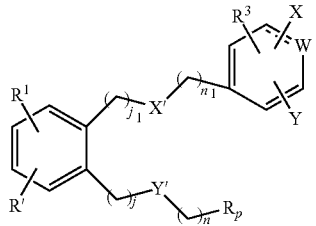

Wherein $R^1$ is H, OH, a halogen (F, Cl, Br, I), CN, $NO_2$, an optionally substituted alkyl group, preferably a $C_1$-$C_6$ alkyl group (preferably $CH_3$ and including $CF_3$), an optionally substituted $C_2$-$C_6$ alkene group, an optionally substituted $C_2$-$C_6$ alkyne group, $-(CH_2)_m-NR^AR^B$, $-(CH_2)_m-C(O)NR^AR^{B1}$, $-(CH_2)_m-NR^AC(O)R^C$, $-(CH_2)_m-O-(C_1$-$C_6)$ alkyl which is optionally substituted, $-O-(CH_2)_m-O-(C_1$-$C_6)$ alkyl which is optionally substituted, $-(CH_2)_m-O-(CH_2)_m-O-(C_1$-$C_6)$ alkyl which is optionally substituted, $-(CH_2)_m-C(O)-(C_1$-$C_6)$ alkyl which is optionally substituted, $-(CH_2)_m-OC(O)-C_1$-$C_6$ alkyl which is optionally substituted, or $-(CH_2)_m-C(O)O-C_1$-$C_6$ alkyl which is optionally substituted;

$R^A$ and $R^B$ are each independently H or an optionally substituted $C_1$-$C_6$ alkyl group (if substituted, preferably substituted with one or two hydroxyl groups);

$R^{B1}$ is H, an optionally substituted $C_1$-$C_6$ alkyl group (if substituted, preferably substituted with one or two hydroxyl groups) or an optionally substituted $-(CH_2)_m-O-(C_1$-$C_6)$ alkyl group;

$R^C$ is H, an optionally substituted $C_1$-$C_6$ alkyl group (if substituted, preferably substituted with one or two hydroxyl groups) or an optionally substituted $-(CH_2)_m-O-(C_1$-$C_6)$ alkyl group;

R' is H, OH, a halogen (F, Cl, Br, I), CN, $NO_2$, an optionally substituted $C_1$-$C_6$ alkyl group (preferably $CH_3$ and including $CF_3$), $-(CH_2)_m-O-(C_1$-$C_6)$ alkyl which is optionally substituted, $-O-(CH_2)_m-O-(C_1$-$C_6)$ alkyl which is optionally substituted, $-(CH_2)_m-C(O)-(C_1$-$C_6)$ alkyl which is optionally substituted, $-(CH_2)_m-OC(O)-C_1$-$C_6$ alkyl which is optionally substituted, or $-(CH_2)_m-C(O)O-C_1$-$C_6$ alkyl which is optionally substituted;

X' and Y' are each independently a bond (absent), O, S, S(O) (sulfoxide) or S(O)(O)(sulfone), preferably O or S, more preferably O;

$j, j_1, m, n$ and $n_1$ are each independently 0, 1, 2 or 3;

X, Y and $R^3$ are each independently H, OH, a halogen (F, Cl, Br, I), CN, $NO_2$, an optionally substituted $C_1$-$C_6$ alkyl group (preferably $CH_3$ and including $CF_3$), an optionally substituted $C_2$-$C_6$ alkene group (especially including a cyanovinyl or chlorovinyl group), an optionally substituted $C_2$-$C_6$ alkyne group, $-(CH_2)_m-NR^AR^B$, $-(CH_2)_m-C(O)NR^AR^{B1}$, $-(CH_2)_m-NR^NC(O)R^C$, $-(CH_2)_m-O-(C_1$-$C_6)$ alkyl which is optionally substituted, $-O-(CH_2)_m-O-(C_1$-$C_6)$ alkyl which is optionally substituted, $-(CH_2)_m-C(O)-(C_1$-$C_6)$ alkyl which is optionally substituted, $-(CH_2)_m-OC(O)-C_1$-$C_6$ alkyl which is optionally substituted, or $-(CH_2)_m-C(O)O-C_1$-$C_6$ alkyl which is optionally substituted, or X and Y, together with W, form an optionally substituted pyrrole ring, an optionally substituted dihydrofuran ring or an optionally substituted dihydropyrrole ring;

W is N or C, wherein when W is N, W, X and Y together form an optionally substituted five-membered pyrrole ring (resulting in the formation of a benzopyrrole or indolizine) and when W is C, C may be substituted with X, Y or $R^3$, or alternatively, W, X and Y form an optionally substituted dihydrofuran ring (resulting in the formation of a benzofuran group) or an optionally substituted dihydropyrrole ring (resulting in the formation of an indole group); and $R_p$ is an optionally substituted $C_1$-$C_6$ alkyl group or an optionally substituted 5- or 6-membered heterocyclic group (preferably a pyrimidine group such as uracil or cytosine, often uridine, which is optionally substituted with $R^{2a}$ on the 5- or 6-position, preferably the 5-position as is otherwise described herein), or a pharmaceutically acceptable salt, enantiomer, stereoisomer, solvate or polymorph thereof.

In preferred compounds according to the present invention, $R^1$ and R' are each independently H, halogen (preferably F or Cl) CN, $NO_2$, $NH_2$ or $NHCH_3$. In particularly preferred compounds both $R^1$ and R' are halogens, more preferably H and Cl or F or alternatively H and an alkyl substituted amine ($NHCH_3$), H and a CN group and H and a morpholinylmethoxy or morpholinyl ethoxy group. In other preferred compounds, X and Y are each independently H, halogen (preferably F or Cl), CN, $NO_2$, (E)-cyanovinyl, methoxyethoxy or 3-hydroxypropan-1-oxy. In further preferred compounds according to the invention, X' and Y' are both O, j, $j_1$ and $n_1$ are each a bond (i.e., absent) and j is 1 or 2, preferably 2. In additional preferred compounds according to the invention, Rp is a pyrimidine, preferably uracil (preferably attached at the N-1 position) and $R^{2a}$ (at the 5- or 6-position, preferably at the 5-position of uracil) is preferably H, F or Cl, more preferably H.

Preferred compounds according to the present invention include compounds according to the formula:

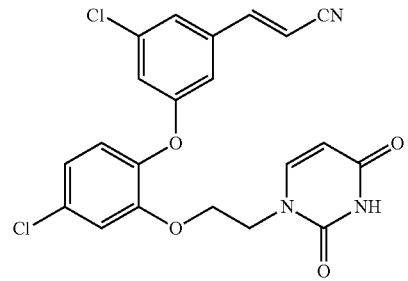

-continued

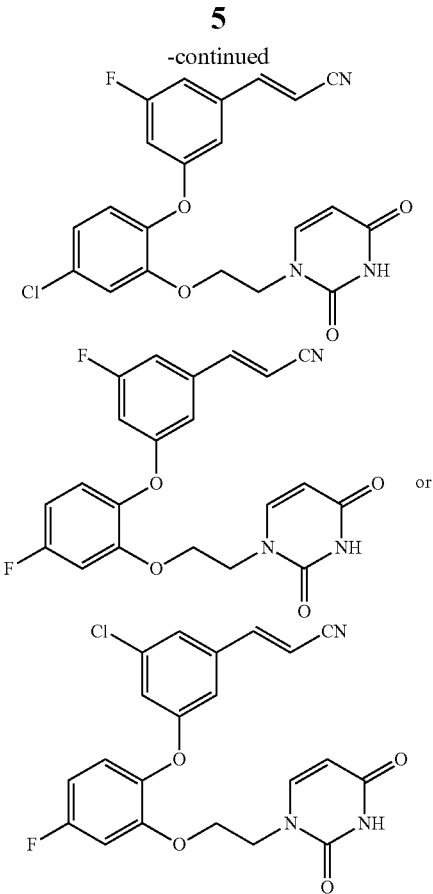

In still other embodiments, the present invention is directed to a compound according to the structure:

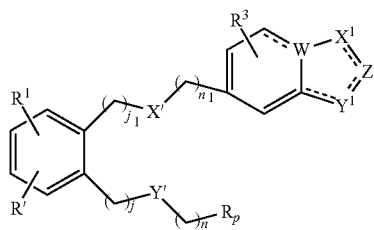

Where W, R¹, R', R³X¹, Y', j, j₁, n, n₁ and $R_p$ are the same as set forth above (Rp is preferably a pyrimidine substituted at the 5 or 6-position with a substituent $R^{2a}$; where $R^{2a}$ is H, halogen, preferably F, Cl or Br, optionally substituted $C_1$-$C_3$ alkyl, preferably methyl, ethyl or trifluoromethyl, optionally substituted —O—($C_1$-$C_3$) alkyl (methyl, ethyl, propyl, isopropyl), including O—$CF_3$, CN);

$X^1$ is

O or N—$R^x$ when W is C, and

when W is N;

Z is

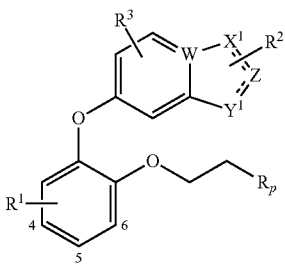

(the double bond can be on either side of the carbon depending on $X^1$ and $Y^1$);
$Y^1$ is

—C(=CH₂)—R²,

O or N—$R^Y$ when W is C, and

—C(=CH₂)—R² when W is N;
$R^2$ is H, a $C_1$-$C_3$ alkyl optionally substituted with up to three fluorines (e.g. $CF_3$), CN or halogen (F, Br, Cl, I); and
$R^X$ and $R^Y$ are each independently H or a $C_1$-$C_6$ alkyl (or a $C_1$-$C_3$ alkyl) group, optionally substituted with one or two hydroxyl groups, or
a pharmaceutically acceptable salt, enantiomer, stereoisomer, solvate or polymorph thereof.

In certain embodiments, in the present compounds, $R^3$ is H, OH, a $C_1$-$C_3$ alkyl group which is optionally substituted with up to three halogens (preferably F), —O—$C_1$-$C_3$ alkyl, which is optionally substituted with up to three halogs (preferably F), a halogen (preferably F, Cl or Br), $NO_2$ or CN.

In other embodiments, compounds according to the present invention are represented by the chemical structure:

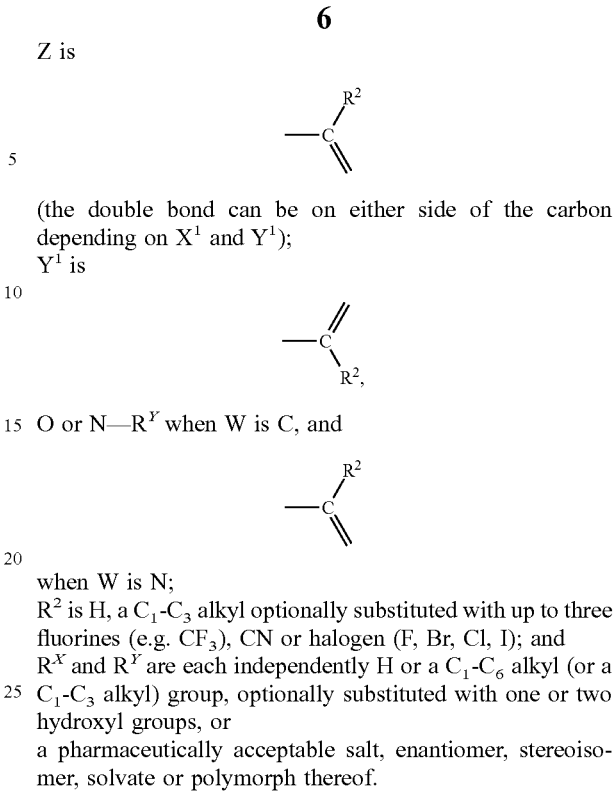

Where $R^1$ is H, a halogen (F, Cl, Br, I, especially F, Cl, or Br), CN, $NO_2$, an optionally substituted alkyl group, preferably a $C_1$-$C_6$ alkyl group (preferably $CH_3$ and including $CF_3$);
$R^2$ is H, a $C_1$-$C_3$ alkyl optionally substituted with up to three fluorines (e.g. CF3), CN or halogen (preferably F, Br or Cl);
$R^3$ is H, OH, a $C_1$-$C_3$ alkyl group which is optionally substituted with up to 3 halogens (preferably F), a halogen (preferably F, Cl or Br), $NO_2$ or CN;
Rp is an optionally substituted pyrimidine preferably linked at the 1-position of the pyrimidine, more often a uracil moiety optionally substituted at the 5- or 6-position (often the 5-position) with a substituent $R^{2a}$;
$R^{2a}$ is H, halogen (preferably F, Cl or Br), optionally substituted $C_1$-$C_3$ alkyl (preferably methyl, ethyl or trifluoromethyl), optionally substituted —O—($C_1$-$C_3$) alkyl (methyl, ethyl, propyl, isopropyl), including O—$CF_3$, CN;
W is N or C;

$X^1$ is

O or N—$R^x$ when W is C, and

when W is N;

Z is

(the double bond can be on either side of the carbon depending on $X^1$ and $Y^1$);

$Y^1$ is

O or N—$R^Y$ when W is C, and

when W is N;

$R^2$ is H, a $C_1$-$C_3$ alkyl optionally substituted with up to three fluorines (e.g. $CF_3$), CN or halogen (F, Br, Cl, I); and $R^X$ and $R^Y$ are each independently H or a $C_1$-$C_6$ alkyl (or a $C_1$-$C_3$ alkyl) group, optionally substituted with one or two hydroxyl groups.

or a pharmaceutically acceptable salt, solvate or polymorph thereof.

In additional embodiments according to the present invention, the compound is

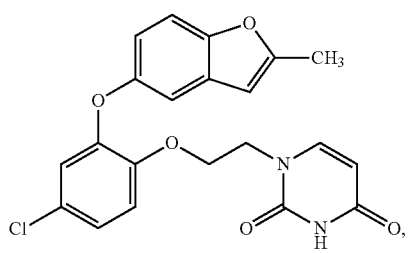

-continued

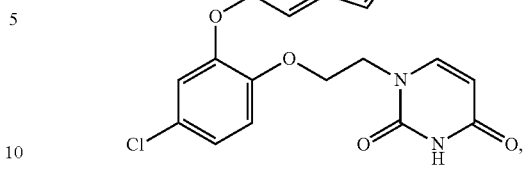

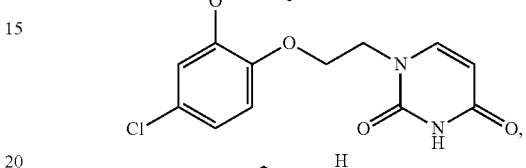

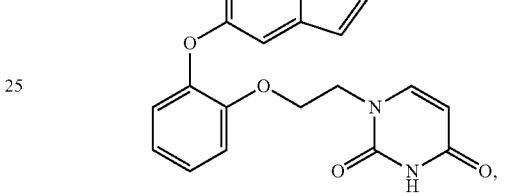

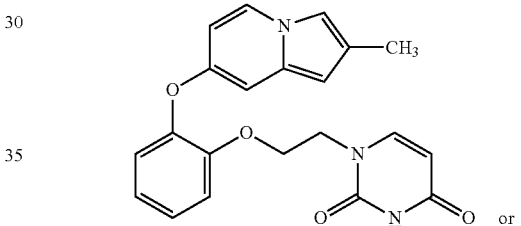

or

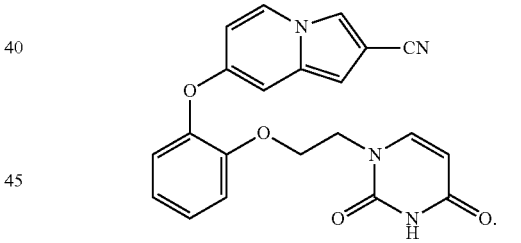

In an alternative aspect of the present invention, a pharmaceutical composition comprises an effective amount of at least one compound described above, in combination with a pharmaceutically acceptable carrier, additive or excipient and optionally in combination with at least one additional anti-HIV agent.

In another embodiment according to the present invention, pharmaceutical compositions comprise an effective amount of one or more compounds as described above, optionally in combination with a pharmaceutically acceptable carrier, excipient or additive. Pharmaceutical compositions may also include, in addition to the present compounds, at least one additional compound, including another anti-HIV agent which inhibits HIV by a mechanism other than through reverse transcriptase inhibition, although other reverse transcriptase inhibitors may be used, especially nucleoside reverse transcriptase inhibitors (NRTIs).

In another embodiment, the present application is directed to a method for inhibiting reverse transcriptase (HIV) comprising exposing reverse transcriptase to at least one compound described above, optionally in combination with at least one additional non-nucleoside reverse transcriptase inhibitor (NNRTI) and/or at least one additional nucleoside reverse transcriptase inhibitor (NRTI). The exposure may be in vitro or in vivo (preferably, in vivo).

In yet another embodiment, the present application is directed to the treatment HIV infections and its secondary disease states and conditions, including the treatment of AIDS and ARC, said method comprising administering to a patient in need thereof an effective amount of a pharmaceutical composition comprising any one or more of the compounds previously described above, optionally in combination (coadministered) with another active agent, preferably another anti-HIV agent as otherwise disclosed herein.

DETAILED DESCRIPTION OF THE INVENTION

In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein. Within its use in context, the term generally refers to a single compound comprising a hydrophobic moiety and a linker which is capable of reacting and forming a covalent bond with a fusion protein as otherwise described herein. In certain instances the term may also refer to stereoisomers and/or optical isomers (including racemic mixtures) or enantiomerically enriched mixtures of disclosed compounds. Compounds which are disclosed are those which are stable and where a choice of substituents and claim elements is available, the substituent or claim element is chosen such that stable compounds are formed from the disclosed elements and substituents. The symbol ----- in a chemical structure or formula signifies that either a double or single bond may be present between the atoms to which such symbol is attached, depending upon the valence of those atoms and substituents which are on such atoms.

The term "patient" or "subject" is used throughout the specification within context to describe an animal, especially including a domesticated mammal and preferably a human, to whom a treatment or procedure, including a prophylactic treatment or procedure is performed. For treatment of those infections, conditions or disease states which are specific for a specific animal such as a human patient, the term patient refers to that specific animal. In most instances, the patient or subject of the present invention is a domesticated/agricultural animal or human patient of either or both genders.

The term "effective" is used herein, unless otherwise indicated, to describe an amount of a compound or composition which, in context, is used to produce or effect an intended result, whether that result relates to the inhibition of reverse transcriptase or to the inhibition of growth and/or the treatment of HIV or a secondary disease state or conditions such as AIDS or ARC in a patient or subject. The term effective subsumes all other effective amount or effective concentration terms which are otherwise described or used in the present application.

The term "human immunodeficiency virus" shall be used to describe human immunodeficiency virus (HIV) and its infections, which term shall be used to embrace both human immunodeficieny virus 1 (HIV-1) and human immunodeficiency virus 2 (HIV-2).

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes used synonymously.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substituent groups in compounds according to the present invention are as conventionally used in the art.

The term "aryl" or "aromatic", in context, refers to a substituted or unsubstituted monovalent aromatic radical having a single ring (e.g., benzene or phenyl). Other examples of aryl groups, in context, may include heterocyclic aromatic ring systems "heteroaryl" groups having one or more nitrogen, oxygen, or sulfur atoms in the ring (5- or 6-membered heterocyclic rings) such as imidazole, furyl, pyrrole, pyridyl, furanyl, thiene, thiazole, pyridine, pyrimidine, pyrazine, triazole, oxazole, among others, which may be substituted or unsubstituted as otherwise described herein.

The term "heterocyclic group" "heterocycle" as used throughout the present specification refers to an aromatic ("heteroaryl") or non-aromatic cyclic group forming the cyclic ring and including at least one and up to three hetero atoms such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, thiophene, furan, pyran, thiazole, more preferably pyrimidinyl, pyrrolidinyl, piperidinyl, morpholinyl, oxazole, isoxazole, pyrrole, pyridine, thiophene, thiazole and even more preferably pyrimidinyl, especially uracil or cytosine which are optionally substituted, furyl, 3-methylfuryl, thiazole, piperazinyl, N-methylpiperazinyl, tetrahydropyranyl and 1,4-dioxane, among others. Additional heterocyclic groups include oxazole, benzoxazole, pyrrole, dihydropyrrole, benzopyrrole, benzodihydropyrrole, indole, indolizine, among others.

Preferred heterocyclic groups $R_p$ are less than fully saturated and more preferably are pyrimidine groups, especially including uracil or cytosine groups which may be substituted at the 5- or 6-position (especially the 5-position) of the pyrimidine ring, especially 5-substituted uracil or cytosine groups according to the chemical structure:

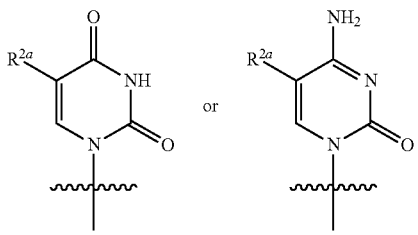

Where $R^{2a}$ is H, halogen (preferably F, Cl or Br), optionally substituted $C_1$-$C_3$ alkyl (preferably methyl, ethyl or trifluoromethyl), optionally substituted —O—($C_1$-$C_3$) alkyl (methyl, ethyl, propyl, isopropyl), including O—$CF_3$, CN.

Exemplary heteroaryl moieties which may be used in the present invention include for example, pyrrole, pyridine, pyridone, pyridazine, pyrimidine, pyrazine, pyrazole, imidazole, triazole, tetrazole, oxadiazole, sulfur-containing aromatic heterocycles such as thiophene; oxygen-containing aromatic heterocycles such as furan and pyran, and including aromatic heterocycles comprising 2 or more hetero atoms selected from among nitrogen, sulfur and oxygen, such as thiazole, thiadiazole, isothiazole, isoxazole, furazan and oxazole. Further heteroaryl groups may include pyridine, triazine, pyridone, pyrimidine, imidazole, furan, pyran, thiazole. Pyrimidine groups, especially uracil and cytosine, optionally substituted, are preferred.

The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{10}$, more preferably, $C_1$-$C_6$), alkoxy group (preferably, $C_1$-$C_6$ alkyl or aryl, including phenyl and substituted phenyl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Preferably, the term "substituted" shall mean within its context of use alkyl, alkoxy, halogen, ester, keto, nitro, cyano and amine (especially including mono- or di-$C_1$-$C_6$ alkyl substituted amines which may be optionally substituted with one or two hydroxyl groups). Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

The term "human immunodeficiency virus" shall be used to describe human immunodeficiency virus I (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by RT mutation)—XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others, especially Y181C and/or K103N/Y181C, among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A category 2 (ARC) infection is characterized by the following criteria: The patient's T-cells have dropped below 500 but never below 200, and that patient has never had any Category 3 diseases (as set forth below) but have had at least one of the following defining illnesses:

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ Constitutional symptoms, such as fever (38.5 C) or diarrhea lasting longer than 1 month
  Hairy leukoplakia, oral
  Herpes zoster (shingles), involving at least two distinct episodes or more than one dermatome
  Idiopathic thrombocytopenic purpura
  Listeriosis
  Pelvic inflammatory disease, particularly if complicated by tubo-ovarian abscess
  Peripheral neuropathy
According to the U.S. government, in Category 2 ARC, the immune system shows some signs of damage but it isn't life-threatening.
A Category 3 (AIDS) infection is characterized by the following criteria:
  T-cells have dropped below 200 or
  Patent has (has had) at least one of the following defining illnesses—
  Candidiasis of bronchi, trachea, or lungs
  Candidiasis, esophageal
  Cervical cancer, invasive**
  Coccidioidomycosis, disseminated or extrapulmonary
  Cryptococcosis, extrapulmonary
  Cryptosporidiosis, chronic intestinal (greater than 1 month's duration)
  Cytomegalovirus disease (other than liver, spleen, or nodes)
  Cytomegalovirus retinitis (with loss of vision)
  Encephalopathy, HIV-related
  Herpes simplex: chronic ulcer(s) (greater than 1 month's duration); or bronchitis, pneumonitis, or esophagitis
  Histoplasmosis, disseminated or extrapulmonary
  Isosporiasis, chronic intestinal (greater than 1 month's duration)
  Kaposi's sarcoma
  Lymphoma, Burkitt's (or equivalent term)
  Lymphoma, immunoblastic (or equivalent term)
  Lymphoma, primary, of brain
  *Mycobacterium avium* complex or *M. kansasii*, disseminated or extrapulmonary
  *Mycobacterium tuberculosis*, any site (pulmonary** or extrapulmonary)
  *Mycobacterium*, other species or unidentified species, disseminated or extrapulmonary
  *Pneumocystis carinii* pneumonia
  Pneumonia, recurrent**
  Progressive multifocal leukoencephalopathy
  *Salmonella* septicemia, recurrent
  Toxoplasmosis of brain
  Wasting syndrome due to HIV The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2).

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2) and other viruses. The terms inhibitory effective amount or preventive effective amount also generally fall under the rubric "effective amount".

The term "coadministration" is used to describe the administration of two or more active compounds, in this case a compound according to the present invention, in combination with an additional anti-HIV agent or other biologically active agent, in effective amounts. Although the term coadministration preferably includes the administration of two or more active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

Compounds according to the present invention may be administered with one or more anti-viral agent, including other anti-HIV agents including nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), Festinavir, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other agents which may be used in coadministration with compounds according to the present invention include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2-methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4''-dimethoxy-5',5''-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), 5Cl3PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyl)-)carbonyl]-4-[3-(isopropylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyl)carbonyl]-4-[3-(isopropylamino)-2-pyridinyl]piperazine, 1-[[5-(Methylsulfonyloxy)-2-indoyl)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

Coadministration also includes the administration of other non anti-viral agents which may be beneficial for patients with HIV, AIDS or ARC or other secondary disease states or conditions of patients with HIV infections.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, transdermally, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically administered transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free compounds hynor pro-drug forms of the compounds according to the present invention.

In particularly preferred embodiments according to the present invention, the compounds and compositions are used to treat, prevent or delay the onset of viral infections of mammals and in particular HIV 1 and 2 infections in humans. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form. Compounds according to the present invention may also be used to reduce the likelihood that a HIV infection may worsen into AIDS or ARC symptoms and/or secondary disease states and/or conditions.

Certain compounds according to the present invention, because of their low toxicity to host cells, may advantageously be employed prophylactically to prevent (reduce the likelihood of) a viral infection or to prevent the occurrence of clinical symptoms associated with the viral infection, for example AIDS or ARC secondary to HIV. Thus, the present invention also encompasses methods for the prophylactic treatment (preventing, reducing the likelihood or delaying the onset) of viral infections, and in particular HIV and conditions which occur secondary to those virus infections. In this aspect according to the present invention, the present compositions are used to prevent reduce the likelihood of or delay the onset of a viral infection, in particular, HIV or a virus related disease or condition such as AIDS or ARC.

This prophylactic method comprises administering to a patient in need of such treatment or who is at risk for the development of an HIV or other viral infection or a disease state or condition which occurs secondary to an HIV infection, an amount of a compound according to the present invention effective for alleviating, preventing or delaying the onset of the viral infection or secondary condition or disease state. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV, including those presently used to treat HIV such as nucleoside reverse transcriptase inhibitors (NRTI), other non-nucleoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV, (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316,505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. Preferred secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

Compounds according to the present invention may be used as active agents in pharmaceutical compositions as inhibitors of reverse transcriptase and as anti-viral agents, said compositions comprising an effective amount of one or more of the compounds disclosed above, formulated as a pharmaceutical dosage form, optionally in combination with a pharmaceutically acceptable carrier, additive or excipient. Pharmaceutical compositions according to the present invention may be used in the treatment of HIV infections (all forms, including human immunodeficiency virus I and II), and numerous additional viral infections, especially including drug resistant forms of these viruses.

In other aspects of the present invention, certain compounds according to the present invention may be used as antagonists in binding assays, as analytical agents, as agents to be used to isolate or purify proteins (especially viral reverse transcriptase), and/or as intermediates in the synthesis of further agents, among other uses.

EXAMPLES

Experimental and Computational Methods

Synthetic Chemistry

Ultimately, the synthetic efforts of the present invention focused on preparation of diphenylmethanes (Scheme 1) and catechol diethers (Schemes 2-4). The o-benzylphenols in Scheme 1 arose from Friedel-Crafts reactions of arylmethyl halides or alcohols with phenols.[11,12] The catechol ether intermediates were prepared from substituted phenols and the aryl fluorides using $S_NAr$ reactions followed by treatment with boron tribromide or lithium chloride (Schemes 2 and 3). The final compounds were prepared in a two-step sequence via Mitsunobu reaction to install the bromoethoxy linker, followed by 2,4-bis(trimethylsiloxy)pyrimidine alkylation (5-15, 20-32).[13]

Scheme 1ᵃ. Synthesis of compounds 5-15
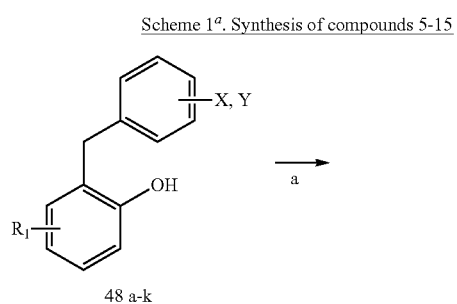
ᵃReagents:
(a) DIAD, bromoethanol, Ph₃P, THF, rt, overnight;
(b) 180° C., 1.5 h.
Scheme 2.ᵃ Synthesis of compounds 20-27.
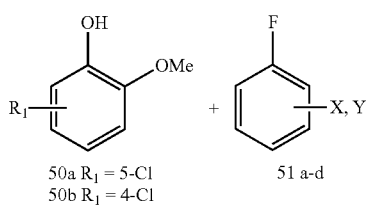
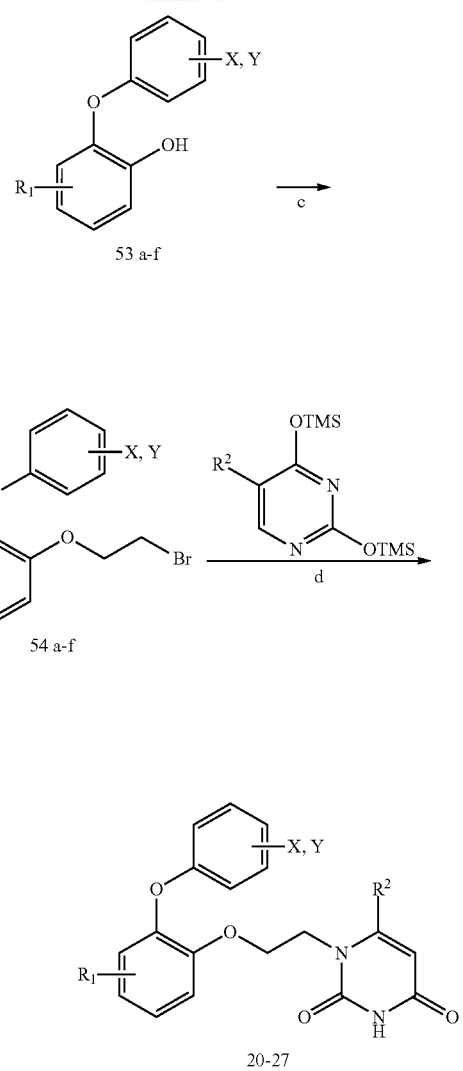
ᵃReagents:
(a) NaNO₂, conc HCl, CuCl, 80° C., 1 h;
(b) K₂CO₃, DMSO, 110° C. 2-5 h;
(c) BBr₃, CH₂Cl₂, -78° C., overnight;
(d) DIAD, bromoethanol, Ph₃P, THF, rt, overnight;
(f) 180° C., 1.5 h.
Scheme 3. ᵃSynthesis of compounds 28-32 and 40-47
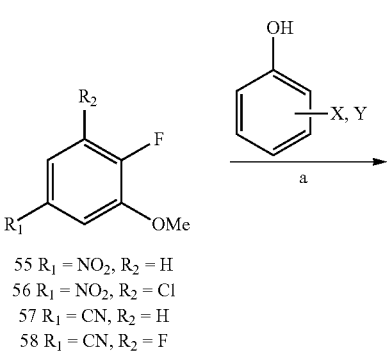
55 R₁ = NO₂, R₂ = H
56 R₁ = NO₂, R₂ = Cl
57 R₁ = CN, R₂ = H
58 R₁ = CN, R₂ = F

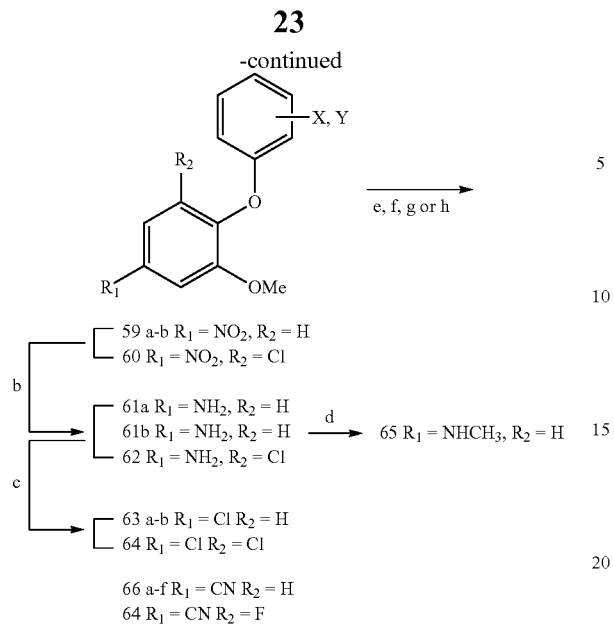

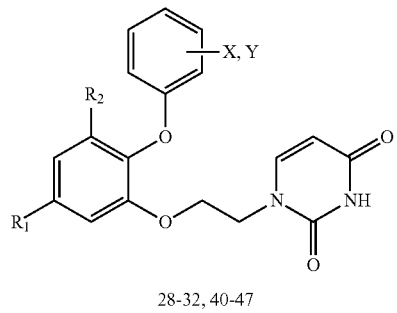
28-32, 40-47

*Reagents:
(a) K₂CO₃, DMSO, 110° C. 2-5 h;
(b) Fe, NH₄Cl, EtOH, H₂O, 75° C.;
(c) NaNO₂, conc HCl, CuCl, 80° C., 1 h;
(d) CH₃B(OH)₂, Cu(OAc)₂, py, dioxane, reflux;
(e) BBr₃, CH₂Cl₂, -78° C., overnight or LiCl, DMF 160° C., overnight;
(f) DIAD, bromoethanol, Ph₃P, THF, rt, overnight;
(g) 2,4-bis(trimethylsiloxy)pyrimidine, 180° C., 1.5 h or
(h) Bz-uracil, K₂CO₃, DMF, rt, overnight then NH₄OH, MeOH, rt.

However, when substituent 'X' was (E)-cyanovinyl, methoxyethoxy (MOEO) or 3-hydroxypropan-1-oxy (HOPO), the last step did not yield the desired product. To circumvent this, the N-benzoyl uracil derivatives[14] were made followed by alkylation with the alkyl bromide and cleavage of the benzoyl moiety to afford the target compounds in good yields (35-42).[15]

In particular, when 3-cyanovinyl-substituted catechol ethers were required, Heck coupling of aryl iodides with acrylonitrile using PdCl₂(PPh₃)₂ as catalyst was effective. This reaction afforded separable mixtures of E:Z (70:30) stereoisomers in 50-70% yield.

Finally, compounds 33 and 34 were obtained via Mitsunobu reaction with the corresponding alcohols and catechol ethers (Scheme 4). For compound 35, the aliphatic linker was added via alkylation to 71 with 4-bromomethylpyridine. The identity of all assayed compounds was confirmed by ¹H and ¹³C NMR and high-resolution mass spectrometry; purity was >95% as judged by high-performance liquid chromatography Small molecule crystal structures were obtained by direct methods on data collected using a Rigaku Mercury2 CCD area detector with graphite monochromated Mo—Kα radiation.

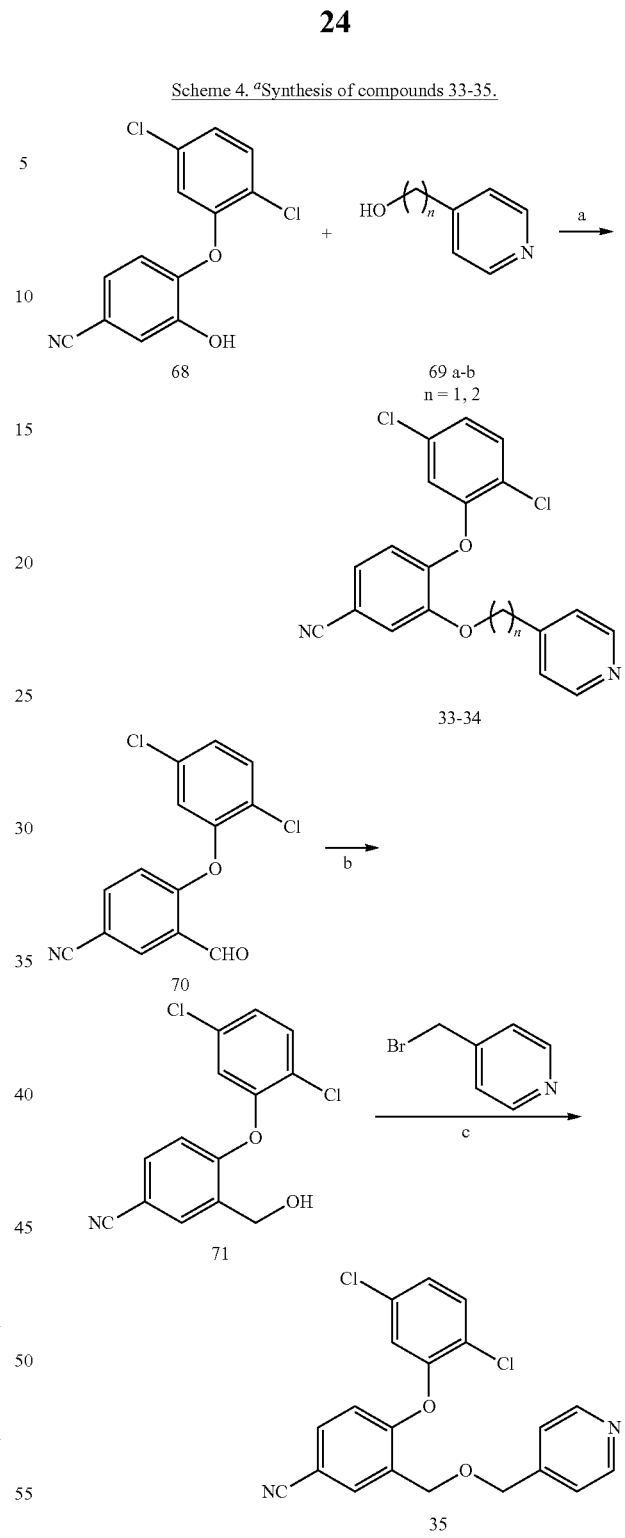

Scheme 4. *Synthesis of compounds 33-35.

*Reagents:
(a) DIAD, bromoethanol, Ph₃P, THF, rt, overnight;
(b) NaBH₄, MeOH, 0° C. to rt 3 h;
(c) NaH, DMF, rt, 2 h.

For the biology, activities against the IIIB and variant strains of HIV-1 were measured using MT-2 human T-cells; EC₅₀ values are obtained as the dose required to achieve 50% protection of the infected cells by the MTT colorimetric method. CC₅₀ values for inhibition of MT-2 cell growth by 50% are obtained simultaneously.[5,16,17] The antiviral and toxicity curves used triplicate samples at each concentration.

The principal computations were conjugate-gradient energy minimizations and Monte Carlo/FEP (MC/FEP) calculations, which yield relative free energies of binding. The calculations were performed with the MCPRO program[18] and followed standard protocols.[4,5] Coordinates of HIV-RT complexes were mostly constructed from the 2be2 crystal structure[8] using the BOMB program.[4] The model included the 175 amino acid residues nearest the ligand. Short conjugate-gradient minimizations were carried out on the initial structures for all complexes to relieve any unfavorable contacts. Coordinates for the free ligands were obtained by extraction from the complexes. The unbound ligands and complexes were solvated in TIP4P water spheres ("caps") with a 25-Å radius; after removal of water molecules in too close contact with solute atoms, ca. 2000 and 1250 water molecules remained for the unbound and bound MC simulations. The FEP calculations utilized 11 windows of simple overlap sampling.[19] Each window covered 10-15 million (M) configurations of equilibration and 10-30 M configurations of averaging at 25° C. The ligand side chains with any atom within ca. 10 Å of the ligand were fully flexible, while the protein backbone was kept fixed during the MC runs. The energetics were evaluated with the OPLS-AA force field for the protein,[20] OPLS/CM1A for the ligands,[21] and TIP4P for water.[22]

Results and Discussion

A typical structure for the complexes is illustrated in FIG. 1. As expected from the crystal structures for HEPT analogs and 3, the terminal phenyl ring resides in the π-box formed by Tyr181, Tyr188, Phe227, and Trp229, and the uracilylethoxy side chain projects into the channel lined by Pro225, Phe227, and Pro236. The computations further indicate that alternative conformations are possible for the side chain with the two illustrated in FIG. 1 as the most probable. The gauche-anti-anti (gaa) conformer on the left is close to that found for the methoxymethyl fragment in the crystal structures for HEPT analogs,[7] while the aag alternative allows formation of a hydrogen bond between the carbonyl group of Lys103 and the uracilyl NH. It should also be noted that the "down" orientation of the phenolic unit of Tyr181 follows from the 2be2 structure.[8] It is possible that for some of the inhibitors considered here that the "up" orientation with Tyr181 and Tyr188 more parallel, as in the HEPT structures,[7] is preferred.

Diphenylmethanes.

The MC/FEP calculations began with a chlorine scan for the terminal phenyl ring in 1. With numbering the ring such that the chlorines in FIG. 1 are at the 2- and 5-positions, replacement of hydrogen by chlorine was predicted to be favorable (more negative free energy of binding, $\Delta G_b$) by 1.4, 1.9 and 3.8 kcal/mol at C2, C5 and C6 and unfavorable by 1.4 and 0.7 kcal/mol at C3 and C4. The computed uncertainties are ±0.2 kcal/mol. However, since double substitution was envisioned and the results might not be additive, MC/FEP calculations were executed for all 10 unique dichloro possibilities, as summarized in Table 1. Such exhaustive double substituent scans should find general utility in ligand design. The results continued to support the viability of substitutions at C2, C5, and C6 with the most favorable di-substitutions being C2/C5, C2/C6, and C4/C6, which correspond to the 2,5-, 2,6-, and 2,4-dichloro analogs. The 3,5-dichloro analog is also predicted to be better bound than the parent compound. A term that could be added for the 3,5- and 2,6-analogs is a factor of two symmetry benefit (−0.4 kcal/mol) over the unsymmetrical 2,5- or 2,4-analogs, since only one conformer is favorable in the latter cases (C2/C5 and C4/C6).

TABLE 1

MC/FEP Results for the Change in Free Energy of Binding upon Introducing Two Chlorines in the Terminal Phenyl Ring[a]

| H to Cl | $\Delta\Delta G_b$ | σ |
|---|---|---|
| C2/C3 | 2.00 | 0.18 |
| C2/C4 | 2.43 | 0.20 |
| C2/C5 | −2.12 | 0.22 |
| C2/C6 | −3.69 | 0.25 |
| C3/C4 | 6.27 | 0.23 |
| C3/C5 | −1.13 | 0.19 |
| C3/C6 | 3.63 | 0.24 |
| C4/C5 | 1.79 | 0.23 |
| C4/C6 | −2.26 | 0.21 |
| C5/C6 | 2.52 | 0.20 |

[a]$\Delta\Delta G_b$ is the computed change in free energy of binding (kcal/mol) for introducing the two chlorines; ±σ is the computed uncertainty. C6 is proximal to Tyr181 in the binding site (see FIG. 1)

Related experimental results are presented in Table 2. The methyl group in 1 was replaced by chlorine to give 5, which is more potent against the WT virus with an $EC_{50}$ of 1.2 μM. For substitution in the terminal phenyl ring, 2-Cl substitution (6) was found to be more favorable than the 3-Cl alternative (7) consistent with the computed results for C2(C6) and C3(C5). The di-substituted compounds also mostly followed the computed trends with the most potent being the 2,6-analog (11) at 310 nM, which was followed by the 2,5- and 3,5-analogs, 10 and 9, at 380 nM and 1.3 μM. The 2,4-dichloro analog 8 was less active than anticipated and the range of activities was compressed from what might have been expected from the computed $\Delta\Delta G_b$ values. The compression is normal and may result from comparing free energies of binding with results of cell-based assays and force-field inadequacies.[4,5] Overall, a ca. 15-fold gain in potency was achieved in going from 1 to 10 or 11. It is notable that the FEP calculations pointed out the viability of 2,5- and 2,6-disubstitution, whereas the literature on more potent HEPT and emivirine analogs is dominated by 3,5-disubstituted cases.[23] The same is true for the compounds in the 3-series.[24] In the absence of the FEP results, even with display of the optimized structures, the preferences are not obvious. Most of the disubstituted possibilities look reasonable with the possible exception of X or Y=4-Cl, which appears to yield a steric conflict with Trp229.

TABLE 2

Anti-HIV-1 Activity ($EC_{50}$) and Cytotoxicity ($CC_{50}$), μM, of Diphenylmethane Derivatives

| Compd | $R^1$ | X | Y | $R^2$ | $EC_{50}$ | $CC_{50}$ |
|---|---|---|---|---|---|---|
| 1 | 4-Me | H | H | H | 4.8 | 72 |
| 5 | 4-Cl | H | H | H | 1.2 | 23 |
| 6 | 4-Cl | 2-Cl | H | H | 0.62 | 28 |
| 7 | 4-Cl | 3-Cl | H | H | 1.5 | 11 |
| 8 | 4-Cl | 2-Cl | 4-Cl | H | 2.9 | 88 |
| 9 | 4-Cl | 3-Cl | 5-Cl | H | 1.3 | 10 |
| 10 | 4-Cl | 2-Cl | 5-Cl | H | 0.38 | 15 |
| 11 | 4-Cl | 2-Cl | 6-Cl | H | 0.31 | 49 |
| 12 | 4-Cl | H | H | Me | 2.4 | 22 |
| 13 | 4-Cl | H | H | F | 2.5 | 27 |
| 14 | 4-Cl | H | H | Cl | 2.2 | 21 |
| 15 | 5-Cl | 2-Cl | H | H | 0.41 | 12 |

Several additional diphenylmethane derivatives were prepared. The results for 12-14 in comparison with 5 demonstrate that substitution at the 5-position in the uracil ring is not beneficial, while the results for 15 vs. 6 show that a 5-Cl substituent in the central ring is somewhat preferred to the 4-Cl isomer.

Catechol Diethers.

The next consideration was the position of the oxygen in the linkers, especially given the alternatives suggested by 2 and 3. Thus, MC/FEP calculations were executed for perturbing structure 16 with X=Y=Z=CH$_2$ to the three compounds in which X, Y, or Z are individually oxygen. The resultant $\Delta\Delta G_b$ values were −5.95, 0.64, and −2.07 kcal/mol, respectively, with uncertainties of ±0.3 kcal/mol. Thus, the phenoxy substructure as in 3 was predicted to be much favored. This likely reflects conformational preferences.[25] It is easier for a diphenyl ether fragment than a diphenylmethane one to achieve the near perpendicular arrangement, illustrated in FIG. 1, which is most complimentary to the positioning of Tyr188

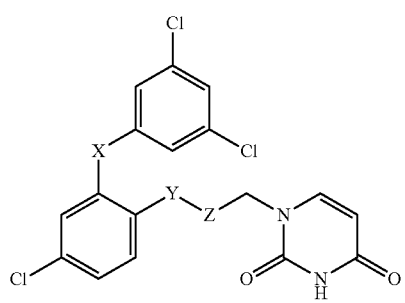

16

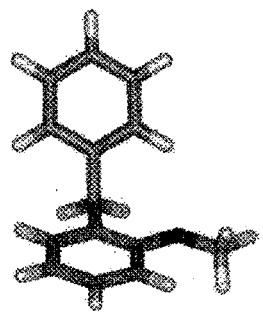

17

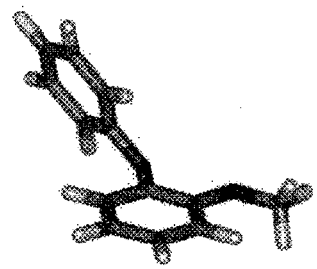

18

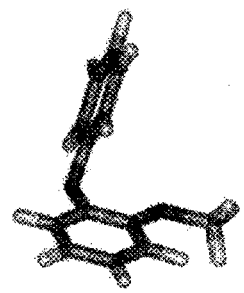

19 and Trp229. In fact, when a gas-phase conformational search is performed for the parent o-methoxy derivatives of diphenylmethane and diphenyl ether with the OPLS-AA force field, conformers 17 and 18 are the global minima. For 17, there is only this minimum, while there are 5 unique minima for 18. Conformer 19 is the second minimum, only 0.37 kcal/mol higher in energy than 18. Thus, catechol diethers like 18 are well pre-organized to bind to HIV-RT in the desired manner (FIG. 1).

Given these results, a complete dichlorine FEP scan was performed for the model inhibitor in Table 3. The results favor 2,3-, 2,5-, and 3,5-substitution with the 2,5-pattern, illustrated in FIG. 1, the most favored. A mono-chlorine scan for the catechol ring was also performed for the corresponding 3,5-dichlorophenyl analog. This yielded $\Delta\Delta G_b$ values of −1.2, −2.6, −3.1, and −2.8 kcal/mol (±0.2 kcal/mol) for introducing a chlorine at the 3',4',5', and 6' positions. Consequently, the synthetic focus turned to catechol diethers with the favored substitution patterns in both rings. However, since $S_NAr$ chemistry was envisioned for the synthesis of the core (Schemes 2 and 3), an activating group was needed in one of the rings; cyano groups were chosen as they are the most similar sterically to chlorine and model-building indicated that they should be viable.

TABLE 3

MC/FEP Results for the Change in Free Energy of Binding (kcal/mol) upon Introducing Two Chlorines in a Catechol Diether

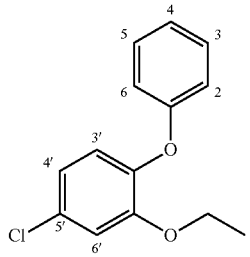 [SMILES: CCOc1cc(Cl)ccc1Oc1ccccc1]

| H to Cl | ΔΔG$_b$ | σ |
|---|---|---|
| C2/C3 | −3.87 | 0.14 |
| C2/C4 | 1.88 | 0.20 |
| C2/C5 | −5.56 | 0.18 |
| C2/C6 | 1.44 | 0.21 |
| C3/C4 | 2.82 | 0.18 |
| C3/C5 | −3.28 | 0.15 |
| C3/C6 | 6.26 | 0.24 |
| C4/C5 | 2.16 | 0.17 |
| C4/C6 | 6.42 | 0.30 |
| C5/C6 | 4.48 | 0.19 |

Figure 2:
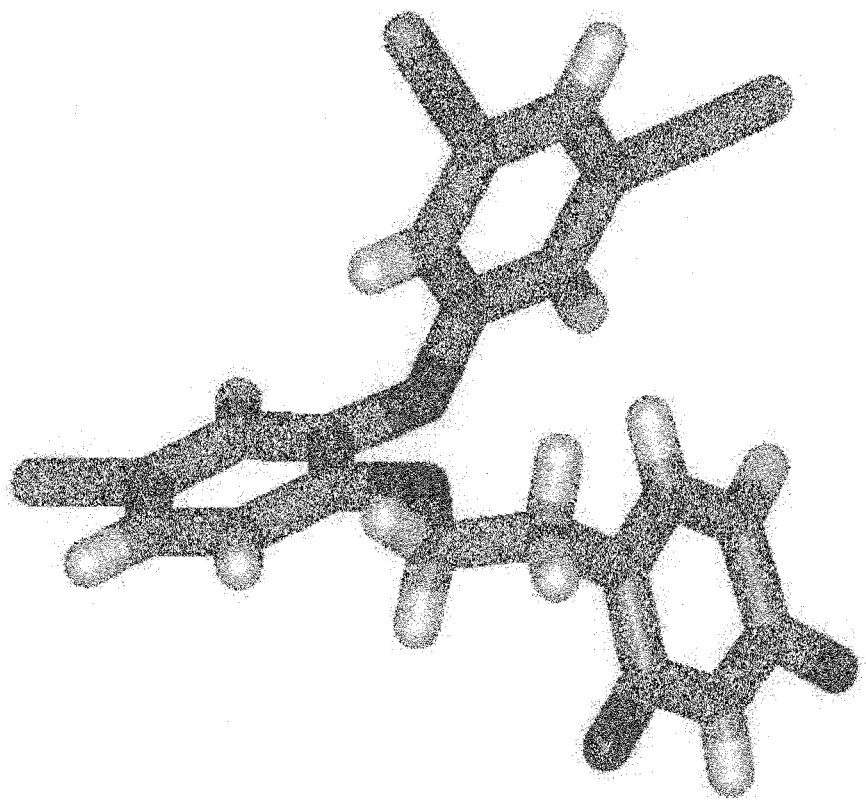
FIG. 2 shows the small molecule crystal structure of compound 20. Details are presented in the experimental section.

As recorded in Table 4, headway was rapidly made. The results for 20-25 show that the 2,5-, 3,5-, and 2,6-substitution patterns for the phenoxy ring all provide active compounds and a chlorine is indeed preferred at the 5' position in the catechol ring over the 4'-alternative. 25 is a potent NNRTI with an EC$_{50}$ of 14 nM, and it has a large safety margin, since no cytotoxicity was observed to the limit of the tested concentration range, 100 μM. The results for 26 and 27 then reconfirm that small substituents at C5 in the uracil ring have little effect. However, potency is dramatically lost by replacement of the 5'-Cl by cyano in 28 and 29. Modeling indicates that the 5'-nitrile nitrogen in the complexes is ca. 3.1 Å from the carbonyl oxygen of Lys101. In addition, if a 5-cyano group in the phenoxy ring is positioned over the catechol ring, there would be dipole-dipole repulsion between the two cyano groups. The situation is strikingly relieved by replacing the phenoxy cyano group with chlorine in progressing to 32, which brings the anti-HIV activity back to 20 nM. The good potency, 43 nM, for the 2,5-dichloro isomer 31 (FIG. 1) is also consistent with the expectations from the FEP results, and the benefit of the second chlorine is apparent in comparison to the results for 30. The difference in performance of the 3-chloro,5-cyanophenoxy substituent depending on the substitution of the catechol ring is notable (22, 25, 28). The spectroscopic characterization of the structures for some of the compounds was also confirmed by crystallography, e.g., for 20 in FIG. 2. It is noted that the conformation of 20 in the crystal lattice is identical to that for the aag conformer of 31 in FIG. 1.

TABLE 4

Anti-HIV-1 Activity (EC$_{50}$) and Cytotoxicity (CC$_{50}$), μM, of Catechol Diether Derivatives

| Compd | R$^1$ | X | Y | R$^{2a}$ | EC$_{50}$ | CC$_{50}$ |
|---|---|---|---|---|---|---|
| 20 | 4-Cl | 3-CN | 5-CN | H | 0.14 | 80 |
| 21 | 4-Cl | 2-Cl | 6-CN | H | 0.12 | 50 |
| 22 | 4-Cl | 3-Cl | 5-CN | H | 0.090 | 33 |
| 23 | 5-Cl | 2-Cl | 5-CN | H | 0.100 | 60 |
| 24 | 5-Cl | 3-CN | 5-CN | H | 0.046 | >100 |
| 25 | 5-Cl | 3-Cl | 5-CN | H | 0.014 | >100 |
| 26 | 5-Cl | 3-Cl | 5-CN | F | 0.013 | 17 |
| 27 | 5-Cl | 3-Cl | 5-CN | Cl | 0.017 | 31 |
| 28 | 5-CN | 3-Cl | 5-CN | H | 6.0 | >100 |
| 29 | 5-CN | 3-Cl | 5-CN | Cl | 5.3 | 94 |
| 30 | 5-CN | 2-Cl | H | H | 0.27 | >100 |
| 31 | 5-CN | 2-Cl | 5-Cl | H | 0.043 | 71 |
| 32 | 5-CN | 3-Cl | 5-Cl | H | 0.020 | >100 |
| 40 | 5-CN | 3-CV | H | H | 0.015 | >100 |
| 41 | 5-Cl | 3-CV | H | H | 0.005 | 19 |
| 42 | 5-Cl | 3-CV | 5-Cl | H | 0.000055 | 10 |
| 43 | 5-NHMe | 3-CV | 5-Cl | H | 0.020 | 30 |
| 44 | 3-F, 5-CN | 2-Cl | H | H | 0.16 | >100 |
| 45 | 3-Cl, 5-Cl | 2-Cl | H | H | 0.83 | 13 |
| 46 | 5-CN | 3-MOEO | H | H | 0.54 | >100 |
| 47 | 5-CN | 3-HOPO | H | H | 1.8 | >100 |
| JLJ505 | 5-Cl | 3-CV | 5-F | H | 0.0032 | >48 |
| JLJ506 | 5-F | 3-CV | 5-F | H | 0.000342 | >45 |
| JLJ510 | — | 3-CV | 5-F | H | 0.000900 | 70 |
| JLJ511 | 5-Br | 3-CV | 5-F | H | 0.00180 | 15 |
| JLJ516 | 5-F | 3-CV | 5-Cl | H | 0.000770 | 62 |
| JLJ518 | 5-Cl | 3-CV | 5-Br | H | 0.0052 | 80 |
| JLJ526 | 5-MPEO | 3-CV | 5-F | H | 0.520 | 27 |
| JLJ530 | 5-MPEO | 3-CV | 5-Cl | H | 1.10 | 100 |
| JLJ531 | 5-Br | 3-CV | 5-Cl | H | 0.0091 | 13 |
| JLJ532 | — | 3-CV | 5-Cl | H | 0.00031 | 18 |

$^a$CV = (E)-cyanovinyl; MOEO = methoxyethoxy; HOPO = 3-hydroxypropan-1-oxy; MPEO = N-morpholinylethoxy.

At this point, consideration was given to possible replacement of the uracil group and/or variation of the linking chain. Though multiple options were tried, none emerged as competitive with the uracilylethoxy substituent. For example, 33, the 4-pyridinyl analog of 31, was synthesized and found to worsen the EC$_{50}$ value 18-fold to 0.76 μM. The isomer 34 with the methylenoxymethyl linker was significantly less potent still (12 μM), and shortening the linker to OCH$_2$ in 35 also did not improve the activity (1.8 μM). The methylenoxymethyl linker was not tried with the uracil group owing to the lability of the hemiaminal substructure. The 3-pyridinyl-, 2,4-pyrimidinyl-, 5-pyrazolyl-, 5-oxazolyl-, and 4-pyridinyl-N-oxide-analogs of 34 also showed no activity below μM-levels.

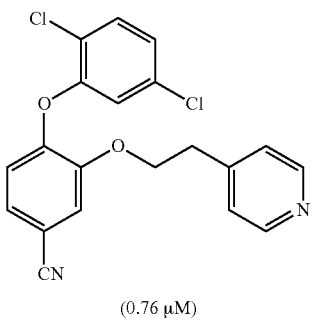

33

(0.76 μM)

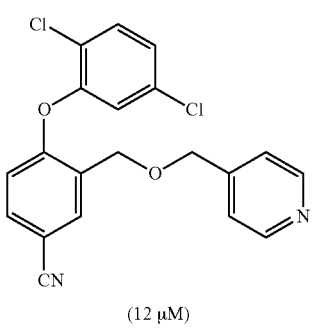

34

(12 μM)

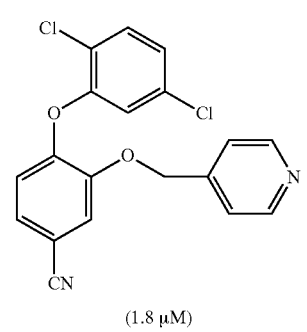

35

(1.8 μM)

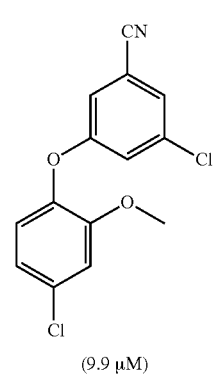

36

(9.9 μM)

Thus, the transfer of parts of a potent inhibitor to a less potent one, e.g., the methyleneoxymethyl linker of 2 to 33 or 35, is an undependable strategy.[26] Conformational differences are affected by the rest of the structures. For the present catechol derivatives, in conformational searches using OPLS-AA for 2-ethoxyanisole, the aa and ga conformers for the ethoxy group are the lowest in energy; they correspond to the conformers in FIG. 1. For 2-methoxymethylanisole, the corresponding ga conformer is not an energy minimum; it collapses to aa. Finally, the importance of the uracilylmethyl group was clearly demonstrated through the preparation of 36, whose $EC_{50}$ of 9.9 μM can be compared to the 14 nM for 25. The benefits of additional van der Waals interactions and the hydrogen bond between Lys103 and the uracilyl NH are likely contributors. Thus, deletion of the uracil, which might be suggested by considering emivirine (4), is detrimental.

By this juncture, some results on the activity of the more potent compounds towards variant strains of HIV-1 containing the Tyr181Cys mutation and the challenging Lys103Asn/Tyr181Cys double mutation in HIV-RT had been obtained (Table 5). Optimism might be justified from the general topological similarities of 3 and the present catechol diethers and the fact that 3 is reported to show <10 nM activity towards WT HIV-1 and many variants including Y181C and K103N/Y181C.[8] However, the catechol diethers through compound 32 are not as potent against WT HIV-1 as 3 (2 nM), and the performance against the Y181C variant and double mutant was also found to be diminished (Table 5). The best compound at this point was 27, which has $EC_{50}$ values of 17, 240, and 570 nM towards WT, Y181C, and the K103N/Y181C variants. The 14- and 34-fold ratios between the variant and WT activities are better than typical,[24] so it seemed that a prerequisite for further improvement was to drive down the WT $EC_{50}$ by another factor of 10 or more.

TABLE 5

Anti-HIV Activity ($EC_{50}$) and Average Cytotoxicity ($CC_{50}$), μM, of Catechol Diether Derivatives and Reference NNRTIs for WT and Viral Variants.

| | $EC_{50}$ | | | |
|---|---|---|---|---|
| Compd | WT | Y181C | K103N/Y181C | $CC_{50}$ |
| 20 | 0.14 | 21 | 2.2 | 77 |
| 22 | 0.090 | 6.7 | 1.2 | 32 |
| 25 | 0.014 | 0.52 | 1.7 | >100 |
| 26 | 0.013 | 0.62 | 1.7 | 13 |
| 27 | 0.017 | 0.24 | 0.57 | 21 |
| 31 | 0.043 | 0.92 | 2.8 | 59 |
| 32 | 0.020 | 0.80 | >43 | >61 |
| 40 | 0.015 | 0.98 | 8.0 | >90 |
| 41 | 0.005 | 0.37 | 1.6 | 22 |
| 42 | 0.000055 | 0.049 | 0.22 | 10 |
| 43 | 0.020 | 2.8 | | 30 |
| JLJ505 | 0.0032 | 0.150 | 0.9 | 48 |
| JLJ506 | 0.000342 | 0.016 | 0.085 | 45 |
| JLJ510 | 0.00090 | 0.080 | 0.075 | 85 |
| JLJ516 | 0.00077 | 0.060 | 0.25 | 63 |
| JLJ532 | 0.00031 | 0.046 | 0.024 | 11 |
| efavirenz | 0.002 | 0.010 | 0.030 | 15 |
| efavirenz[a] | 0.0014 | 0.002 | 0.037 | |
| etravirine | 0.001 | 0.008 | 0.005 | 11 |
| etravirine[a] | 0.001 | 0.007 | 0.004 | |
| rilpivirine | 0.00067 | 0.00065 | 0.002 | >1 |
| rilpivirine[a] | 0.0004 | 0.0013 | 0.001 | 8 |

[a]Literature data; see ref. 28.

Cyanovinyl Analogs.

Figure 3:
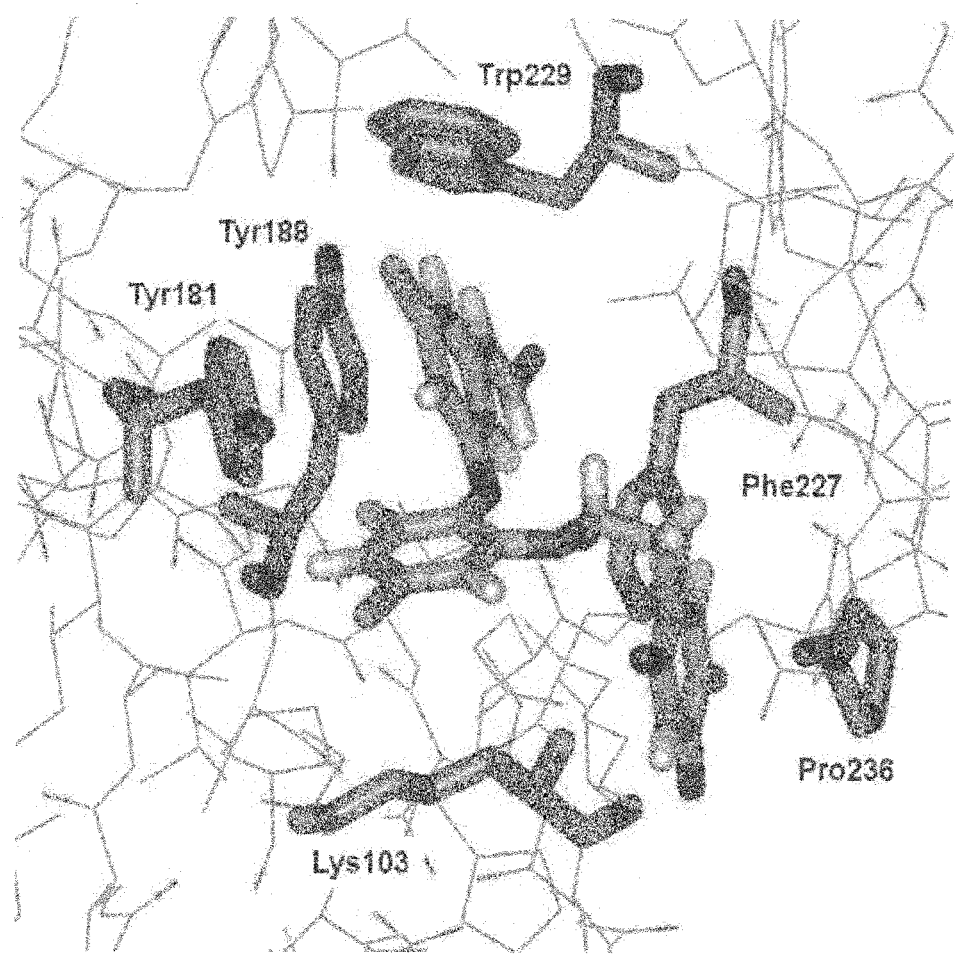
FIG. 3 shows the computed structure of 42 (JLJ0494) bound to HIV-RT illustrating the positioning of the cyanovinyl group between Tyr188 and Phe227. Carbon atoms of 42 are lighter in color.

To this end, introduction of a cyanovinyl group in the terminal phenyl ring was considered. This had proved profitable in another series, which included 37,[27] and it also finds precedent in R165481 (38)[8] and rilpivirine (39).[28] All three of these cyanovinyl containing NNRTIs have activities below 5 nM for both WT HIV-1 and the Y181C-containing variant. However, in view of the caveats above concerning the methylenoxymethyl linker and uracil, modeling was carried out, which did indicate that a m-cyanovinyl group could be incorporated in the current series (FIG. 3). It should make favorable van der Waals contact

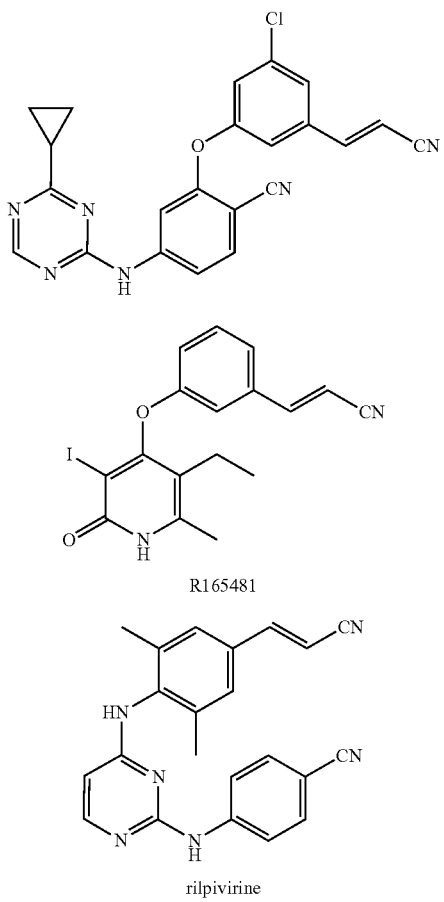

R165481 rilpivirine with Trp229 and be positioned between Tyr188 and Phe227, as is observed in the crystal structures for the complexes of 38 and 39.[8,28]

Thus, continuing from 32 in Table 4, the 3-cyanovinyl analog 40 was prepared and showed improved activity at 15 nM. Switching to chlorine instead of cyano at the 5-position in the catechol ring brought an expected further enhancement, specifically, to 5 nM for 41. Then, for reintroduction of a chlorine in the phenoxy ring, the 4-, 5-, and 6-Cl isomers were considered with the cyanovinyl group at the 3-position. Energy minimizations for the complexes of the three alternatives indicated a preference for substitution at C5 or C6 based on the protein-ligand interaction energies of −70.0, −73.9, and −73.1 kcal/mol. The interaction energy for the reference compound 41 is −71.4 kcal/mol. The 4-chlorine leads to a steric clash with Trp229, while the 5-chlorine projects into a pocket formed by Pro95, Pro97, Leu100, and Tyr181, and the 6-chlorine nuzzles between Leu100 and Tyr181. However, for the C5 and C6 options, evaluation of the conformational energetics suggests more ligand strain for the C6 isomer owing to the placement of the 6-Cl over the catechol ring. In view of the interaction energy improvement for addition of the 5-chlorine and the anticipated benefits of burial of more hydrophobic surface area, a significant activity boost was expected.

Thus, synthesis of the 3-cyanovinyl, 5-Cl analog 42 was carried out and the activity results were gratifying. It is an extraordinarily potent NNRTI. The initial WT assay yielded an $EC_{50}$ of 24 pM. To our knowledge, this is the lowest $EC_{50}$ for an NNRTI that has been reported; the next most potent NNRTI appears to be 39.[28] 42 was re-assayed side-by-side with 39 yielding $EC_{50}$s of 55 and 670 pM, which are the values reported in Table 5. A 5- or 6-substituent in the phenoxy ring is also expected to help fill the space vacated upon mutation of Tyr181 to cysteine. This notion and the benefits of the improved activity for the cyanovinyl-containing inhibitors yielded $EC_{50}$ values for 42 of 49 and 220 nM for the variant HIV-1 strains containing the Y181C and K103N/Y181C mutations (Table 5).

Table 5 includes data for four approved drugs with results from both our measurements using infected MT2 cells and those of Janssen et al. using MT4 cells;[28] the directly comparable results are almost all within a factor of 2. In comparison to the approved drugs in Table 5, 42 is by far the most potent towards the wild-type virus. It also shows good potency towards the two mutant strains, though not at the low-nanomolar levels of rilpivirine (39). With a therapeutic index >180,000, the relatively low cytotoxicity, $CC_{50}$, towards human T-cells of many of the present compounds compared to the most potent drugs is also notable.

Figure 4:
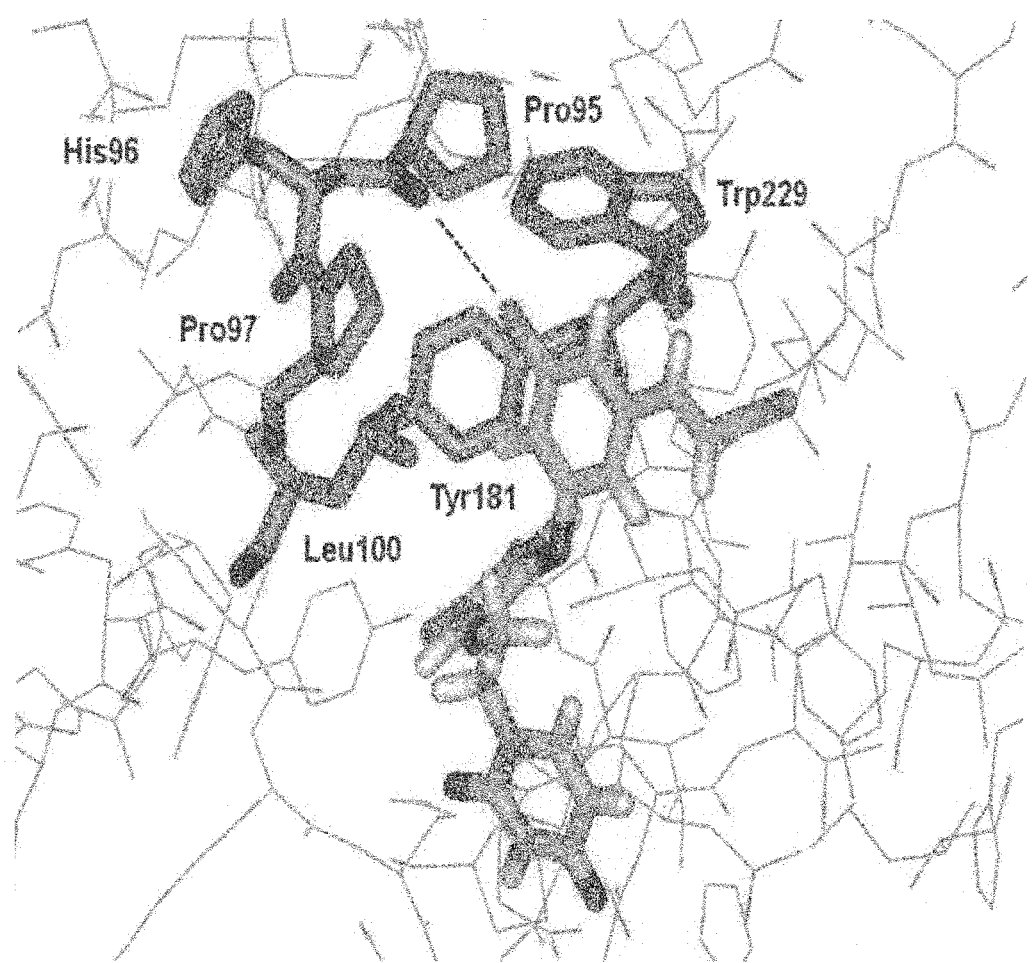
FIG. 4 shows the computed structure of 42 bound to HIV-RT illustrating the positioning of the 5-chlorine in the terminal phenyl ring of the inhibitor near the oxygen atom of Pro95.

The computed structure for the complex of 42 (FIG. 3) indicates that 42 fills the space extremely well in the channels running from Tyr181 past Trp229 and towards Phe227 and Pro236. The hydrogen bond with the carbonyl group of Lys103 remains notable. Furthermore, there may also be a boost for a halogen bond between the 5-Cl and the carbonyl oxygen of Pro95.[29] This is illustrated in FIG. 4, though standard force fields including OPLS do not account for the benefits of halogen bonding.[30] The simple point-charge model with a partial negative charge on chlorine is inadequate to describe correctly the electrostatic field along the C—Cl bond axis.[29] Nevertheless, the present, computed O—Cl distance of 3.43 Å is near the ideal value of ca. 3.3 Å for such interactions.[29,30] It may be noted that when the complex is reoptimized with the only change being replacement of the cyanovinyl group in 42 by chloro or cyano, the O—Cl distance increases to 3.62 and 3.72 Å, respectively. The shift towards Pro95 for 42 improves the contact between the first methine unit of the vinyl group and Trp229. Thus, the optimal halogen bonding likely requires both the 3-chloro and 5-cyanovinyl groups. Notably, a recent report on inhibition of cathepsin L also found large binding enhancements upon introduction of a halogen bond between a halophenyl group of the inhibitors and a backbone carbonyl group.[31] In comparison to the unsubstituted case, introduction of a halogen bond with chlorine, bromine, and iodine enhanced the binding by factors as large as 24, 49, and 74, respectively.[31]

A few additional compounds were synthesized. (1) The analog of 42 with a methylamino group at C5 in the catechol ring, 43, is much less active (20 nM). Though it might benefit from a favorable electrostatic interaction between the amino group and the carbonyl of Lys101, the dehydration penalty would be greater than for 42. (2) Returning to 2 and 3, one might be motivated to include a substituent at the 3-position in the catechol ring, though the FEP results noted above indicated that substitution at that site with chlorine would be the least beneficial of the four possibilities. Addition of the 3-fluoro group in 44 (0.16 μM) was found to provide slight improvement over the results for 30 (0.27 μM), while the 3-chlorine in 45 (0.83 μM) was detrimental, since the reference compound would be expected to be more potent than 30. In this case, the reason why the mapping from the precedents fails is likely associated with the fact that 2 and 3 both form a hydrogen bond with their NH groups and the carbonyl of Lys101. As the 5-Cl or 5-CN in 44 or 45 aligns with the NH, the present compounds are pushed away and rotated from Lys101, which changes the positioning of the catechol ring versus the central rings in 2 and 3. (3) As the region behind Tyr188, Phe227, and Trp229 in FIG. 3 opens into a solvent filled channel heading towards the polymerase active site, replacement of the (E)-cyanovinyl group with longer chains that could extend into this region was explored. In comparison to 40, 46 with a methoxyethoxy substituent was found to retain significant activity (0.54 μM), while the more hydrophilic hydroxypropoxy alternative in 47 diminishes the activity to 1.8 μM.

Other Diarylethers, Comparison with Prior Art.

While this work was in progress, reports of other NNRTIs with diarylether substructures appeared from Merck and Roche.[32,33] The illustrated 72 and 73 appear to be the most promising compounds from these efforts. They are clearly far more similar to each

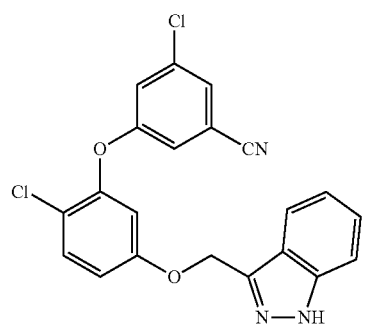

72

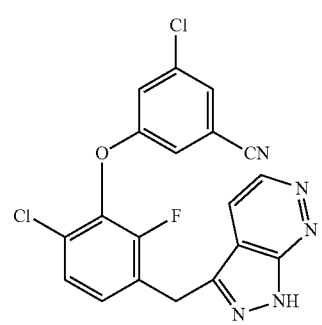

73 other than to 42. Notably, the central benzene ring in 72 and 73 is 1,3-disubstituted with the aryl appendages, while in 42 it is 1,2-disubstituted. The lengths of the linkers to the heteroaryl group in the three compounds are also different, the heterocycle is a monocyle in 42, the cyanovinyl group is unique to 42, and 72 and 73 have a chlorine adjacent to the phenoxy oxygen, which was not found to be desirable in the present series (e.g., 45). 72 is reported to have anti-HIV activities in cell assays of 4.7, 13.8, and 141 nM for the WT, Y181C, and K103N/Y181C variants,[31] while the corresponding values for 73 are 1, 1, and 4 nM.[33a] Thus, these compounds are also much less potent towards wild-type HIV-1 than 42, while 73 has the best results for the mutant strains.

Tetracyclic Analogues

Sub-Genus Structure

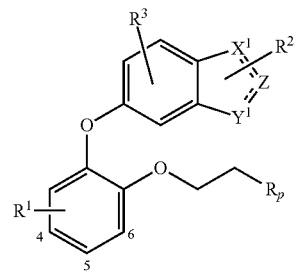

The following tetracyclic compounds were synthesized and tested for anti-HIV activity (WT-HIV-1) and cytotoxicity (as described above). The results are presented in Table 6, below. Synthesis of the tetracyclic compounds is also presented below generally and in the attached synthetic schemes which are presented in FIGS. 6-9.

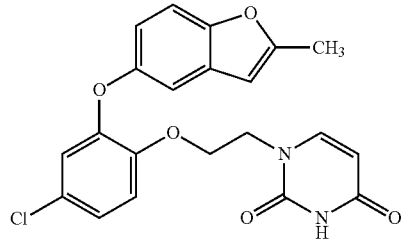

JLJ538

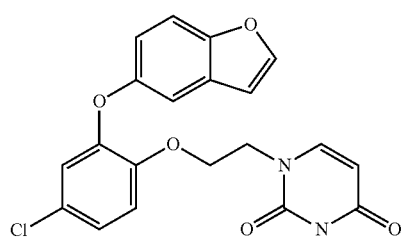

JLJ539

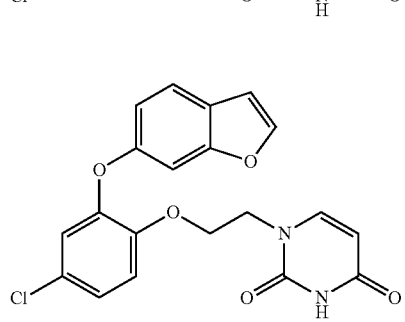

JLJ552

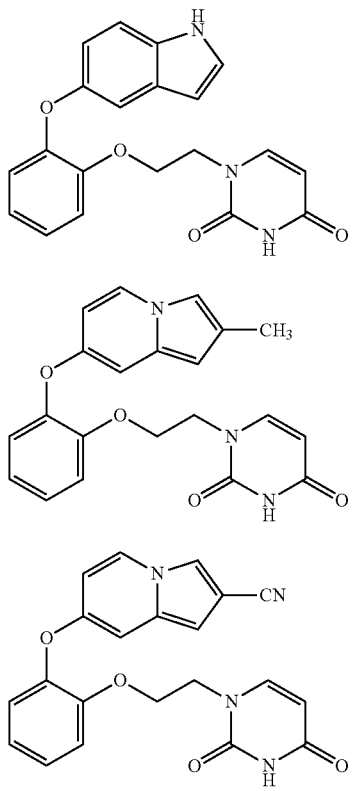

TABLE 6

Anti-HIV Activity (EC$_{50}$) and Average Cytotoxicity (CC$_{50}$), μM, of Tetracyclic Analogues for WT HIV-1.

| Compd  | EC$_{50}$ | CC$_{50}$ |
|--------|-----------|-----------|
| JLJ538 | 0.025     | 8         |
| JLJ539 | 0.800     | 19        |
| JLJ552 | 0.900     | 50        |
| JLJ547 | 0.085     | 53        |
| JLJ550 | 0.050     | 9         |
| JLJ555 | 0.00038   | >100      |

Of the above-compounds, the indole JLJ547 and the indolizine JLJ555 appear to be the compounds with the best activity. JL555, the cyano-substituted indolizine is particularly active in vitro against HIV-1 as indicated in Table 6. We proceeded with MC/FEP calculations for a variety of bicyclic heterocycles, and were led to focus on the illustrated compounds with very high expectations for JLJ555. Apparently, the cyanoindolizine mimics the cyanovinylphenyl group of JLJ494 (42), JLJ532, etc., but it eliminates potential concerns for unwanted Michael additions to the cyanovinyl group, which could lead to toxicities in certain instances.

The inventors also have obtained crystal structures for JLJ494 and JLJ506 bound to HIV-1 reverse transcriptase. The crystal structures are in good accord with the previous structural analyses based on the computed structures. These three dimensional structures confirm the importance of key protein interactions including the conserved residues Pro95 and Trp229. Earlier literature has established the importance of Trp229 as important catalytic residue.[34] Pro95 is also interesting as it has never been found as a drug resistance mutation[35] however our recent data shows it also is essential for enzyme catalysis (Mislak, unpublished data).

Chemical Synthesis of Tetracyclic Compounds

Figure 5:
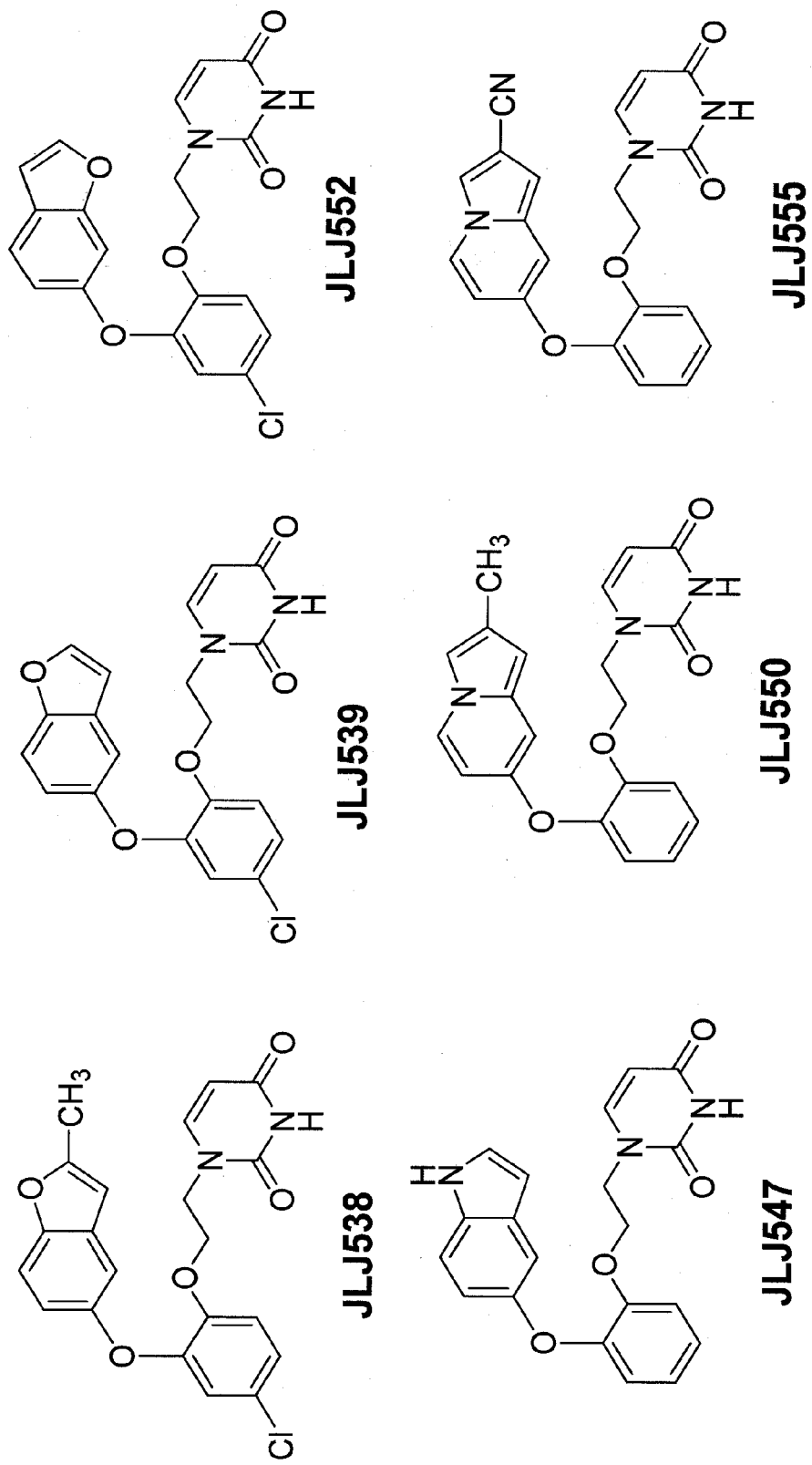
FIG. 5 shows specific exemplary tetracyclic compounds of the present invention.
Figure 6A:
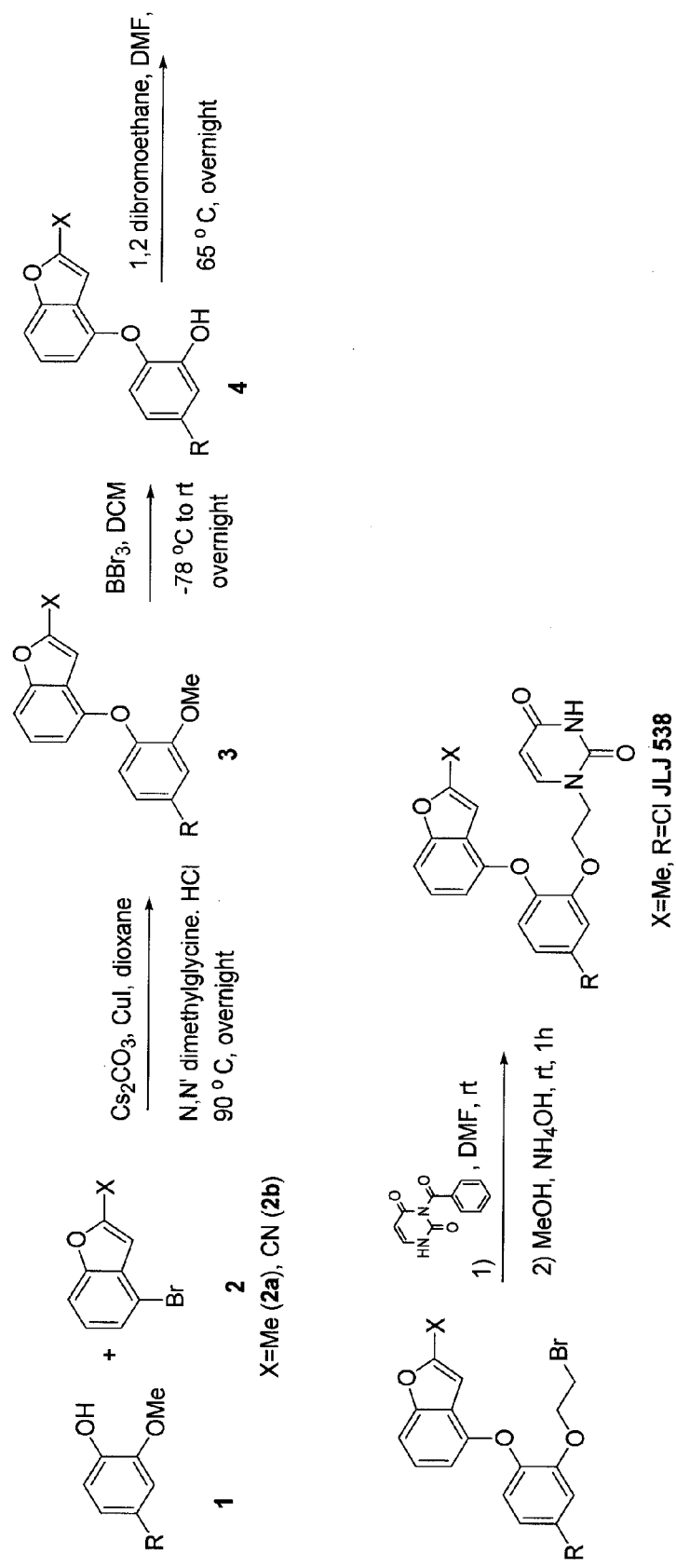
FIG. 6A shows the chemical synthesis of JLJ538 as indicated from starting materials 1 and 2a and 2b to produce the final tetracyclic compound.
Figure 6B:
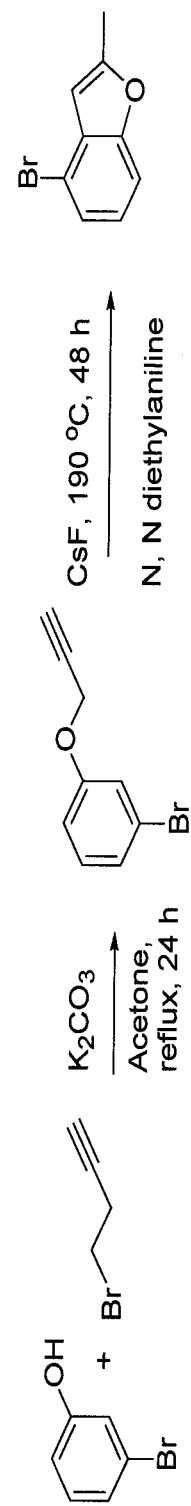
FIG. 6B shows the synthesis of intermediate 2a which is a methyl substituted benzodihydrofuran from the halogenated anisole starting material.

The tetracyclic compounds which are set forth above and in FIG. 5, and above, are synthesized pursuant to the synthetic methods presented in FIGS. 6-9. In particular, JLJ538 which is a tetracyclic compound containing a benzofuran ring is synthesized from the methoxy-substituted phenol starting material and benzofuran starting material (2a, 2b). See FIGS. 6a, 6b. The starting material is reacted to condense the phenolic hydroxyl group onto the benzofuran starting material at the substituted bromine position to provide intermediate 3. Intermediate 3 is demethylated to provide intermediate 4 which is reacted with 1,2 dibromoethane in solvent (DMF) to provide the bromoethyl ether intermediate which is condensed with a uracil derivative and deprotected to provide final compound JLJ538. Using this same approach, a large number of tetracyclic compounds containing a benzofuran or substituted-benzofuran may be readily synthesized.

Figure 7:
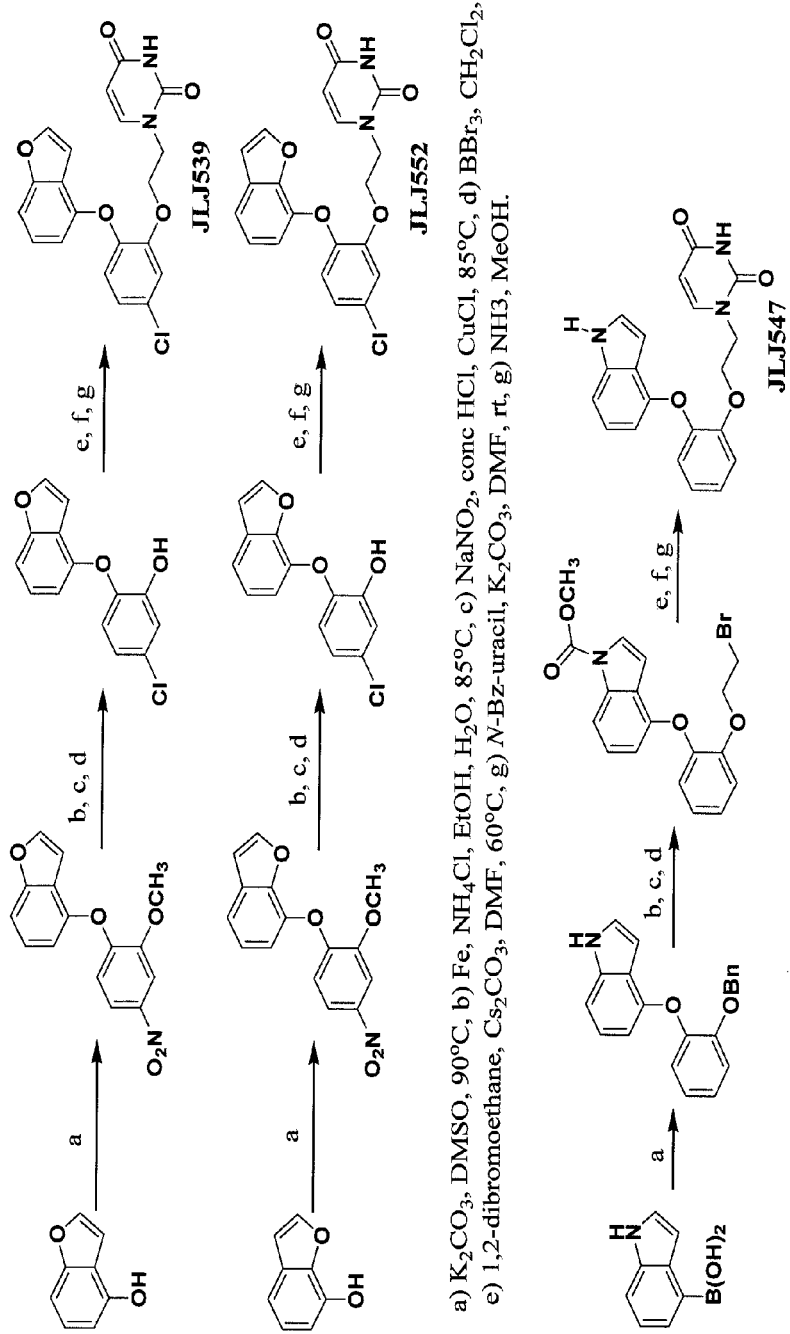
FIG. 7 shows the chemical synthesis of JLJ 539, JLJ552 and JLJ547 which are presented in attached FIG. 5. The reactants used in the chemical synthesis for each chemical are identified in the figure.
Figure 8:
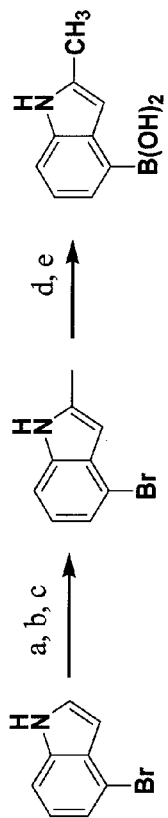
FIG. 8 shows an alternative synthesis for JLJ547 (attached FIG. 5) and its derivatives starting with modified starting material (substituted indole starting material).
Figure 8:
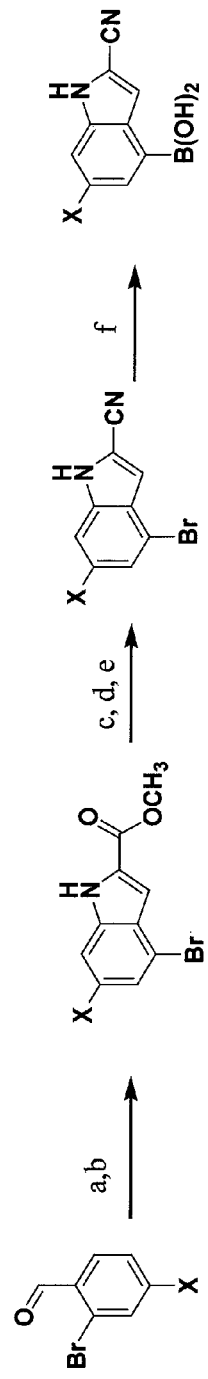
Figure 9A:
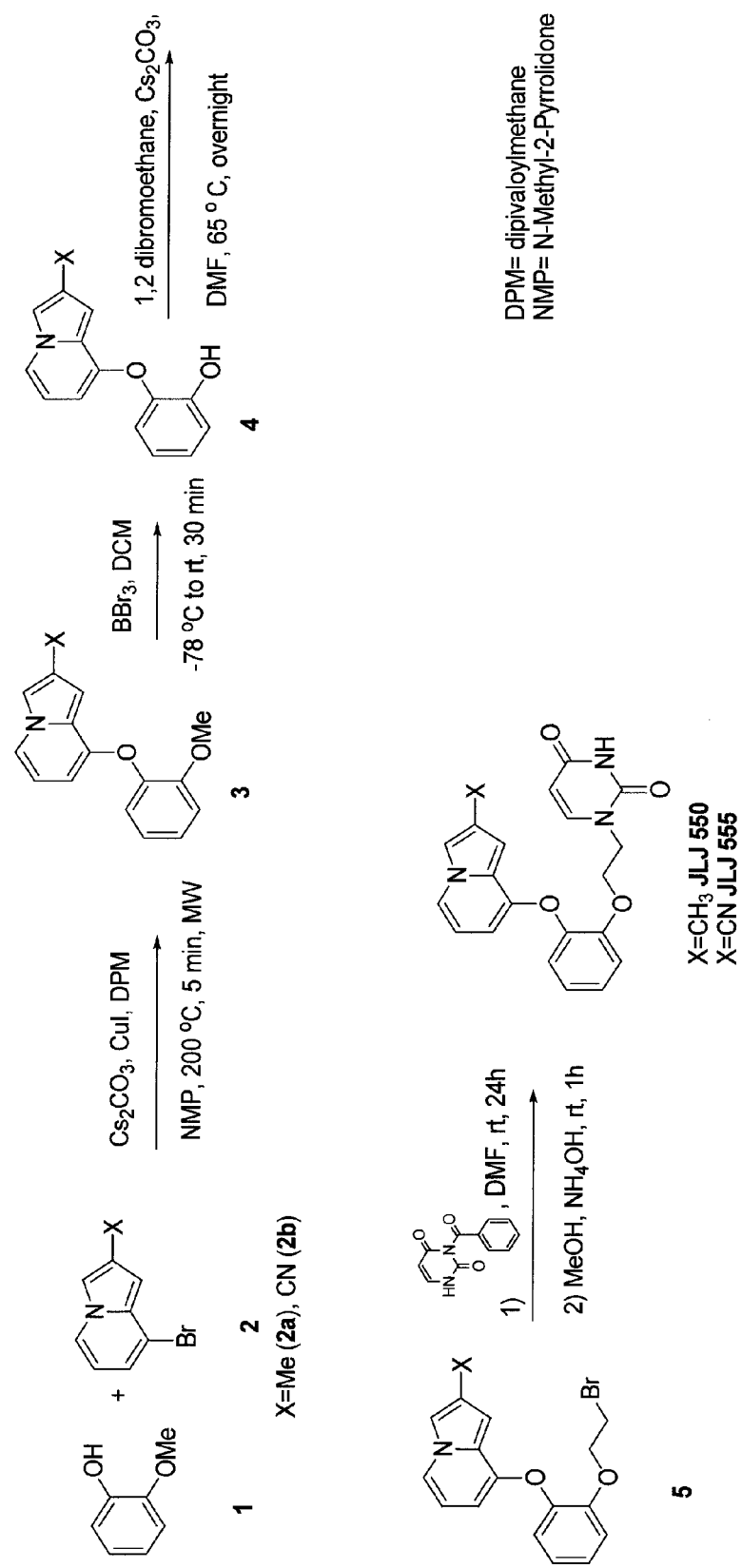
FIG. 9A shows a synthetic scheme for JLJ550 and JLJ555 (attached FIG. 5) and its derivatives.
Figure 9B:
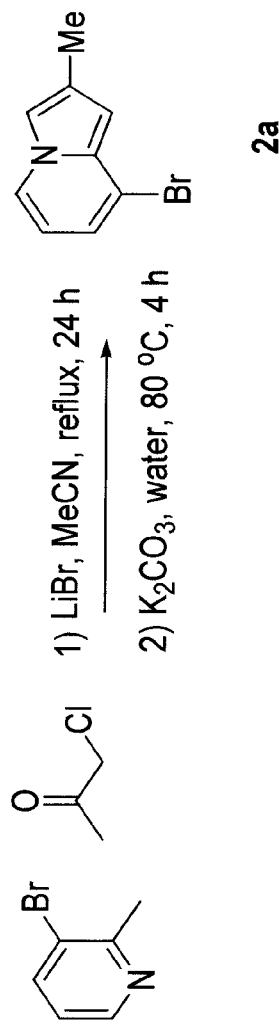
FIG. 9B shows the synthesis of intermediates 2a and 2b which are methyl and cyano-substituted benzopyrrole (indolizine) derivatives.
Figure 9B:
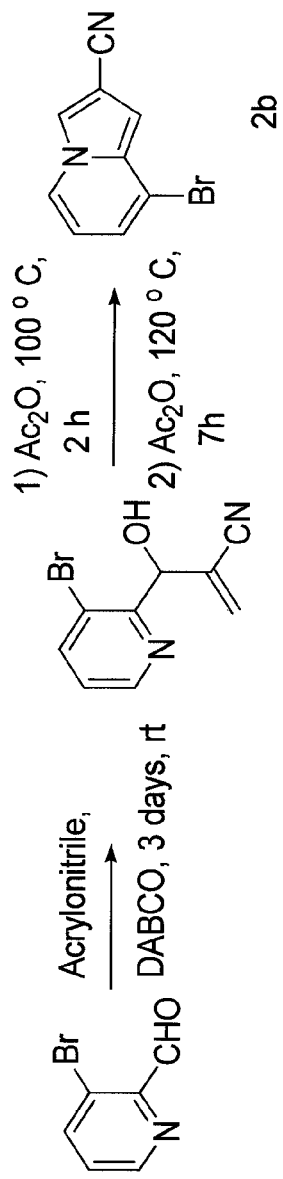

In the case of JLJ539, JLJ552 and JLJ547, these compounds are synthesized pursuant to the scheme which is set forth in FIG. 7. Briefly, the hydroxyl-substituted benzofuran is reacted with a halogen-substituted nitroanisole compound to afford a tricyclic intermediate which is further derivatized to produce the tricyclic chlorophenol benzofuran intermediate which is subsequently further derivatived with a uracil derivative and deprotected to produce JLJ539. JLJ552 is similarly produced starting with an isomeric benzofuran. JLJ547, an indole derivative, is synthesized from the starting indole (similar to 2a and 2b, which are prepared pursuant to the reaction scheme of FIG. 8) containing a boronic acid group which undergoes a Suzuki reaction to produce the benzoyl protected tricyclic compound, which undergoes a series of steps, one of which is the protection of the indole amine, etherification and introduction of a uracil group as indicated to produce JLJ547. Related substituted indole compounds are prepared pursuant to the similar approach set forth in FIGS. 7 and 8. Compounds JLJ550 and JLJ555 (each containing a substituted indolizine group) are synthesized pursuant to the chemical scheme which is presented in FIG. 9A. The synthesis is analogous to the synthesis of the other tetracyclic compounds identified. The substituted indolizine starting materials for these compounds is prepared pursuant to the approach presented in FIG. 9B hereof.

Conclusion

In summary, the present closely-coupled experimental and computational efforts began with virtual screening, which led to the intriguing core structure 1 starting from the crystal structures of 2 and 3. Though the anti-HIV activity of 1 was modest, 5 μM, with the aid of the computational analyses especially MC/FEP results, it was possible to evolve 1 into the 55-pM anti-HIV agent 42 (Scheme 5). Key advances included recognition of optimal substitution patterns for the terminal phenyl ring, and the benefits of progressing to the catechol diether core, placement of a substituent at the 5-position in the catechol ring, and introduction of a cyanovinyl group in the terminal phenyl ring. Along the way examples were provided where false assumptions could be made about expected gains from precedents such as transferability of the methylenoxymethyl linker from 2, deletion of the terminal heterocycle as in 4, or addition of a halogen adjacent to the phenoxy ring as in 3. When a change as large as replacement of a central pyridinone ring by a benzene ring is made, optimization must start afresh without assumptions of fragment transferability from active precedents. Further evolution of 42 has included crystallographic investigations and preparation of analogues to tune physical properties and activity towards variant strains of HIV-1.
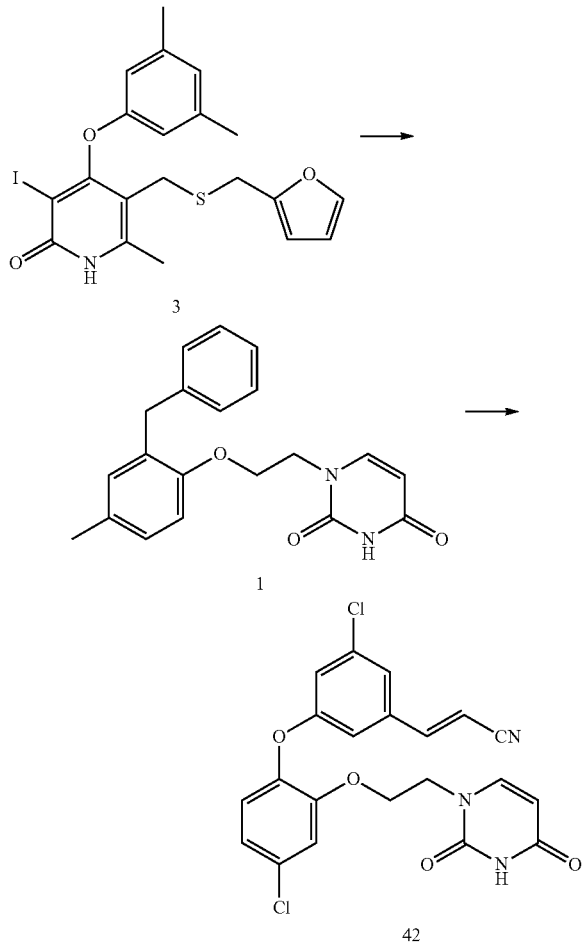

Scheme 5

3

1

42

Further Examples

Reference Section 2 Applies

Chemical Synthetic Procedures

General Information

NMR spectra were recorded on a Bruker Avance DRX-500 (500 MHz) and DRX-400 (400 MHz) instruments. Column chromatography was carried out using CombiFlash over redisep column cartridges employing Merck silica gel (Kieselgel 60, 63-200 μm). Precoated silica gel plates F-254 were used for thin-layer analytical chromatography. Mass determination were performed using electrospray ionization on water Micromass ZQ (LRMS). HRMS (ESI-TOF) analyses were performed on Waters Xevo QTOF equipped with Z-spray electrospray ionization source. The purity (≥95%) of all final synthesized compounds was determined by reverse phase HPLC, using a Waters 2487 dual λ absorbance detector with a Waters 1525 binary pump and a Phenomenex Luna 5μ, C18(2) 250×4.6 mm column. Samples were run at 1 mL/min using gradient mixtures of 5-100% of water with 0.1% trifluoroacetic acid (TFA) (A) and 10:1 acetonitrile: water with 0.1% TFA (B) for 22 min followed by 3 min at 100% B.

Representative Synthesis of Compounds 5-15

Step 1

Diisopropyl azodicarboxylate (DIAD, 5.0 mmol) was added slowly to a solution of o-arylphenols (48 a-h) (4.6 mmol)[1a, 2a] and triphenylphosphine (5.0 mmol) in THF (10.0 mL) at room temperature. After stirring the reaction mixture for 10 minutes, 2-bromoethanol (0.35 mL, 5.0 mmol) was added to it and the resulting mixture was stirred at room temperature for 24 h. After completion, the reaction mixture was concentrated under reduced pressure and purified by column chromatography ($SiO_2$, hexane/EtOAc 80:20) to give 49 a-h 2-benzyl-1-(2-bromoethoxy)-4-chlorobenzene (49 a)

(1.2 g, 67%) $^1$H NMR (500 MHz, $CDCl_3$) δ 7.15 (s, 1H), 7.14 (dd, J=2.0, 8.1 Hz, 1H), 7.12 (dd, J=2.1, 8.3 Hz, 1H), 7.04 (d, J=7.9 Hz, 1H), 6.96 (d, J=2.5 Hz, 1H), 6.76 (d, J=2.1 Hz, 1H), 4.46 (t, J=4.7 Hz, 2H), 4.03 (s, 2H), 3.60 (t, J=4.7 Hz, 2H). $^{13}$C NMR (126 MHz, $CDCl_3$) δ 154.48, 136.07, 132.63, 130.31, 129.75, 129.20, 127.50, 127.02, 126.50, 116.02, 112.59, 68.23, 32.81, 29.01.

1-(2-bromoethoxy)-4-chloro-2-(2-chlorobenzyl)benzene (49 b)

(0.63 g, 35%) $^1$H NMR (500 MHz, $CDCl_3$) δ 7.39-7.32 (m, 1H), 7.21-7.09 (m, 4H), 6.99 (d, J=2.47 Hz, 1H), 6.74-6.67 (m, 1H), 4.23 (td, J=1.85, 6.14 Hz, 2H), 4.06 (s, 2H), 3.56 (td, J=1.94, 6.14 Hz, 2H). $^{13}$C NMR (126 MHz, $CDCl_3$) δ 154.52, 137.37, 134.28, 131.03, 130.44, 130.29, 129.48, 127.73, 127.25, 126.75, 126.13, 112.67, 68.31, 33.23, 28.96.

1-(2-bromoethoxy)-4-chloro-2-(3-chlorobenzyl)benzene (48 c)

(0.7 g, 39%) $^1$H NMR (500 MHz, $CDCl_3$) δ 7.35-7.16 (m, 5H), 6.85 (m, 1H), 6.74-6.60 (m, 1H), 4.23 (t, J=4.14 Hz, 2H), 3.92 (s, 2H), 3.62 (t, J=4.14 Hz, 2H). $^{13}$C NMR (126 MHz, $CDCl_3$) δ 154.37, 142.07, 134.08, 131.12, 130.39, 129.57, 129.45, 129.04, 127.45, 126.75, 112.71, 68.13, 35.74, 29.08.

1-(2-bromoethoxy)-4-chloro-2-(2,4-dichlorobenzyl)benzene (48 d)

(1.5 g, 67%) $^1$H NMR (500 MHz, $CDCl_3$) δ 7.42 (s, 1H), 7.15-7.13 (m, 2H), 7.08 (d, J=2.47 Hz, 1H), 6.94-6.83 (m, 1H), 6.75 (d, J=2.47 Hz, 1H), 4.26 (t, J=4.14 Hz, 2H), 4.03 (s, 2H), 3.61 (t, J=4.14 Hz, 2H). $^{13}$C NMR (126 MHz, $CDCl_3$) δ 154.46, 136.05, 134.80, 131.77, 130.31, 129.75, 129.24, 127.50, 127.02, 126.14, 112.53, 68.23, 32.84, 29.01.

1-(2-bromoethoxy)-4-chloro-2-(3,5-dichlorobenzyl)benzene (48 e)

(0.45 g, 22%) $^1$H NMR (500 MHz, $CDCl_3$) δ 7.22-7.15 (m, 5H), 6.75 (m, 1H), 4.22 (td, J=1.99, 6.00 Hz), 3.87 (s, 2H), 3.61 (d, J=6.00 Hz, 2H). $^{13}$C NMR (126 MHz, $CDCl_3$) δ 154.31, 143.42, 134.64, 130.40, 130.31, 127.78, 127.50, 126.34, 126.12, 112.64, 68.07, 35.64, 29.08.

1-(2-bromoethoxy)-4-chloro-2-(2,5-dichlorobenzyl)benzene (48 f)

(1.26 g, 64%) $^1$H NMR (400 MHz, CDCl$_3$) δ 7.26 (d, J=8.47 Hz, 1H), 7.18-6.96 (m, 4H), 6.70 (d, J=8.70 Hz, 1H), 4.21 (t, J=5.92 Hz, 2H), 4.01 (s, 2H), 3.57 (t, J=5.94 Hz, 2H). $^{13}$C NMR (101 MHz, CDCl$_3$) δ 159.91, 154.45, 139.19, 132.45, 132.41, 130.81, 130.44, 129.24, 127.70, 127.62, 126.04, 112.54, 68.12, 33.36, 29.01.

2-(2-(2-bromoethoxy)-5-chlorobenzyl)-1,3-dichlorobenzene (48g)

(1.05 g, 53%) $^1$H NMR (500 MHz, CDCl$_3$) δ 7.35 (dd, J=3.02, 8.04 Hz, 2H), 7.20-7.03 (m, 2H), 6.77 (dd, J=3.08, 8.67 Hz, 1H), 6.56 (d, J=2.55 Hz, 1H), 4.50-4.15 (m, 4H), 3.69 (td, J=3.07, 6.10 Hz, 2H). $^{13}$C NMR (126 MHz, CDCl$_3$) δ 154.35, 136.41, 135.32, 128.95, 128.51, 128.36, 127.97, 126.97, 126.26, 112.47, 68.40, 30.75, 29.06.

2-(2-bromoethoxy)-4-chloro-1-(2-chlorobenzyl)benzene (48 h)

(2.3 g, 78%) $^1$H NMR (500 MHz, CDCl$_3$) δ 7.41-7.29 (m, 1H), 7.13-7.08 (m, 2H), 6.95 (dd, J=5.18, 7.73 Hz, 1H), 6.91-6.85 (m, 1H), 6.83-6.79 (m, 1H), 6.75 (t, J=10.48 Hz, 1H), 4.24 (t, J=5.93 Hz, 2H), 4.07 (dd, J=8.13, 10.84 Hz, 2H), 3.62-3.53 (m, 2H). $^{13}$C NMR (126 MHz, CDCl$_3$) δ 154.36, 138.16, 133.24, 131.46, 129.88, 129.84, 128.08, 127.98, 127.52, 127.16, 121.65, 112.65, 68.65, 33.52, 29.27.

Step 2

A solution of uracil (0.3 g, 2.7 mmol) and ammonium chloride (0.03 g, 0.6 mmol) in hexamethyldisilazane (5.0 mL) was refluxed for 4 h under N$_2$ atmosphere. The reaction mixture was allowed to cool to room temperature; excess of hexamethyldisilazane was removed under reduced pressure. To this crude of 49 a-h (0.9 mmol) was added and the resulting mixture was heated at 180° C. in an oil bath for 1.5 h under nitrogen atmosphere[3a]. Reaction mixture was cooled to room temperature and then diluted with ethyl acetate (5.0 mL) and few drops of ethanol. This turbid solution was directly loaded on silica column and purified with 5-7% methanol/dichloromethane to give 5-15.

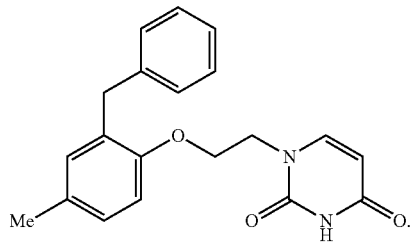 [SMILES: Cc1ccc(OCCn2ccc(=O)[nH]c2=O)c(Cc2ccccc2)c1]

1-(2-(2-benzyl-4-methylphenoxy)ethyl)pyrimidine-2,4(1H,3H)-dione (1)[4a]

$^1$H NMR (500 MHz, CDCl$_3$) δ 9.14 (s, 1H), 7.28-7.23 (m, 2H), 7.19 (t, J=7.3 Hz, 1H), 7.08 (d, J=7.0 Hz, 2H), 7.00 (dd, J=1.8, 8.3 Hz, 1H), 6.93 (d, J=1.9 Hz, 1H), 6.88 (d, J=7.9 Hz, 1H), 6.72 (d, J=8.3 Hz, 1H), 5.41 (dd, J=1.9, 7.9 Hz, 1H), 4.14 (t, J=4.1 Hz, 2H), 4.00 (t, J=4.0 Hz, 2H), 3.92 (s, 2H), 2.25 (s, 3H). $^{13}$C NMR (126 MHz, CDCl$_3$) δ 163.54, 153.75, 150.82, 145.36, 140.64, 132.05, 130.81, 128.42, 128.34, 128.25, 128.08, 126.06, 111.17, 101.64, 65.73, 48.38, 36.25, 20.50. LRMS (ES) calcd for C$_{20}$H$_{20}$N$_2$O$_3$ 336.4. found 358.9 [M+23]$^+$. HRMS (ES) calcd for C$_{20}$H$_{20}$N$_2$O$_3$ [M+1]$^+$ 337.1546. found 337.1543.

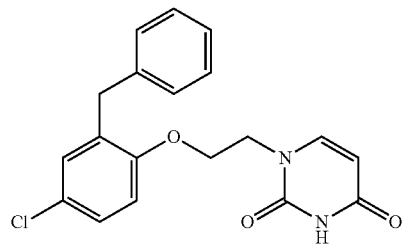 [SMILES: O=c1ccn(CCOc2ccc(Cl)cc2Cc2ccccc2)c(=O)[nH]1]

1-(2-(2-benzyl-4-chlorophenoxy)ethyl)pyrimidine-2,4(1H,3H)-dione (5)

(0.31 g, 97%). $^1$H NMR (500 MHz, CDCl$_3$+MeOD) δ 7.42 (d, J=2.1 Hz, 1H), 7.20 (dd, J=2.6, 8.7 Hz, 1H), 7.12 (dd, J=2.1, 8.3 Hz, 1H), 7.04 (d, J=7.9 Hz, 1H), 6.96 (d, J=2.5 Hz, 1H), 6.84-6.76 (m, 2H), 5.54 (d, J=7.9 Hz, 1H), 4.16 (t, J=4.7 Hz, 2H), 4.03 (t, J=4.7 Hz, 2H), 3.92 (s, 2H). $^{13}$C NMR (126 MHz, CDCl$_3$+MeOD) δ 164.36, 154.48, 151.10, 145.41, 135.77, 134.62, 133.02, 130.81, 130.65, 129.31, 128.67, 128.04, 127.33, 126.61, 112.50, 101.94, 65.86, 48.60, 33.13. LRMS (ES) calcd for C$_9$H$_{15}$Cl$_3$N$_2$O$_3$ 425.7. found 425 [M]$^+$. HRMS (ES) calcd for C$_{19}$H$_{17}$ClN$_2$O$_3$ [M+1]$^+$ 357.0221. found 357.0217.

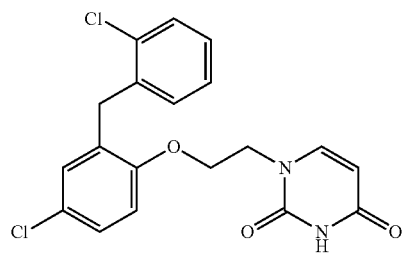 [SMILES: O=c1ccn(CCOc2ccc(Cl)cc2Cc2ccccc2Cl)c(=O)[nH]1]

1-(2-(4-chloro-2-(2-chlorobenzyl)phenoxy)ethyl)pyrimidine-2,4(1H,3H)-dione (6)

(0.18 g, 53%). $^1$H NMR (500 MHz, CDCl$_3$) δ 8.85 (s, 1H), 7.42 (dd, J=1.8, 8.1 Hz, 1H), 7.26-7.22 (m, 2H), 7.19 (dd, J=1.8, 8.3 Hz, 1H), 7.02 (d, J=2.1 Hz, 1H), 6.95 (d, J=8.2 Hz, 1H), 6.78 (d, J=8.3 Hz, 1H), 5.47 (d, J=7.9 Hz, 1H), 4.17 (t, J=4.0 Hz, 2H), 4.03 (t, J=4.0 Hz, 2H), 3.98 (s, 2H). $^{13}$C NMR (126 MHz, CDCl$_3$) δ 163.23, 154.48, 150.66, 145.07, 136.97, 133.89, 130.90, 129.68, 129.46, 129.03, 127.99, 127.80, 126.97, 126.53, 111.25, 101.90, 65.89, 48.45, 33.65. HRMS (ES) calcd for C$_{19}$H$_{16}$Cl$_2$N$_2$O$_3$ [M+1]$^+$ 391.0610. found 391.0607.

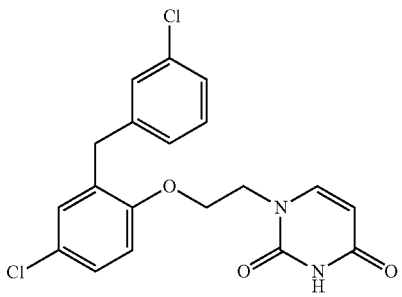 [SMILES: O=c1ccn(CCOc2ccc(Cl)cc2Cc2cccc(Cl)c2)c(=O)[nH]1]

1-(2-(4-chloro-2-(3-chlorobenzyl)phenoxy)ethyl)
pyrimidine-2,4(1H,3H)-dione (7)

(0.15, 45%). $^1$H NMR (500 MHz, CDCl$_3$+MeOD) δ 7.13-7.12 (m, 3H), 6.99 (d, 8.7 Hz, 2H), 6.92 (m, 2H), 6.73 (d, J=7.9 Hz, 1H), 5.47 (d, J=7.9 Hz, 1H), 4.11 (t, J=4.1 Hz, 2H), 4.07 (t, J=4.2 Hz, 2H), 3.82 (s, 2H). $^{13}$C NMR (126 MHz, CDCl$_3$+MeOD) δ 164.39, 154.30, 151.10, 145.20, 141.66, 134.20, 130.74, 129.75, 129.65, 128.24, 127.71, 126.45, 115.64, 112.42, 101.94, 65.86, 48.37, 35.50 HRMS (ES) calcd for C$_{19}$H$_{16}$Cl$_2$N$_2$O$_3$ [M+1]$^+$ 391.0608. found 391.0607.

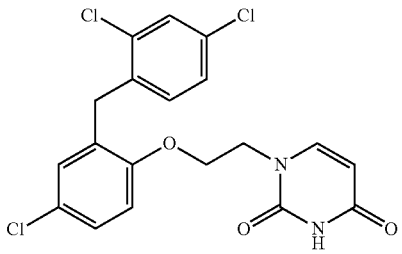 [SMILES: O=c1ccn(CCOc2ccc(Cl)cc2Cc2ccc(Cl)cc2Cl)c(=O)[nH]1]

1-(2-(4-chloro-2-(2,4-dichlorobenzyl)phenoxy)ethyl)
pyrimidine-2,4(1H,3H)-dione (8)

(0.28 g, 75%) $^1$H NMR (500 MHz, CDCl$_3$+MeOD) δ 7.42 (d, J=2.1 Hz, 1H), 7.20 (dd, J=2.6, 8.7 Hz, 1H), 7.12 (dd, J=2.1, 8.3 Hz, 1H), 7.04 (d, J=7.9 Hz, 1H), 6.96 (d, J=2.5 Hz, 1H), 6.84-6.76 (m, 2H), 5.54 (d, J=7.9 Hz, 1H), 4.16 (t, J=4.7 Hz, 2H), 4.03 (t, J=4.7 Hz, 2H), 3.92 (s, 2H). $^{13}$C NMR (126 MHz, CDCl$_3$+MeOD) δ 164.36, 154.48, 151.10, 145.41, 135.77, 134.62, 133.02, 130.81, 130.65, 129.31, 128.67, 128.04, 127.33, 126.61, 112.50, 101.94, 65.86, 48.60, 33.13. LRMS (ES) calcd for C$_{19}$H$_{15}$Cl$_3$N$_2$O$_3$ 425.7. found 425 [M]$^+$. HRMS (ES) calcd for C$_{19}$H$_{15}$Cl$_3$N$_2$O$_3$ [M+1]$^+$ 425.0221. found 425.0217.

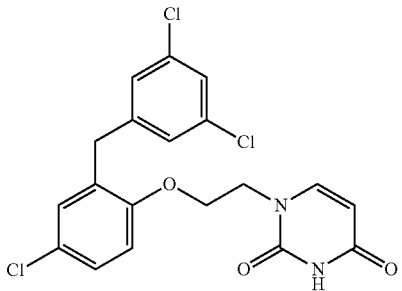

1-(2-(4-chloro-2-(3,5-dichlorobenzyl)phenoxy)ethyl)
pyrimidine-2,4(1H,3H)-dione (9)

(0.30 g, 81%). $^1$H NMR (500 MHz, CDCl$_3$) δ 8.61 (s, 1H), 7.23 (dd, J=2.2, 3.4 Hz, 2H), 7.21 (d, J=2.6 Hz, 1H), 7.08 (d, J=2.6 Hz, H), 6.96-6.95 (m, 2H), 6.79 (d, J=8.8, 1H), 5.55 (dd, J=2.1, 7.9 Hz, 1H), 4.20 (t, J=4.6 Hz, 2H), 4.06 (t, J=5.0 Hz, 2H), 3.85 (s, 2H). $^{13}$C NMR (126 MHz, CDCl$_3$+MeOD) δ 164.12, 154.18, 150.92, 144.96, 143.06, 134.83, 130.68, 128.75, 128.00, 126.66, 126.46, 126.33, 126.09, 112.48, 101.73, 65.64, 48.39, 35.23. LRMS (ES) calcd for C$_{19}$H$_{15}$Cl$_3$N$_2$O$_3$ 425.7. found 425.2 [M$^+$]. HRMS (ES) calcd for C$_{19}$H$_{15}$O$_3$N$_2$O$_3$ [M+1]$^+$ 425.0221. found 425.0222.

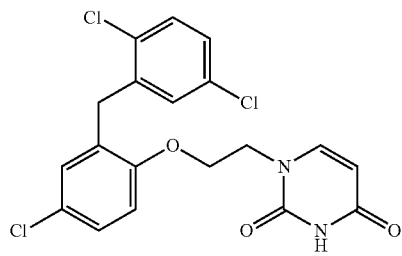 [SMILES: O=c1ccn(CCOc2ccc(Cl)cc2Cc2cc(Cl)ccc2Cl)c(=O)[nH]1]

1-(2-(4-chloro-2-(2,5-dichlorobenzyl)phenoxy)ethyl)
pyrimidine-2,4(1H,3H)-dione (10)

(0.14 g, 38%). $^1$H NMR (500 MHz, CDCl$_3$+MeOD) δ 7.34 (t, J=8.6 Hz, 1H), 7.24 (dd, J=2.6, 8.7 Hz, 1H), 7.17 (dd, J=2.5, 8.5 Hz, 1H), 7.03-7.00 (m, 2H), 6.83-6.81 (m, 2H), 5.49 (d, J=7.9 Hz, 1H), 4.19 (t, J=4.1 Hz, 2H), 4.04 (t, J=4.0 Hz, 2H), 3.94 (s, 2H). $^{13}$C NMR (126 MHz, CDCl$_3$+MeOD) δ 164.28, 154.51, 151.05, 145.21, 138.99, 132.90, 132.21, 130.87, 130.59, 129.64, 128.24, 128.18, 128.09, 126.64, 112.59, 101.93, 65.86, 48.58, 33.64. LRMS (ES) calcd for C$_{19}$H$_{15}$Cl$_3$N$_2$O$_3$ 425.7. found 425 [M]$^+$. HRMS (ES) calcd for C$_{19}$H$_{16}$Cl$_3$N$_2$O$_3$ [M+1]$^+$ 425.0221. found 425.0221.

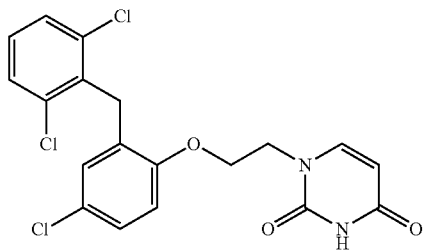 [SMILES: O=c1ccn(CCOc2ccc(Cl)cc2Cc2c(Cl)cccc2Cl)c(=O)[nH]1]

1-(2-(4-chloro-2-(2,6-dichlorobenzyl)phenoxy)ethyl)
pyrimidine-2,4(1H,3H)-dione (11)

(0.21 g, 58%). $^1$H NMR (400 MHz, CDCl$_3$+MeOD) δ 7.44-7.35 (m, 3H), 7.22 (t, J=8.5 Hz, 1H), 7.14 (dd, J=2.4, 8.7 Hz, 1H), 6.78 (d, J=8.7 Hz, 1H), 6.51 (d, J=2.4 Hz, 1H), 5.72 (dd, J=1.8, 7.9 Hz, 1H), 4.28 (t, J=4.5 Hz, 2H), 4.21 (t, J=4.5 Hz, 2H), 4.18 (s, 2H). $^{13}$C NMR (101 MHz, CDCl$_3$+MeOD) δ 164.27, 154.08, 151.04, 145.71, 136.32, 134.80, 128.84, 128.51, 128.13, 127.82, 127.20, 126.52, 111.94, 102.00, 65.88, 48.58, 30.67. LRMS (ES) calcd for C$_{19}$H$_{15}$Cl$_3$N$_2$O$_3$ 425.7. found 427.0 [M+1]$^+$. HRMS (ES) calcd for C$_{19}$H$_{15}$Cl$_3$N$_2$O$_3$ [M+1]$^+$ 425.0221. found 425.0222.

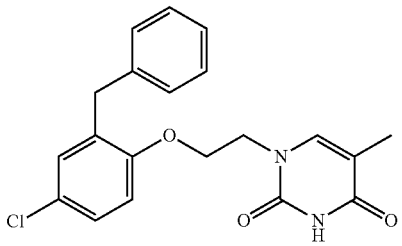

1-(2-(2-benzyl-4-chlorophenoxy)ethyl)-5-methylpyrimidine-2,4(1H,3H)-dione (12)

(0.25 g, 70%). $^1$H NMR (500 MHz, DMSO) δ 11.32 (s, 1H), 7.55 (s, 1H), 7.31-7.13 (m, 7H), 7.01 (dd, J=3.45, 8.56 Hz, 1H), 4.20 (s, 2H), 4.07 (s, 2H), 3.83 (d, J=23.39 Hz, 2H), 1.77-1.53 (m, 3H). $^{13}$C NMR (126 MHz, DMSO) δ 164.58, 154.84, 151.34, 142.23, 140.40, 132.07, 129.99, 128.90, 128.69, 127.40, 126.39, 124.79, 113.85, 108.65, 66.12, 47.15, 34.88, 12.22. HRMS (ES) calcd for C$_{20}$H$_{19}$ClN$_2$O$_3$ [M+1]$^+$ 371.1156. found 371.1161.

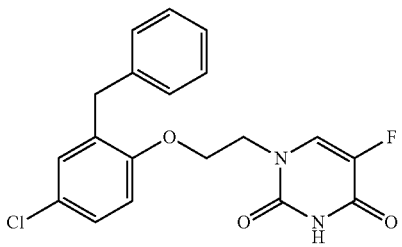 [SMILES: O=c1[nH]c(=O)n(CCOc2ccc(Cl)cc2Cc2ccccc2)cc1F]

1-(2-(2-benzyl-4-chlorophenoxy)ethyl)-5-fluoropyrimidine-2,4(1H,3H)-dione (13)

(0.30 g, 90%). $^1$H NMR (400 MHz, DMSO) δ 11.9 (s, 1H), 8.05 (s, 1H), 7.20-7.18 (m, 3H), 7.17-7.10 (m, 4H), 6.93 (d, J=8.71 Hz, 1H), 4.17 (t, J=4.5 Hz, 2H), 4.02 (s, 2H), 3.81 (t, J=4.4 Hz, 2H). $^{13}$C NMR (101 MHz, DMSO) δ 157.38, 157.18, 154.37, 149.58, 140.26, 139.88, 131.55, 130.50, 130.24, 129.62, 128.41, 128.23, 126.98, 125.96, 124.36, 113.36, 65.54, 47.07, 34.50. HRMS (ES) calcd for C$_{19}$H$_{16}$ClFN$_2$O$_3$ [M+1]$^+$ 375.0712. found 375.0712.

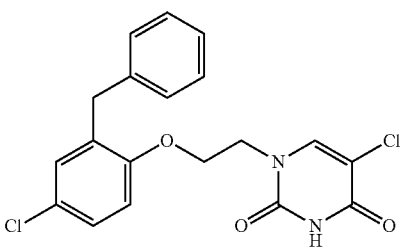 [SMILES: O=c1[nH]c(=O)n(CCOc2ccc(Cl)cc2Cc2ccccc2)cc1Cl]

1-(2-(2-benzyl-4-chlorophenoxy)ethyl)-5-chloropyrimidine-2,4(1H,3H)-dione (14)

(0.26 g, 75%). $^1$H NMR (400 MHz, CDCl$_3$) δ 9.37 (s, 1H), 7.33 (s, 1H), 7.32-7.24 (m, 2H), 7.24-7.14 (m, 2H), 7.13-7.03 (m, 3H), 6.75 (d, J=8.71 Hz, 1H), 4.22-4.08 (m, 2H), 4.06-3.95 (m, 2H), 3.91 (s, 2H). $^{13}$C NMR (101 MHz, CDCl$_3$) δ 159.18, 154.30, 149.90, 142.14, 139.24, 130.93, 130.75, 128.60, 128.27, 127.48, 126.61, 126.41, 112.42, 108.59, 65.60, 48.85, 36.00. HRMS (ES) calcd for C$_{19}$H$_{16}$Cl$_2$N$_2$O$_3$ [M+1]$^+$ 391.0610. found 391.0614.

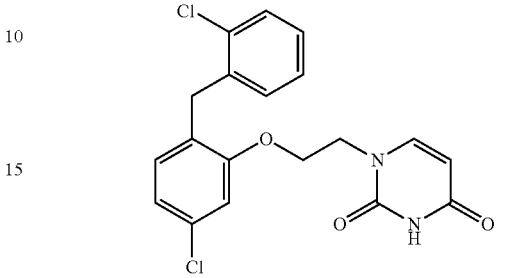

1-(2-(5-chloro-2-(2-chlorobenzyl)phenoxy)ethyl)pyrimidine-2,4(1H,3H)-dione (15)

(0.15 g, 45%). $^1$H NMR (500 MHz, CDCl$_3$) δ 8.18 (s, 1H), 7.41 (d, J=7.78 Hz, 1H), 7.22-7.16 (m, 1H), 7.14-7.09 (m, 1H), 7.01-6.91 (m, 3H), 6.86 (s, 1H), 6.81 (d, J=7.47 Hz, 1H), 5.45 (d, J=7.78 Hz, 1H), 4.27-4.12 (m, 2H), 4.01 (dd, J=10.61, 15.29 Hz, 4H). $^{13}$C NMR (126 MHz, CDCl$_3$) δ 154.90, 154.30, 139.44, 139.39, 135.40, 132.62, 132.45, 132.27, 130.93, 130.75, 130.42, 128.60, 128.31, 127.61, 127.48, 126.51, 126.16, 114.12, 110.49, 68.32, 39.03, 33.03. HRMS (ES) calcd for C$_{19}$H$_{16}$Cl$_2$N$_2$O$_3$ [M+1]$^+$ 391.0611. found 391.0611.

General Procedure for the Synthesis of Compounds 20-27
Step 1

A mixture of aryl fluoride (51 a-d) (2.0 mmol), 5-chloro-2-methoxyphenol$^{5a}$ (50 a) (0.32 g, 2.0 mmol) or 4-chloro-2-methoxyphenol (50 b) (0.32 g, 2.0 mmol) in DMSO (3.0 mL) and anhydrous K$_2$CO$_3$ (0.41 g, 3.0 mmol) was heated at 120° C. for 5 h. The mixture was poured into ice water and extracted with EtOAc (3×50 mL). The organic layer was sequentially washed with brine (2×75 mL), dried over anhydrous Na$_2$SO$_4$, and concentrated in vacuo. The residue was purified by column chromatography to give 52 a-e and 36.

5-(5-chloro-2-methoxyphenoxy)isophthalonitrile (52 a)

(0.28 g, 50%) $^1$H NMR (500 MHz, CDCl$_3$) δ 7.59 (d, J=1.28 Hz, 1H), 7.32 (d, J=1.32 Hz, 2H), 7.30-7.25 (m, 1H), 7.12 (d, J=2.37 Hz, 1H), 6.99 (d, J=8.84 Hz, 1H), 3.77 (s, 3H). $^{13}$C NMR (126 MHz, CDCl$_3$) δ 158.66, 150.14, 128.69, 127.30, 126.07, 123.27, 122.98, 118.60, 118.53, 116.32, 115.01, 113.97, 56.10.

3-chloro-2-(5-chloro-2-methoxyphenoxy)benzonitrile (52 b)

(0.48 g, 83%) $^1$H NMR (500 MHz, CDCl$_3$) δ 7.65 (dd, J=1.53, 7.96, 2H), 7.28 (dd, J=4.99, 12.99 Hz, 1H), 7.13-6.81 (m, 2H), 6.54 (d, J=2.42 Hz, 1H), 3.80 (s, 3H). $^{13}$C NMR (126 MHz, CDCl$_3$) δ 153.09, 148.35, 146.28, 135.61, 132.44, 128.77, 126.25, 125.45, 124.06, 116.27, 114.31, 113.80, 109.04, 56.57.

3-chloro-5-(5-chloro-2-methoxyphenoxy)benzonitrile (52 c)

(0.31 g, 53%) $^1$H NMR (500 MHz, CDCl$_3$) δ 7.61-7.32 (m, 2H), 7.21 (d, J=2.02 Hz, 2H), 7.26-7.12 (m, 2H), 3.77 (s, 3H). $^{13}$C NMR (126 MHz, CDCl$_3$) δ 158.9, 148.94, 129.53, 128.00, 126.15, 124.02, 123.11, 122.56, 118.53, 116.66, 114.19, 113.09, 56.10.

4-chloro-3-(4-chloro-2-methoxyphenoxy)benzonitrile (52 d)

(0.28 g, 50%) $^1$H NMR (500 MHz, CDCl$_3$) δ 7.57 (d, J=1.32 Hz, 1H), 7.31 (d, J=1.32 Hz, 2H), 7.07-7.00 (m, 2H), 6.84 (s, 1H), 3.78 (s, 3H). $^{13}$C NMR (126 MHz, CDCl$_3$) δ 158.88, 151.83, 140.15, 132.67, 128.52, 123.36, 123.14, 121.52, 121.09, 116.34, 114.98, 113.91, 56.10.

2-(4-chloro-2-methoxyphenoxy)isophthalonitrile (52 e)

(0.70 g, 81%) $^1$H NMR (500 MHz, CDCl$_3$) δ 7.40 (s, 1H), 7.11-7.07 (m, 2H), 7.01-6.88 (m, 3H), 3.88 (s, 3H). $^{13}$C NMR (126 MHz, CDCl$_3$) δ 167.45, 159.34, 152.32, 140.90, 135.96, 135.47, 131.12, 123.20, 121.40 121.25, 119.79, 113.77, 113.64, 56.14.

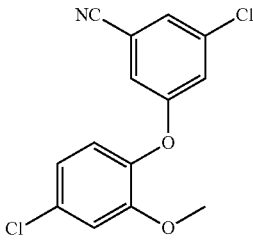 [SMILES: COc1cc(Cl)ccc1Oc1cc(Cl)cc(C#N)c1]

3-chloro-5-(4-chloro-2-methoxyphenoxy)benzonitrile (36)

(0.79 g, 91%). $^1$H NMR (500 MHz, CDCl$_3$) δ 7.29 (s, 1H), 7.11-7.07 (m, 1H), 7.03 (d, J=1.76 Hz, 1H), 7.01-6.97 (m, 3H), 3.79 (s, 3H). $^{13}$C NMR (126 MHz, CDCl$_3$) δ 167.45, 159.01, 152.10, 141.81, 136.06, 135.47, 131.33, 123.00, 121.40, 121.25, 119.79, 113.77, 113.64, 56.14. HRMS (ES) calcd for C$_{14}$H$_9$Cl$_2$NO$_2$ [M+1]$^+$ 293.9931. found 293.9938.

Step 2

A solution of BBr$_3$ (5.0 mmol, 1M in CH$_2$Cl$_2$) was added dropwise to a solution of 52 a-d or 36 (1.0 mmol) in dry CH$_2$Cl$_2$ (4.0 mL) under N$_2$ at −78° C. The reaction mixture was stirred at this temperature for 1 h. After this period, the reaction was allowed to warm to room temperature and stirred for 12 h. After completion, the solution was quenched with methanol, the solvent was removed in vacuo and the residue was extracted with CH$_2$Cl$_2$ and washed with a solution of NaHCO$_3$. The combined organic layer was washed with brine, dried over anhydrous Na$_2$SO$_4$ and concentrated in vacuo. The residue was purified by column chromatography (SiO$_2$, Hexane/EtOAc 80:20) to give 53 a-e.

5-(5-chloro-2-hydroxyphenoxy)isophthalonitrile (53 a)

(0.14 g, 51%) $^1$H NMR (500 MHz, CDCl$_3$) δ 7.66 (t, J=1.29 Hz, 1H), 7.45 (d, J=1.25 Hz, 2H), 7.29-7.15 (m, 1H), 7.02 (dd, J=1.57, 8.27 Hz, 2H), 5.65 (s, 1H). LRMS (ES) calcd for C$_{14}$H$_7$ClN$_2$O$_2$ 271.7. found 271.3 [M$^+$].

3-chloro-2-(5-chloro-2-hydroxyphenoxy)benzonitrile (53 b)

(0.2 g, 87%) $^1$H NMR (500 MHz, CDCl$_3$) δ 7.57-7.33 (m, 3H), 7.22 (dd, J=1.25, 8.1 Hz, 1H), 7.14 (m, 2H), 5.65 (s, 1H). LRMS (ES) calcd for C$_{13}$H$_7$Cl$_2$NO$_2$ 281.9. found 281.7 [M$^+$].

3-chloro-5-(5-chloro-2-hydroxyphenoxy)benzonitrile (53 c)

(0.31, 100%) $^1$H NMR (500 MHz, CDCl$_3$) δ 7.60 (d, J=0.99 Hz, 1H), 7.51-7.45 (m, 1H), 7.37 (dd, J=1.58, 6.06 Hz, 3H), 7.20 (d, J=8.48 Hz, 1H), 5.55 (s, 1H). LRMS (ES) calcd for C$_{13}$H$_7$Cl$_2$NO$_2$ 281.0. found 281.3 [M$^+$].

4-chloro-3-(4-chloro-2-hydroxyphenoxy)benzonitrile (53 d)

(0.25 g, 96%) $^1$H NMR (500 MHz, CDCl$_3$) δ 7.60 (dd, J=1.29, 8.1 Hz, 1H), 7.53-7.25 (m, 3H), 7.12 (d, J=8.1 Hz, 2H), 5.65 (s, 1H). HRMS (ES) calcd for C$_{13}$H$_7$Cl$_2$NO$_2$ [M+1]$^+$ 280.9934. found 280.9930.

5-(4-chloro-2-hydroxyphenoxy)isophthalonitrile (53 e)

(0.13 g, 50%) $^1$H NMR (500 MHz, CDCl$_3$) δ 7.98 (s, 1H), 7.63 (s, 1H), 7.50 (dd, J=1.98, 8.47 Hz, 1H), 7.39 (d, J=1.28 Hz, 1H), 7.35 (d, J=1.96 Hz, 1H), 7.27 (s, 1H), 7.19 (d, J=8.48 Hz, 1H), 5.69 (s, 1H). LRMS (ES) calcd for C$_{14}$H$_7$ClN$_2$O$_2$ 271.1. found 271 [M$^+$].

3-chloro-5-(4-chloro-2-hydroxyphenoxy)benzonitrile (53 f)

(0.26 g, 93%): $^1$H NMR (400 MHz, CDCl$_3$) δ 7.38 (d, J=1.58 Hz, 1H), 7.21 (d, J=2.02 Hz, 1H), 7.16-7.12 (m, 1H), 7.11 (d, J=2.29 Hz, 1H), 6.94-6.86 (m, 2H), 5.49 (s, 1H). $^{13}$C NMR (101 MHz, CDCl$_3$) δ 158.06, 148.24, 140.00, 136.67, 131.73, 126.85, 122.06, 121.49, 121.16, 118.61, 117.75, 116.75, 114.79.

Step 3

To solution of 53 a-f (2.5 mmol), PPh$_3$ (0.74 g, 2.8 mmol) and 2-bromoethanol (0.20 mL, 2.8 mmol) in dry THF (6 mL), DIAD (0.54 mL, 2.8 mmol) was added dropwise at rt and the reaction mixture was stirred overnight. The reaction mixture was concentrated under reduced pressure and purified by column chromatography (SiO$_2$, hexane/EtOAc 80:20) to give 54 a-f.

5-(2-(2-bromoethoxy)-5-chlorophenoxy)isophthalonitrile (54 a)

(0.75 g, 83%) $^1$H NMR (500 MHz, CDCl$_3$) δ 7.58 (t, J=1.35 Hz, 1H), 7.35 (dd, J=1.36, 6.70 Hz, 2H), 7.20-6.93 (m, 3H), 4.25 (dd, J=4.93, 10.68 Hz, 2H), 3.53-3.41 (m, 2H). $^{13}$C NMR (126 MHz, CDCl$_3$) δ 158.86, 150.26, 140.61, 132.52, 128.69, 123.80, 123.42, 122.42, 116.38, 115.00, 114.96, 68.66, 28.40.

2-(2-(2-bromoethoxy)-5-chlorophenoxy)-3-chlorobenzonitrile (54 b)

(0.82 g, 83%) $^1$H NMR (500 MHz, CDCl$_3$) δ 7.76-7.50 (m, 2H), 7.35-7.21 (m, 1H), 6.93 (dd, J=2.36, 10.54 Hz, 2H), 6.80-6.60 (m, 1H), 4.34 (dt, J=6.38, 10.67 Hz, 2H), 3.58-3.43 (m, 2H). $^{13}$C NMR (126 MHz, CDCl$_3$) δ 153.24, 146.65, 132.42, 129.44, 128.47, 126.12, 124.28, 121.74, 118.57, 116.46, 115.49, 114.56, 108.36, 69.67, 28.24.

3-(2-(2-bromoethoxy)-5-chlorophenoxy)-5-chlorobenzonitrile (54 c)

(0.76 g, 79%) $^1$H NMR (500 MHz, CDCl$_3$) δ 7.40 (d, J=8.58 Hz, 2H), 7.33-7.29 (m, 1H), 7.12 (d, J=2.34 Hz, 1H), 6.96 (d, J=8.30 Hz, 1H), 6.89 (d, J=2.33 Hz, 1H), 4.35 (t, J=6.18 Hz, 2H), 3.55 (t, J=6.18 Hz, 2H). $^{13}$C NMR (126 MHz, CDCl$_3$) δ 152.23, 149.14, 133.36, 132.42, 131.50, 127.00, 125.38, 122.42, 120.13, 119.95, 118.48, 108.46, 69.47, 28.07.

3-(2-(2-bromoethoxy)-5-chlorophenoxy)-4-chlorobenzonitrile (54 d)

(0.72 g, 75%) $^1$H NMR (400 MHz, CDCl$_3$) δ 7.54 (d, J=8.20 Hz, 1H), 7.30-7.26 (m, 1H), 7.12-6.99 (m, 3H), 6.90 (d, J=1.80 Hz, 1H), 4.25 (t, J=5.98 Hz, 2H), 3.45 (t, J=5.98 Hz, 2H). $^{13}$C NMR (101 MHz, CDCl$_3$) δ 154.28, 150.09, 141.92, 131.83, 131.54, 128.88, 126.68, 123.33, 122.37, 119.35, 117.68, 115.44, 111.42, 68.91, 28.21.

5-(2-(2-bromoethoxy)-4-chlorophenoxy)isophthalonitrile (54 e)

(0.84 g, 92%) $^1$H NMR (500 MHz, CDCl$_3$) δ 7.66-7.61 (m, 2H), 7.49 (dd, J=1.25, 1.93 Hz, 1H), 7.38-7.34 (m, 2H), 7.10 (d, J=8.58 Hz, 1H), 4.34 (dd, J=3.11, 8.00 Hz, 2H), 3.58-3.41 (m, 2H). $^{13}$C NMR (126 MHz, CDCl$_3$) δ 158.27, 153.58, 142.15, 132.13, 129.29, 126.69, 123.56, 117.49, 116.18, 115.28, 114.35, 105.93, 70.08, 68.71, 27.99, 21.96.

3-(2-(2-bromoethoxy)-4-chlorophenoxy)-5-chlorobenzonitrile (54 f)

(0.66 g, 68%) $^1$H NMR (500 MHz, CDCl$_3$) δ 7.30-7.28 (m, 1H), 7.12-7.09 (m, 1H), 7.06 (s, 1H), 7.05 (d, J=2.18 Hz, 1H), 7.02 (ddd, J=2.23, 4.10, 7.47 Hz, 2H), 4.25 (t, J=5.94 Hz, 2H), 3.47 (t, J=5.94 Hz, 2H). $^{13}$C NMR (126 MHz, CDCl$_3$) δ 159.07, 150.43, 141.36, 136.09, 131.91, 125.64, 123.70, 122.31, 121.18, 117.75, 117.14, 115.13, 114.27, 68.73, 60.37, 28.19, 21.04, 14.18.

Step 4

Compounds 54 a-f (0.13 mmol) were treated with the corresponding uracil (0.19 g, 1.5 mmol), NH$_4$Cl (0.02 g, 0.37 mmol) and HMDS (3 mL) as described above for the synthesis of 5-12, to afford the desired products 20-27.

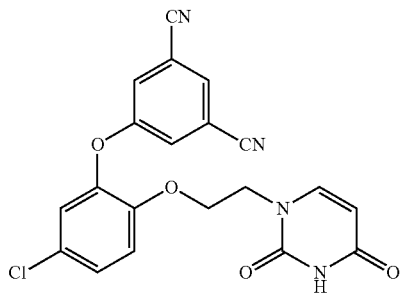 [SMILES: N#Cc1cc(C#N)cc(Oc2cc(Cl)ccc2OCCn2ccc(=O)[nH]c2=O)c1]

5-(5-chloro-2-(2-(2,4-dioxo-3,4-dihydropyrimidin-1(2H)-yl)ethoxy)phenoxy)isophthalonitrile (20)

(0.05 g, 100%) $^1$H NMR (500 MHz, DMSO) δ 11.20 (d, J=3.85 Hz, 1H), 8.21-8.03 (m, 1H), 7.81-7.65 (m, 2H), 7.42 (d, J=2.27 Hz, 1H), 7.28 (d, J=8.53 Hz, 1H), 7.25-7.20 (m, 1H), 7.16 (dd, J=2.32, 8.54 Hz, 1H), 5.26-5.14 (m, 1H), 4.38-4.21 (m, 2H), 4.14-3.83 (m, 2H). $^{13}$C NMR (126 MHz, DMSO) δ 163.73, 158.33, 151.13, 151.10, 145.95, 140.63, 131.33, 130.20, 124.23, 123.88, 122.06, 117.03, 115.54, 114.41, 100.52, 66.78, 47.17. HRMS (ES) calcd for C$_{20}$H$_{13}$ClN$_4$O$_4$ [M+1]$^+$ 409.0511. found 409.0500.

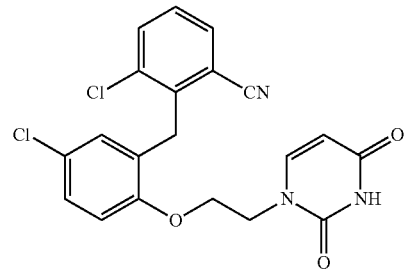 [SMILES: N#Cc1cccc(Cl)c1Cc1cc(Cl)ccc1OCCn1ccc(=O)[nH]c1=O]

3-chloro-2-(5-chloro-2-(2-(2,4-dioxo-3,4-dihydropyrimidin-1(2H)-yl)ethoxy)phenoxy)benzonitrile (21)

(0.05 g, 100%) $^1$H-NMR (500 MHz, DMSO) δ 11.25 (d, J=1.59 Hz, 1H), 8.00-7.79 (m, 2H), 7.60-7.39 (m, 2H), 7.32 (d, J=2.41 Hz, 1H), 6.93 (dd, J=2.41, 8.67 Hz, 1H), 6.66 (dd, J=4.49, 8.61 Hz, 1H), 5.41 (dd, J=2.25, 7.85 Hz, 1H), 4.28 (dt, J=5.25, 17.65 Hz, 2H), 4.14-4.00 (m, 2H). $^{13}$C NMR (126 MHz, DMSO) δ 163.57, 152.14, 150.86, 148.41, 145.90, 144.56, 136.15, 133.33, 128.02, 127.08, 126.90, 121.07, 117.07, 115.01, 107.47, 100.52, 66.83, 46.59. HRMS (ES) calcd for C$_{19}$H$_{13}$Cl$_2$N$_3$O$_4$ [M+1]$^+$ 418.0307. found 418.0319.

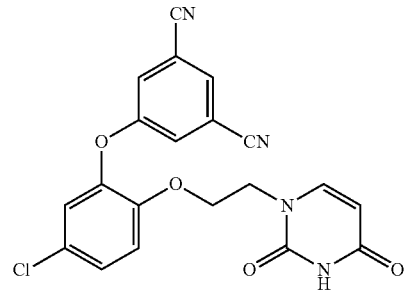 [SMILES: N#Cc1cc(C#N)cc(Oc2cc(Cl)ccc2OCCn2ccc(=O)[nH]c2=O)c1]

3-chloro-5-(5-chloro-2-(2-(2,4-dioxo-3,4-dihydropyrimidin-1(2H)-yl)ethoxy)phenoxy)benzonitrile (22)

(0.044 g, 82%) $^1$H NMR (500 MHz, CDCl$_3$) δ 8.93 (s, 1H), 7.36-7.33 (m, 1H), 7.25 (d, J=2.52 Hz, 1H), 7.09 (d, J=2.51 Hz, 1H), 7.08-7.06 (m, 1H), 6.96-6.94 (m, 1H), 6.82 (t, J=6.60 Hz, 1H), 5.41 (d, J=7.89 Hz, 1H), 4.27-4.19 (m, 2H), 4.06-3.94 (m, 2H). $^{13}$C NMR (126 MHz, CDCl$_3$) δ 163.04, 158.59, 150.57, 148.75, 144.81, 142.61, 136.50, 127.39, 127.09, 126.11, 123.24, 120.82, 117.18, 116.79, 115.30, 114.65, 101.63, 66.74, 48.37. HRMS (ES) calcd for C$_{19}$H$_{13}$Cl$_2$N$_3$O$_4$ [M+1]$^+$ 418.0171. found 418.0168.

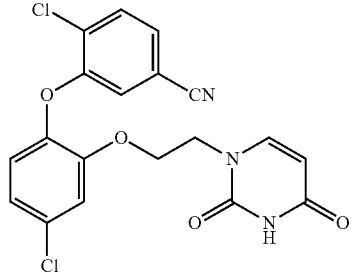 [SMILES: N#Cc1ccc(Cl)c(Oc2ccc(Cl)cc2OCCn2ccc(=O)[nH]c2=O)c1]

4-chloro-3-(4-chloro-2-(2-(2,4-dioxo-3,4-dihydropyrimidin-1(2H)-yl)ethoxy)phenoxy)benzonitrile (23)

(0.040 g, 75%) $^1$H NMR (500 MHz, CDCl$_3$) δ 9.40 (d, J=7.51 Hz, 1H), 7.57 (d, J=8.20 Hz, 1H), 7.36-7.26 (m, 1H), 7.08-7.00 (m, 3H), 6.95 (d, J=7.89 Hz, 1H), 6.77 (d, J=1.58 Hz, 1H), 5.39 (d, J=7.78 Hz, 1H), 4.23 (t, J=4.62 Hz, 2H), 4.08-3.95 (m, 2H). $^{13}$C NMR (126 MHz, CDCl$_3$) δ 163.52, 153.93, 150.70, 150.15, 144.97, 140.86, 132.27, 131.69, 128.06, 126.88, 123.36, 122.60, 118.20, 117.36, 115.12, 111.64, 101.79, 66.74, 53.46, 48.16. HRMS (ES) calcd for C$_{19}$H$_{13}$Cl$_2$N$_3$O$_4$ [M+1]$^+$ 418.0168. found 418.0168.

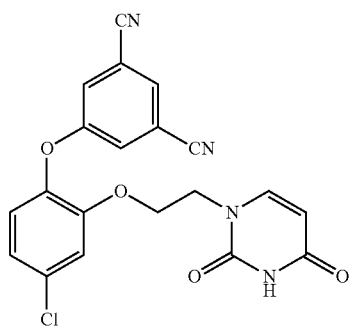 [SMILES: N#Cc1cc(C#N)cc(Oc2ccc(Cl)cc2OCCn2ccc(=O)[nH]c2=O)c1]

5-(4-chloro-2-(2-(2,4-dioxo-3,4-dihydropyrimidin-1(2H)-yl)ethoxy)phenoxy)isophthalonitrile (24)

(0.053 g, 100%). $^1$H NMR (500 MHz, DMSO) δ 11.15 (s, 1H), 8.02 (t, J=1.19 Hz, 1H), 7.64 (t, J=4.76 Hz, 2H), 7.33 (d, J=2.33 Hz, 1H), 7.18 (d, J=8.53 Hz, 1H), 7.13 (d, J=7.84 Hz, 1H), 7.06 (dd, J=2.33, 8.54 Hz, 1H), 5.12 (dd, J=2.16, 7.82 Hz, 1H), 4.19 (t, J=4.94 Hz, 2H), 3.95-3.74 (m, 2H). $^{13}$C NMR (126 MHz, DMSO) δ 163.73, 158.63, 158.27, 151.12, 150.15, 145.96, 140.88, 131.69, 131.40, 130.20, 124.24, 123.89, 122.06, 117.04, 115.54, 114.40, 100.50, 66.76, 47.15. HRMS (ES) calcd for C$_{20}$H$_{13}$ClN$_4$O$_4$ [M+1]$^+$ 409.0698. found 409.0698.

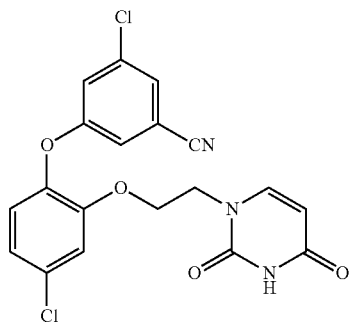 [SMILES: N#Cc1cc(Cl)cc(Oc2ccc(Cl)cc2OCCn2ccc(=O)[nH]c2=O)c1]

3-chloro-5-(4-chloro-2-(2-(2,4-dioxo-3,4-dihydropyrimidin-1(2H)-yl)ethoxy)phenoxy)benzonitrile (25)

$^1$H NMR (500 MHz, DMSO) δ 11.20 (s, 1H), 7.63 (d, J=1.15 Hz, 1H), 7.36 (d, J=2.28 Hz, 1H), 7.28 (s, 1H), 7.21 (dd, J=2.47, 8.25 Hz, 1H), 7.18-7.13 (m, 1H), 7.09 (dd, J=2.37, 8.48 Hz, 1H), 5.15 (dd, J=2.23, 7.76 Hz, 1H), 4.22 (d, J=4.30 Hz, 2H), 3.90 (s, 2H). $^{13}$C NMR (126 MHz, DMSO) δ 163.30, 158.48, 150.67, 145.49, 140.41, 134.98, 130.76, 125.75, 123.84, 121.62, 120.41, 117.78, 116.96, 115.02, 113.78, 100.03, 66.35, 46.80. HRMS (ES) calcd for C$_{19}$H$_{13}$Cl$_2$N$_3$O$_4$ [M+1]$^+$ 418.0171. found 418.0172.

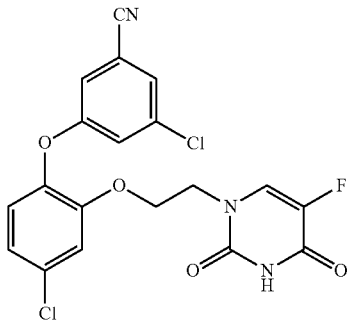 [SMILES: N#Cc1cc(Cl)cc(Oc2ccc(Cl)cc2OCCn2cc(F)c(=O)[nH]c2=O)c1]

3-chloro-5-(4-chloro-2-(2-(5-fluoro-2,4-dioxo-3,4-dihydropyrimidin-1(2H)-yl)ethoxy)phenoxy)benzonitrile (26)

$^1$H NMR (500 MHz, DMSO) δ 11.67 (d, J=5.05 Hz, 1H), 7.56-7.50 (m, 2H), 7.32 (d, J=2.35 Hz, 1H), 7.25 (dd, J=1.29, 2.35 Hz, 1H), 7.18 (d, J=8.54 Hz, 1H), 7.11-7.04 (m, 2H), 4.21 (t, J=4.97 Hz, 2H), 3.85 (d, J=4.94 Hz, 2H). $^{13}$C NMR (126 MHz, DMSO) δ 158.35, 157.14, 156.94, 150.74, 149.32, 140.51, 138.01, 134.98, 130.75, 130.10, 129.83, 125.65, 123.73, 121.69, 120.07, 117.71, 116.89, 115.11, 113.81, 99.50, 66.13, 47.01. HRMS (ES) calcd for C$_{19}$H$_{12}$Cl$_2$FN$_3$O$_4$ [M+1]$^+$ 436.0261. found 436.0261.

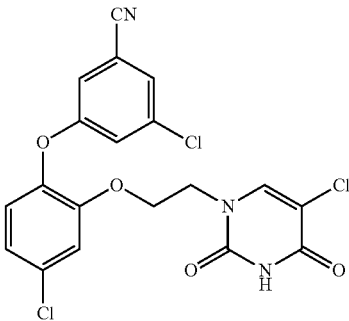 [SMILES: N#Cc1cc(Cl)cc(Oc2ccc(Cl)cc2OCCn2cc(Cl)c(=O)[nH]c2=O)c1]

3-chloro-5-(4-chloro-2-(2-(5-chloro-2,4-dioxo-3,4-dihydropyrimidin-1(2H)-yl)ethoxy)phenoxy)benzonitrile (27)

$^1$H NMR (500 MHz, DMSO) δ 11.61 (s, 1H), 7.57 (s, 1H), 7.45 (d, J=1.29 Hz, 1H), 7.21 (d, J=2.11 Hz, 1H), 7.16-7.12 (m, 1H), 7.05 (d, J=8.54 Hz, 1H), 7.01-6.98 (m, 1H), 6.94 (dd, J=2.23, 8.53 Hz, 1H), 4.21-4.04 (m, 2H), 3.77 (dt, J=25.61, 51.81 Hz, 2H). $^{13}$C NMR (126 MHz, DMSO) δ 159.13, 158.29, 150.74, 149.86, 142.89, 140.63, 134.98, 130.66, 125.81, 123.64, 121.69, 120.26, 117.87, 116.99, 115.14, 113.85, 105.72, 66.07, 47.12. HRMS (ES) calcd for C$_{19}$H$_{12}$Cl$_3$N$_3$O$_4$ [M+1]$^+$ 451.9966. found 451.9965.

Synthesis of Compounds 28-32.
Step 1

A mixture of the commercially available phenol (3.0 mmol), 4-fluoro-3-methoxybenzonitrile (57) (0.47 g, 6.0 mmol) in DMSO (4.0 mL) and anhydrous K$_2$CO$_3$ (0.62 g, 4.5 mmol) was heated at 130° C. for 5 h. The reaction mixture was poured into ice water and extracted with EtOAc (3×50 mL). The organic layer was sequentially washed with brine (2×75 mL), dried over anhydrous $Na_2SO_4$, and concentrated in vacuo. The residue was purified by column chromatography to give 66 a-f.

4-(3-chloro-5-cyanophenoxy)-3-methoxybenzonitrile (66 a)

yield (0.2 g, 23%) $^1$H NMR (500 MHz, $CDCl_3$) δ 7.39-7.32 (m, 2H), 7.30 (t, J=4.69 Hz, 1H), 7.17-7.10 (m, 2H), 7.05 (dd, J=1.31, 2.33 Hz, 1H), 3.78 (s, 3H). $^{13}$C NMR (126 MHz, DMSO) δ 163.73, 151.12, 145.96, 130.20, 124.24, 123.89, 122.06, 117.04, 115.54, 114.40, 100.50, 66.76, 47.15. LRMS (ES) calcd for $C_{15}H_9ClN_2O_2$ 289.4. found 289.2 [M]$^+$.

4-(2-chlorophenoxy)-3-methoxybenzonitrile (66 b)

yield (0.47 g, 62%) $^1$H NMR (500 MHz, $CDCl_3$) δ 7.47 (d, J=8.1 Hz, 1H), 7.35-7.23 (m, 3H), 7.18-7.13 (m, 2H), 7.05 (m, 1H), 3.78 (s, 3H). LRMS (ES) calcd for $C_{14}H_{10}ClNO_2$ 260.0. found 260.0 [M]$^+$.

4-(2,5-dichlorophenoxy)-3-methoxybenzonitrile (66c)

yield (0.54 g, 64%) $^1$H NMR (400 MHz, $CDCl_3$) δ 7.48-7.34 (m, 1H), 7.28-7.22 (m, 3H), 7.22-7.10 (m, 2H), 6.94-6.77 (m, 2H), 3.83 (s, 3H). $^{13}$C NMR (126 MHz, $CDCl_3$) δ 152.05, 150.58, 148.75, 133.34, 131.51, 125.8, 125.42, 123.77, 120.12, 118.46, 117.22, 116.73, 108.25, 56.41.

4-(3,5-dichlorophenoxy)-3-methoxybenzonitrile (66 d)

yield (0.88 g, 100%) $^1$H NMR (400 MHz, $CDCl_3$) δ 7.40 (d, J=1.5 Hz, 1H), 7.31-7.20 (m, 2H), 7.18 (dd, J=1.31, 2.33 Hz, 1H), 6.94-6.77 (m, 2H), 3.83 (s, 3H). $^{13}$C NMR (126 MHz, $CDCl_3$) δ 152.05, 150.58, 147.00, 133.34, 131.51, 125.95, 125.87, 125.41, 123.77, 120.12, 118.46, 116.73, 108.25, 49.91.

The final compounds 28-32 were prepared using the method described above for 20-27 (Step 2 to Step 4).

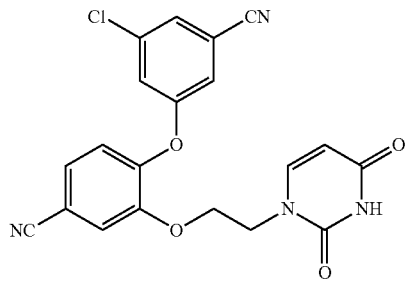 [SMILES: N#Cc1cc(Cl)cc(Oc2ccc(C#N)cc2OCCn2ccc(=O)[nH]c2=O)c1]

4-(3-chloro-5-cyanophenoxy)-3-(2-(2,4-dioxo-3,4-dihydropyrimidin-1(2H)-yl)ethoxy)benzonitrile (28)

$^1$H NMR (500 MHz, DMSO) δ 10.95 (s, 1H), 7.64-7.31 (m, 3H), 7.27-6.98 (m, 3H), 6.90 (d, J=7.85 Hz, 1H), 4.90 (dd, J=2.21, 7.83 Hz, 1H), 4.03 (t, J=4.92 Hz, 2H), 3.68 (t, J=4.89 Hz, 2H). $^{13}$C NMR (126 MHz, DMSO) δ 163.31, 158.08, 154.00, 150.68, 145.48, 141.59, 135.02, 132.10, 126.52, 126.17, 120.81, 118.20, 118.00, 116.94, 115.30, 113.82, 103.89, 100.06, 66.43, 54.85, 46.78. HRMS (ES) calcd for $C_{20}H_{13}ClN_4O_4$ [M+1]$^+$ 409.0698. found 409.0697.

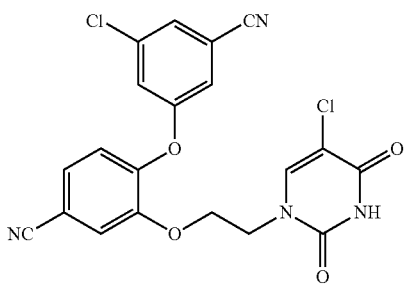 [SMILES: N#Cc1cc(Cl)cc(Oc2ccc(C#N)cc2OCCn2cc(Cl)c(=O)[nH]c2=O)c1]

3-(2-(5-chloro-2,4-dioxo-3,4-dihydropyrimidin-1 (2H)-yl)ethoxy)-4-(3-chloro-5-cyanophenoxy)benzonitrile (29)

$^1$H NMR (500 MHz, DMSO) δ 11.76 (s, 1H), 7.79 (dt, J=3.12, 6.23 Hz, 1H), 7.76-7.70 (m, 3H), 7.66-7.63 (m, 1H), 7.40 (d, J=8.68 Hz, 1H), 7.35 (dd, J=1.28, 2.33 Hz, 1H), 7.26-7.22 (m, 1H), 4.40-4.26 (m, 2H), 3.95 (dt, J=4.81, 21.78 Hz, 2H). $^{13}$C NMR (126 MHz, DMSO) δ 159.15, 157.87, 154.06, 149.88, 142.87, 141.84, 135.02, 131.98, 126.24, 120.70, 118.13, 116.97, 115.37, 113.89, 105.76, 103.92, 66.10, 47.05, 39.67. HRMS (ES) calcd for $C_{20}H_{13}Cl_2N_4O_4$ [M+1]$^+$ 444.1705. found 409.1700.

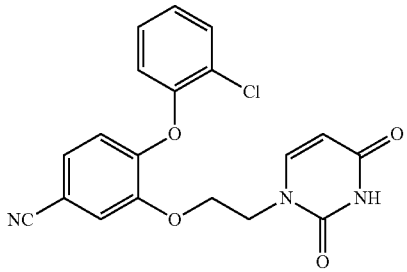 [SMILES: N#Cc1ccc(Oc2ccccc2Cl)c(OCCn2ccc(=O)[nH]c2=O)c1]

4-(2-chlorophenoxy)-3-(2-(2,4-dioxo-3,4-dihydropyrimidin-1(2H)-yl)ethoxy)benzonitrile (30)

$^1$H NMR (500 MHz, DMSO) δ 11.26 (t, J=17.47 Hz, 1H), 7.73 (d, J=1.82 Hz, 1H), 7.59 (dd, J=1.53, 7.98 Hz, 1H), 7.44 (dd, J=1.84, 8.32 Hz, 1H), 7.31 (ddd, J=1.69, 5.81, 9.72 Hz, 2H), 7.19 (td, J=1.43, 7.75 Hz, 1H), 6.99-6.91 (m, 2H), 5.34 (dd, J=2.22, 7.84 Hz, 1H), 4.33-4.25 (m, 2H), 4.04-3.83 (m, 2H). $^{13}$C NMR (126 MHz, DMSO) δ 163.48, 150.95, 150.78, 148.89, 148.44, 145.64, 130.69, 128.74, 126.66, 125.44, 123.43, 119.36, 118.40, 117.97, 107.00, 100.49, 66.59, 54.85, 46.54. HRMS (ES) calcd for $C_{19}H_{14}ClN_3O_4$ [M+1]$^+$ 384.0630. found 384.0639.

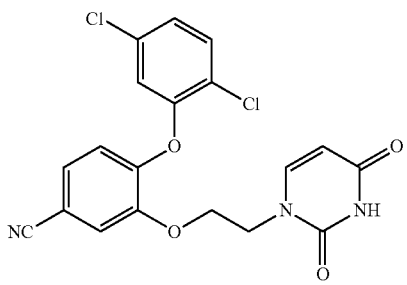 [SMILES: N#Cc1ccc(Oc2cc(Cl)ccc2Cl)c(OCCn2ccc(=O)[nH]c2=O)c1]

4-(2,5-dichlorophenoxy)-3-(2-(2,4-dioxo-3,4-dihydropyrimidin-1(2H)-yl)ethoxy)benzonitrile (31)

$^1$H NMR (400 MHz, CDCl$_3$) δ 8.83 (s, 1H), 7.43 (d, J=8.56 Hz, 1H), 7.37-7.31 (m, 1H), 7.25 (d, J=1.81 Hz, 1H), 7.15-7.07 (m, 2H), 6.97 (d, J=8.31 Hz, 1H), 6.76 (d, J=2.31 Hz, 1H), 5.51 (dd, J=1.98, 7.92 Hz, 1H), 4.30 (dd, J=8.87, 13.24 Hz, 2H), 4.12 (dt, J=5.69, 7.57 Hz, 2H). $^{13}$C NMR (126 MHz, CDCl$_3$) δ 163.18, 152.05, 150.63, 149.22, 148.21, 145.20, 133.63, 131.65, 127.17, 125.34, 122.85, 120.42, 118.80, 117.94, 117.60, 115.90, 108.97, 101.97, 67.32, 48.05. HRMS (ES) calcd for C$_{19}$H$_{13}$Cl$_2$N$_3$O$_4$ [M+1]$^+$ 418.0221. found 418.0249.

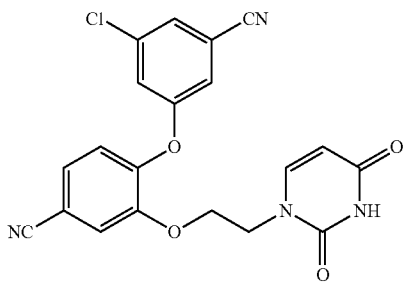 [SMILES: N#Cc1cc(Cl)cc(Oc2ccc(C#N)cc2OCCn2ccc(=O)[nH]c2=O)c1]

4-(3,5-dichlorophenoxy)-3-(2-(2,4-dioxo-3,4-dihydropyrimidin-1(2H)-yl)ethoxy)benzonitrile (32)

$^1$H NMR (400 MHz, CDCl$_3$) δ 8.02 (s, 1H), 7.35 (dd, J=1.81, 8.26 Hz, 1H), 7.22 (d, J=1.79 Hz, 1H), 7.11 (dd, J=1.82, 3.59 Hz, 2H), 6.85 (d, J=7.93 Hz, 1H), 6.73 (d, J=1.76 Hz, 2H), 5.44 (dd, J=2.28, 7.93 Hz, 1H), 4.22 (dd, J=13.12, 17.98 Hz, 2H), 4.08-3.99 (m, 2H). $^{13}$C NMR (126 MHz, CDCl$_3$) δ 163.01, 158.06, 150.70, 148.21, 145.27, 136.47, 127.61, 124.37, 123.00, 117.81, 115.92, 115.57, 110.25, 102.14, 67.31, 48.61. HRMS (ES) calcd for C$_{19}$H$_{13}$Cl$_2$N$_3$O$_4$ [M+1]$^+$ 419.0331 found 419.0330.

Synthesis of Compounds 33-34.

DIAD (0.082 mL, 0.42 mmol) was added slowly to a solution of 4-(2,5-dichlorophenoxy)-3-hydroxybenzonitrile (68)$^{6a}$ (0.1 g, 0.36 mmol) and triphenylphosphine (0.113 g, 0.42 mmol) in dry THF (2.0 mL) at room temperature. After stirring the reaction mixture for 10 minutes, 2-(pyridin-4-yl)ethanol (69a) (0.053 g, 0.43 mmol) or pyridin-4-ylmethanol (69b) (0.051 mL, 0.43 mmol) was added dropwise and the resulting mixture was stirred at room temperature overnight. After completion, the reaction mixture was concentrated under reduced pressure and purified by column chromatography (SiO$_2$, hexane/EtOAc 50:50) to give 33 (0.13 g, 94%) and 34 (0.107 g, 80%).

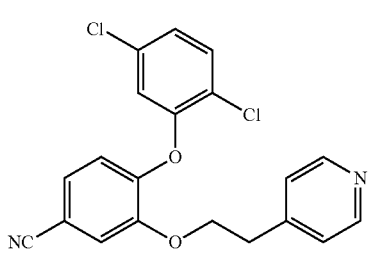 [SMILES: N#Cc1ccc(Oc2cc(Cl)ccc2Cl)c(OCCc2ccncc2)c1]

4-(2,5-dichlorophenoxy)-3-(2-(pyridin-4-yl)ethoxy)benzonitrile (33)

$^1$H NMR (500 MHz, CDCl$_3$) δ 8.45 (dd, J=4.1, 1.9 Hz, 2H), 7.38 (dd, J=8.5, 2.4 Hz, 1H), 7.29 (ddd, J=10.1, 6.0, 2.3 Hz, 1H), 7.23 (d, J=2.0 Hz, 1H), 7.12-7.05 (m, 3H), 7.00 (dd, J=8.2, 2.4 Hz, 1H), 6.77-6.66 (m, 1H), 4.29-4.14 (m, 2H), 3.02 (dd, J=5.7, 3.9 Hz, 2H). $^{13}$C NMR (126 MHz, CDCl$_3$) δ 149.91, 149.81, 146.57, 133.24, 131.42, 126.42, 124.88, 124.16, 122.83, 120.87, 118.61, 118.22, 117.26, 108.88, 68.64, 34.74. HR-MS (ES) calcd for C$_{20}$H$_{14}$Cl$_2$N$_2$O$_2$ [M+1]$^+$ 385.0520. found 385.0511.

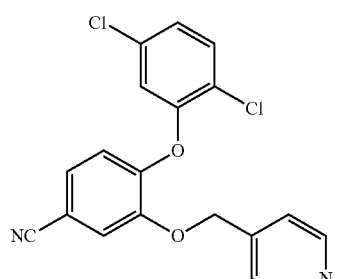

4-(2,5-dichlorophenoxy)-3-(pyridin-4-yl)methoxy)benzonitrile (34)

$^1$H NMR (500 MHz, CDCl$_3$) δ 8.60 (s, 2H), 7.40 (d, J=8.0 Hz, 1H), 7.33 (d, J=7.5 Hz, 1H), 7.30-7.18 (m, 3H), 7.12 (d, J=7.9 Hz, 1H), 7.00 (d, J=7.7 Hz, 1H), 6.90 (s, 1H), 5.15 (s, 2H). $^{13}$C NMR (126 MHz, CDCl$_3$) δ 152.23, 150.17, 149.07, 144.37, 133.40, 131.57, 126.98, 125.38, 123.47, 121.18, 120.17, 119.68, 117.94, 108.52, 69.40. HR-MS (ES) calcd for C$_{19}$H$_{12}$Cl$_2$N$_2$O$_2$ [M+1]$^+$ 371.0363. found 371.0354.

Synthesis of Compound 35

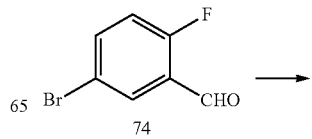

Step 4

To a solution of 71 (0.1 g, 0.34 mmol) and 4-(bromomethyl)pyridine hydrobromide (0.104 g, 0.39 mmol) in DMF (2.0 mL), NaH (0.041 g, 1.0 mmol, 60% oil) was added at 0° C. The reaction mixture was allowed to warm to room temperature and stirred for 1 h. The reaction mixture was poured into a solution of NH$_4$Cl and extracted with EtOAc (3×50 mL). The organic layer was sequentially washed with brine (2×75 mL), dried over anhydrous Na$_2$SO$_4$, and concentrated in vacuo. The crude product was purified by column chromatography (SiO$_2$, hexane/EtOAc 70:30) to give 35 (0.12, 92%).

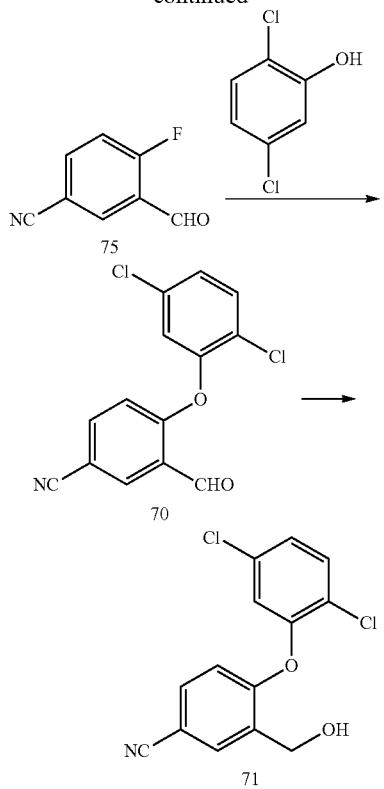

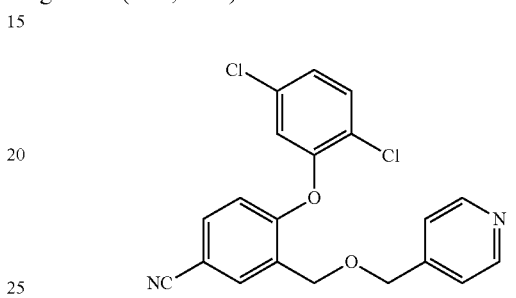

4-(2,5-dichlorophenoxy)-3-((pyridin-4-ylmethoxy) methyl)benzonitrile (35)

$^1$H NMR (500 MHz, CDCl$_3$) δ 8.60 (d, J=2.8 Hz, 2H), 7.91 (s, 1H), 7.54 (dd, J=5.6, 2.8 Hz, 1H), 7.43 (dt, J=8.7, 4.4 Hz, 1H), 7.34-7.24 (m, 2H), 7.22-7.16 (m, 1H), 7.07 (d, J=5.0 Hz, 1H), 6.68 (dd, J=8.5, 3.3 Hz, 1H), 4.73 (d, J=35.0 Hz, 4H). $^{13}$C NMR (126 MHz, CDCl$_3$) δ 157.19, 150.83, 149.97, 146.77, 133.71, 133.23, 133.03, 131.80, 129.34, 126.65, 124.93, 122.39, 121.73, 118.50, 115.72, 107.27, 71.36, 66.57, 14.20. HR-MS (ES) calcd for C$_{20}$H$_{14}$Cl$_2$N$_2$O$_2$ [M+1]$^+$ 385.0496. found 385.0511.

Synthesis of Compound 40

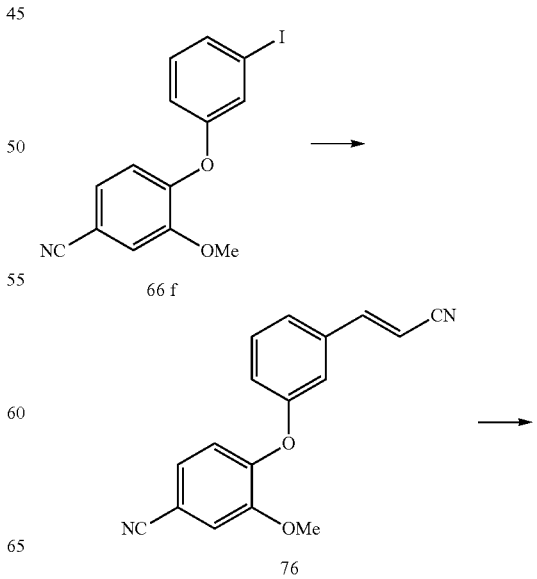

Step 1

A mixture of 74 (1.82 g, 9 mmol) and copper (I) cyanide (1.4 g, 15.7 mmol) in DMF (14.0 mL) was stirred at reflux overnight. After completion, the reaction mixture was cooled to rt and poured into a solution of water (10 mL) and NH$_4$OH (10 ml) followed by extraction with EtOAc (3×25 mL). The organic layer was sequentially washed with brine (2×15 mL), dried over anhydrous Na$_2$SO$_4$, and concentrated in vacuo to give 75$^{7a}$ (0.80 g, 60%).

Step 2

A mixture of 75 (0.8 g, 5.4 mmol), 2,5-dichlorophenol (0.98 g, 6.0 mmol) in DMSO (10.0 mL) and anhydrous K$_2$CO$_3$ (1.12 g, 8.1 mmol) was heated at 50° C. for 4 h. The mixture was poured into ice water extracted with EtOAc (3×50 mL). The organic layer was sequentially washed with brine (2×75 mL), dried over anhydrous Na$_2$SO$_4$, and concentrated in vacuo. The residue was purified by column chromatography to give 70 (1.40 g, 100%). $^1$H NMR (500 MHz, CDCl$_3$) δ 10.30 (s, 1H), 8.40 (d, J=2.7 Hz, 1H), 8.12 (d, J=7.9 Hz, 1H), 7.74 (m, 2H), 7.30 (d, J=8.7, 1H), 7.24 (s, 1H). HR-MS (ES) calcd for C$_{14}$H$_7$Cl$_2$NO$_2$ [M+1]$^+$ 293.0100. found 293.0102.

Step 3

To a solution of 70 (1.6 g, 5.4 mmol) in dry MeOH (10.0 mL), NaBH$_4$ (0.6 g, 16.2 mmol) was added in portions over period of 20 min at 0° C. After addition, the reaction mixture was stirred for 3 h at 0° C. The solution was poured into cold aqueous HCl and extracted with EtOAc (3×50 mL). The organic layer was sequentially washed with brine (2×75 mL), dried over anhydrous Na$_2$SO$_4$, and concentrated in vacuo to give 71 (1.4 g, 88%) which was used without further purification. HR-MS (ES) calcd for C$_{14}$H$_7$Cl$_2$NO$_2$ [M+1]$^+$ 295.3137. found 295.3137.

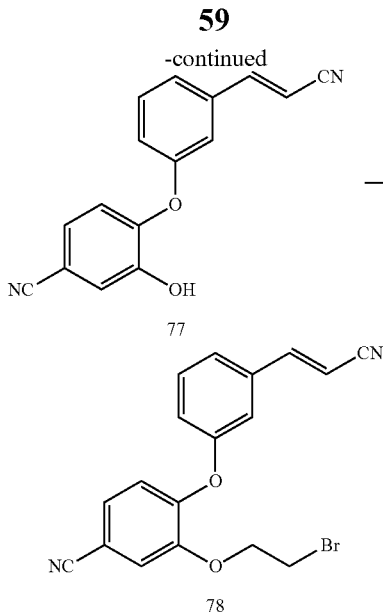

Step 1

A mixture of 57 (1.0 g, 5.8 mmol), 5-iodophenol (1.27 g, 5.8 mmol) in DMSO (10.0 mL) and anhydrous $K_2CO_3$ (1.2 g, 8.7 mmol) was heated at 110° C. for 1 h. The mixture was poured into ice water and extracted with EtOAc (3×50 mL). The organic layer was sequentially washed with brine (2×75 mL), dried over anhydrous $Na_2SO_4$, and concentrated in vacuo to give 3-(3-iodophenoxy)-4-methoxybenzonitrile (66 f) (1.76 g, 81%) which was used without further purification. HR-MS (ES) calcd for $C_{14}H_{10}INO_2$ $[M+1]^+$ 351.9803. found 351.9800.

Step 2

Acrylonitrile (2.9 mL, 5.6 mmol) was added to a mixture of 66 f (1 g, 2.8 mmol), $Et_3N$ (1.1 mL, 8.4 mmol), $PdCl_2(PPh_3)_3$ (0.29 g 0.45 mmol), and DMF (15.0 mL) under a nitrogen atmosphere at room temperature. The mixture was heated at 140° C. for 3 h. The reaction mixture was quenched with water and the mixture was extracted with EtOAc (3×50 mL). The organic layer was sequentially washed with brine (2×75 mL), dried over anhydrous $Na_2SO_4$, and concentrated in vacuo. The residue was purified by column chromatography ($SiO_2$, hexane/EtOAc 80:20) to give (Z)-4-(3-(2-cyanovinyl)phenoxy)-3-methoxybenzonitrile (0.17 g, 21%) and (E)-4-(3-(2-cyanovinyl)phenoxy)-3-methoxybenzonitrile (76) (0.42 g, 53%) $^1$H NMR (400 MHz, $CDCl_3$) δ 7.30 (dd, J=4.47, 7.59 Hz, 2H), 7.11-7.03 (m, 3H), 7.00-6.94 (m, 3H), 5.80 (d, J=16.64 Hz, 1H), 3.82 (s, 3H). HR-MS (ES) calcd for $C_{12}H_{12}N_2O_2$ $[M+1]^+$ 280.0133. found 280.0130.

Step 3

LiCl (0.5 g, 1.2 mmol) was added to a solution of 76 (1.1 g, 3.1 mmol) in DMF (20 mL). The reaction mixture was refluxed for 16 h. After cooling to rt, the reaction mixture was poured into water, acidified with 6 N HCl and extracted with EtOAc (3×50 mL). The organic layer was sequentially wash with brine (2×75 mL), dried over anhydrous $Na_2SO_4$, and concentrated in vacuo. The residue was purified by column chromatography ($SiO_2$, hexane/EtOAc 60:40) to give (E)-4-(3-(2-cyanovinyl)phenoxy)-3-hydroxybenzonitrile 77 (0.21 g, 21%) HR-MS (ES) calcd for $C_{16}H_{10}N_2O_2$ $[M+1]^+$ 263.001. found 263.000.

Step 4

77 (0.15 g, 5.7 mmol) was treated with $PPh_3$ (0.16 g, 6.3 mmol) and 2-bromoethanol (0.05 mL, 6.3 mmol) in dry THF (2 mL) and DIAD (0.12 mL, 6.2 mmol) as described above for the synthesis of 54 a-f, to give (E)-3-(2-bromoethoxy)-4-(3-(2-cyanovinyl)phenoxy)benzonitrile 78 (0.2 g, 71%) $^1$H NMR (500 MHz, $CDCl_3$) δ 7.43-7.35 (m, 2H), 7.34-7.28 (m, 1H), 7.28-7.21 (m, 2H), 7.04 (ddd, J=5.28, 8.26, 9.92 Hz, 3H), 5.87 (d, J=16.62 Hz, 1H), 4.33 (t, J=5.60 Hz, 2H), 3.55 (d, J=5.57 Hz, 2H).

Step 5

78 (0.2 g, 0.54 mmol), 3-benzoylpyrimidine-2,4(1H,3H)-dione (0.27 g, 0.59 mmol), anhydrous $K_2CO_3$ (0.72 g, 0.1 g) in DMF (4 mL) was stirred at rt overnight and 1 h at 60° C. to complete the reaction. The reaction mixture was poured into a solution of $NH_4Cl$ and extracted with EtOAc (3×20 mL). The organic layer was sequentially washed with brine (2×15 mL), dried over anhydrous $Na_2SO_4$, and concentrated in vacuo. The crude product was dissolved in MeOH (4.0 mL) and $NH_4OH$ (3.0 mL) was added. The reaction mixture was stirred at rt for 4 h. After completion, the reaction mixture was concentrated under reduced pressure and purified by column chromatography ($SiO_2$, hexane/EtOAc 20:80) to give 40 (0.05, 23%).

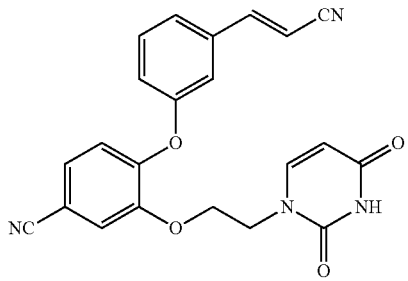 [SMILES: N#C/C=C/c1cccc(Oc2ccc(C#N)cc2OCCn2ccc(=O)[nH]c2=O)c1]

(E)-4-(3-(2-cyanovinyl)phenoxy)-3-(2-(2,4-dioxo-3,4-dihydropyrimidin-1(2H)-yl)ethoxy)benzonitrile
(40)

$^1$H NMR (500 MHz, MeOD) δ 7.45 (s, 1H), 7.38 (d, J=6.73 Hz, 1H), 7.29 (dd, J=8.94, 16.86 Hz, 2H), 7.23 (d, J=7.44 Hz, 1H), 7.06 (dd, J=8.05, 8.97 Hz, 2H), 6.99 (s, 1H), 6.85 (d, J=7.92 Hz, 1H), 6.10 (d, J=16.62 Hz, 1H), 5.17 (d, J=7.88 Hz, 1H), 4.20 (d, J=4.57 Hz, 2H), 4.00-3.90 (m, 2H). $^{13}$C NMR (126 MHz, $CDCl_3$) δ 158.01, 149.20, 147.13, 144.00, 143.79, 135.16, 122.67, 121.67, 120.20, 117.02, 116.90, 114.05, 111.46, 100.45, 98.25, 76.25, 76.00, 75.74, 65.60, 47.28, 28.68. FIR-MS (ES) calcd for $C_{22}H_{16}N_4O_4$ $[M+1]^+$ 401.1273. found 401.1271.

Synthesis of Compounds 41-42.

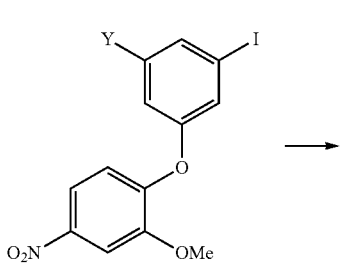

59 a Y = H
59 b Y = Cl

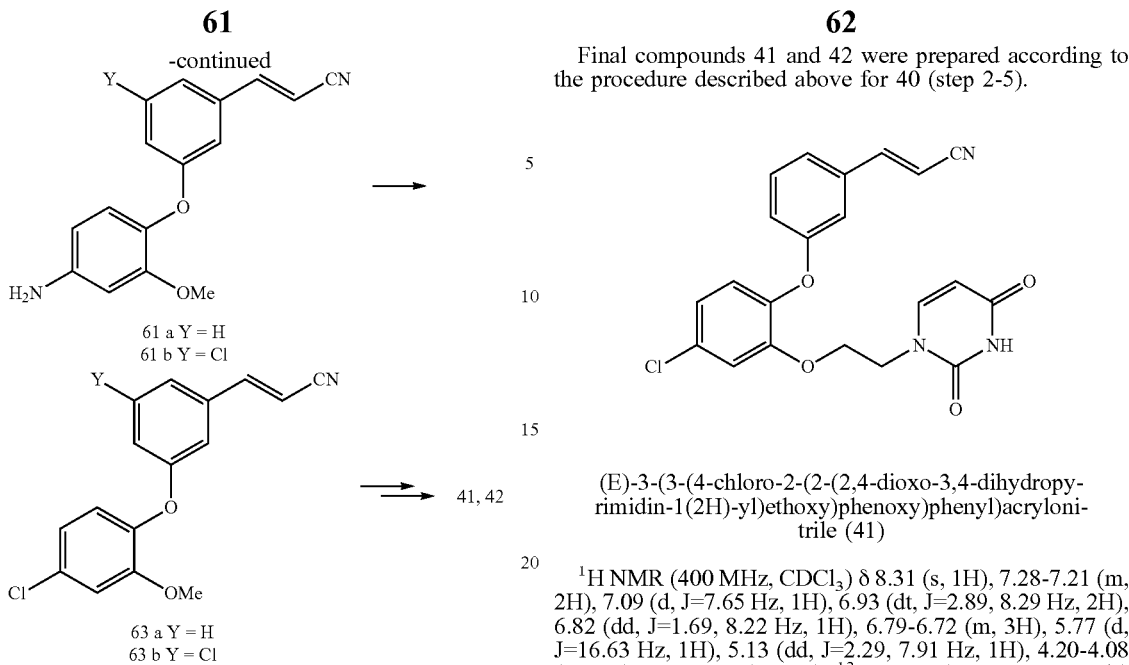

61 a Y = H
61 b Y = Cl 63 a Y = H
63 b Y = Cl

Compounds 59 a-b were prepared using the method described above for 66f (synthesis of 40, Step 1).

Starting with 55 (0.74 g, 4.3 mmol) and 5-iodophenol (0.93 g, 4.3 mmol) or 3-chloro-5-iodophenol[8a] (1.1 g, 4.3 mmol). 1-(3-iodophenoxy)-2-methoxy-4-nitrobenzene (59a) (1.70 g, 4.6 mmol) or 1-(3-chloro-5-iodophenoxy)-2-methoxy-4-nitrobenzene (59 b) (1.84 g, 4.6 mmol), Fe (2.0 g, 36.8 mmol) and a solution of $NH_4Cl$ (1.58, g in 11.0 mL $H_2O$, 18.4 mmol) were suspended in 60 mL of EtOH and heated at 75° C. for 6 h. The mixture was allowed to cool to room temperature; the suspended solid was filtered over celite and the filtrate was concentrated in vacuo. The residue was partitioned between EtOAc and water; combined organic extracts were dried over anhydrous $Na_2SO_4$ and concentrated in vacuo, to give 3-(3-iodophenoxy)-4-methoxyaniline (61a) (1.5 g, 83%) or 4-(3-chloro-5-iodophenoxy)-3-methoxyaniline (61b) (1.69 g, 100%). The crude of 61a or 61b (4.3 mmol) was suspended in concentrated HCl (6.5 mL) at 0° C. and stirred for 30 min. After this period, a solution of $NaNO_2$ in $H_2O$ (0.6 g in 4 mL, 8.8 mmol) was added dropwise. Then the resulting mixture was stirred for 1 h at rt. This solution was added over 30 min to a solution of CuCl (1.7 g, 17.2 mmol) in concentrated HCl (7.0 mL) at 60° C. After addition, the mixture was heated at 80° C. for 30 minutes. The mixture was allowed to cool to room temperature before addition of brine. The solution was extracted with ethyl acetate, dried over anhydrous $MgSO_4$ and evaporated in vacuo. The crude product was purified by column chromatography ($SiO_2$, hexane/EtOAc 100:0 to 80:20) to give 4-chloro-2-(3-iodophenoxy)-1-methoxybenzene (63a) (0.71 g, 45%) $^1H$ NMR (400 MHz, $CDCl_3$) δ 7.31-7.16 (m, 3H), 7.05 (d, J=7.66 Hz, 1H), 6.99-6.88 (m, 3H), 3.73 (s, 3H) HR-MS (ES) calcd for $C_{13}H_{10}ClIO_2$ [M+1]+ 359.0032. found 359.0033 or 4-chloro-1-(3-chloro-5-iodophenoxy)-2-methoxybenzene (63b) (0.67 g, 40%) $^1H$ NMR (500 MHz, $CDCl_3$) δ 7.19 (d, J=5.58 Hz, 1H), 7.17 (s, 1H), 7.03 (t, J=1.40 Hz, 1H), 6.94 (d, J=1.78 Hz, 1H), 6.93-6.88 (m, 2H), 6.81 (t, J=2.00 Hz, 1H), 6.79-6.75 (m, 1H), 3.73 (d, J=4.47 Hz, 3H). HR-MS (ES) calcd for $C_{13}H_9Cl_2IO_2$ [M+1]+ 395.7564. found 395.7563.

Final compounds 41 and 42 were prepared according to the procedure described above for 40 (step 2-5).

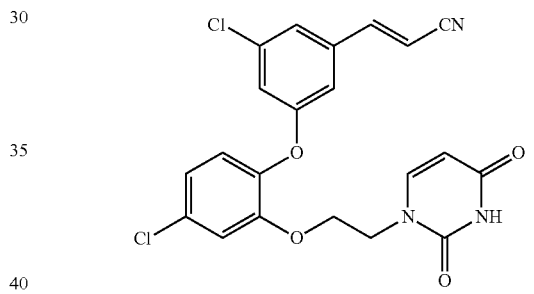

(E)-3-(3-(4-chloro-2-(2-(2,4-dioxo-3,4-dihydropyrimidin-1(2H)-yl)ethoxy)phenoxy)phenyl)acrylonitrile (41)

$^1H$ NMR (400 MHz, $CDCl_3$) δ 8.31 (s, 1H), 7.28-7.21 (m, 2H), 7.09 (d, J=7.65 Hz, 1H), 6.93 (dt, J=2.89, 8.29 Hz, 2H), 6.82 (dd, J=1.69, 8.22 Hz, 1H), 6.79-6.72 (m, 3H), 5.77 (d, J=16.63 Hz, 1H), 5.13 (dd, J=2.29, 7.91 Hz, 1H), 4.20-4.08 (m, 2H), 3.98-3.87 (m, 2H). $^{13}C$ NMR (126 MHz, $CDCl_3$) δ 163.09, 158.40, 150.60, 150.53, 149.53, 144.98, 142.08, 135.33, 131.16, 130.52, 123.45, 122.60, 118.40, 117.70, 115.09, 114.00, 101.51, 97.72, 66.86, 48.15, 29.7. HR-MS (ES) calcd for $C_{21}H_{16}ClN_3O_4$ [M+1]+ 410.0908. found 410.0921.

(E)-3-(3-chloro-5-(4-chloro-2-(2-(2,4-dioxo-3,4-dihydropyrimidin-1(2H)-yl)ethoxy)phenoxy)phenyl)acrylonitrile (42)

$^1H$ NMR (500 MHz, $CDCl_3$) δ 8.30 (s, 1H), 7.15 (s, 1H), 7.07 (s, 1H), 6.96 (dd, J=7.94, 13.60 Hz, 3H), 6.77 (dd, J=2.64, 8.11 Hz, 2H), 6.64 (s, 1H), 5.78 (d, J=16.60 Hz, 1H), 5.20 (d, J=7.90 Hz, 1H), 4.14 (d, J=4.08 Hz, 2H), 3.94 (s, 2H). $^{13}C$ NMR (126 MHz, $CDCl_3$) δ 158.01, 149.50, 147.13, 143.79, 135.16, 122.67, 121.67, 120.20, 117.02, 114.05, 111.46, 100.45, 98.25, 76.25, 76.00, 75.74, 65.60, 47.28, 28.68. HR-MS (ES) calcd for $C_{21}H_{15}Cl_2N_3O_4$ [M+1]+ 444.0552. found 444.0518.

Synthesis of Compound 43

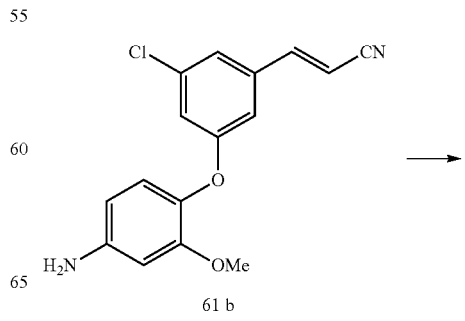

61 b

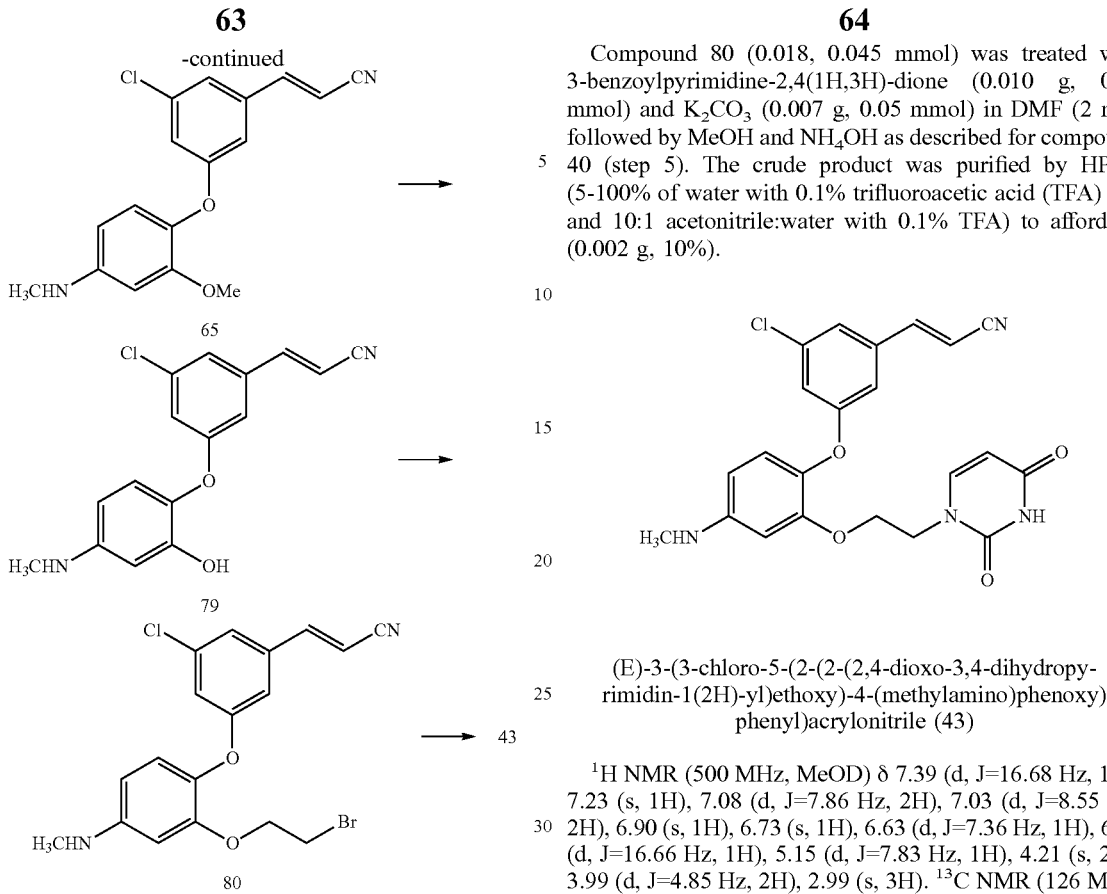

Compound 61b (0.15 g, 0.53 mmol), Cu(OAc)₂ (0.24 g, 1.33 mmol), pyridine (0.14 mL, 1.85 mmol) in dioxane (15 ml) was stirred for 15 min at rt. Then, methyl boronic acid (0.08 g, 1.33 mmol) was added and the reaction mixture was heated at reflux overnight. The reaction was cooled at rt, filtered through celite and concentrate under vacuo. The crude was purified by column chromatography (SiO₂, hexane/EtOAc 70:30) to give (E)-3-(3-chloro-5-(2-hydroxy-5-(methylamino)phenoxy)phenyl)acrylonitrile 65 (0.1 g, 55%). ¹H NMR (400 MHz, CDCl₃) δ 7.26 (d, J=3.19 Hz, 1H), 7.03 (t, J=1.60 Hz, 1H), 6.87 (ddd, J=1.86, 3.82, 18.08 Hz, 3H), 6.26 (d, J=2.58 Hz, 1H), 6.19 (dd, J=2.60, 8.56 Hz, 1H), 5.81 (d, J=16.61 Hz, 1H), 3.76 (s, 3H), 2.78 (s, 3H). 65 (0.091 g, 0.28 mmol) was treated with BBr₃ (0.84 mL, 0.84 mmol) as described above to give (E)-3-(3-chloro-5-(2-methoxy-4-(methylamino)phenoxy)phenyl)acrylonitrile (79) (0.056 g, 65%), ¹H NMR (500 MHz, CDCl₃) δ 7.22-7.16 (m, 3H), 7.03 (d, J=1.39 Hz, 1H), 6.94 (t, J=2.00 Hz, 1H), 6.84-6.81 (m, 1H), 6.74 (d, J=8.71 Hz, 1H), 6.28 (d, J=2.69 Hz, 1H), 6.13 (dd, J=2.72, 8.67 Hz, 1H), 5.76 (d, J=16.62 Hz, 1H), 2.78 (s, 3H).

Compound 79 (0.056 g, 0.18 mmol), Cs₂CO₃ (0.071 g, 0.22 mmol), 1,2 dibromoethane (0.06 mL, 0.23 mmol) in acetone was stirred at reflux for 15 h. The reaction mixture was filtered and the filtrate was concentrate under vacuum. The crude product was purified by column chromatography (SiO₂, hexane/EtOAc 70:30) to give (E)-3-(3-(2-(2-bromoethoxy)-4-(methylamino)phenoxy)-5-chlorophenyl)acrylonitrile (80) (0.018 g, 23%) ¹H NMR (500 MHz, CDCl₃) δ 7.20-7.16 (m, 2H), 6.79-6.72 (m, 1H), 6.18 (dt, J=2.22, 4.14 Hz, 2H), 5.75 (d, J=16.61 Hz, 1H), 4.16 (t, J=6.33 Hz, 2H), 3.38 (t, J=6.32 Hz, 2H), 2.79 (s, 3H).

Compound 80 (0.018, 0.045 mmol) was treated with 3-benzoylpyrimidine-2,4(1H,3H)-dione (0.010 g, 0.05 mmol) and K₂CO₃ (0.007 g, 0.05 mmol) in DMF (2 mL) followed by MeOH and NH₄OH as described for compound 40 (step 5). The crude product was purified by HPLC (5-100% of water with 0.1% trifluoroacetic acid (TFA) (A) and 10:1 acetonitrile:water with 0.1% TFA) to afford 43 (0.002 g, 10%).

(E)-3-(3-chloro-5-(2-(2-(2,4-dioxo-3,4-dihydropyrimidin-1(2H)-yl)ethoxy)-4-(methylamino)phenoxy)phenyl)acrylonitrile (43)

¹H NMR (500 MHz, MeOD) δ 7.39 (d, J=16.68 Hz, 1H), 7.23 (s, 1H), 7.08 (d, J=7.86 Hz, 2H), 7.03 (d, J=8.55 Hz, 2H), 6.90 (s, 1H), 6.73 (s, 1H), 6.63 (d, J=7.36 Hz, 1H), 6.19 (d, J=16.66 Hz, 1H), 5.15 (d, J=7.83 Hz, 1H), 4.21 (s, 2H), 3.99 (d, J=4.85 Hz, 2H), 2.99 (s, 3H). ¹³C NMR (126 MHz, CDCl₃) δ 163.55, 160.84, 151.16, 149.00, 145.45, 136.39, 133.68, 132.47, 129.06, 127.76, 124.11, 120.80, 118.09, 117.83, 112.47, 101.70, 98.94, 76.83, 66.61, 48.84, 31.31, 30.11. HR-MS (ES) calcd for C₂₂H₁₉ClN₄O₄ [M+1]⁺ 439.1078. found 439.1076.

Synthesis of Compound 44
Step 1

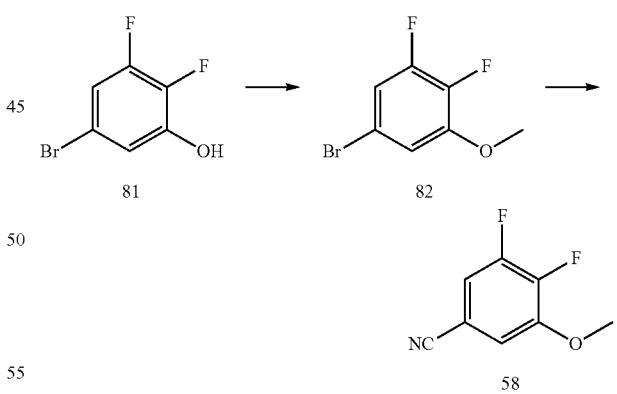

To a solution of 81 (1.5 g, 7.1 mmol) and K₂CO₃ (1.96 g, 14.2 mmol) in DMF (10 mL) was added iodomethane (0.49 mL, 7.8 mmol) dropwise at rt. The reaction mixture was heated at 45° C. overnight. After completion, EtOAc (10 mL) was added and the solution was filtered. The filtrate was washed with brine, dried over anhydrous MgSO₄ and evaporated in vacuo to give crude 82 (1.58 g, 100%). A solution of 82 (3.18 g, 14.26 mmol) and CuCN (1.27 g, 14.26 mmol) in DMF (30 mL) was heated at reflux under N₂ atmosphere for 6 h. After this period, the reaction mixture was diluted with EtOAc and washed with water (20 mL). The organic layer was washed with brine (2×15 mL), dried over anhydrous Na$_2$SO$_4$, and concentrated in vacuo. The crude product was purified by column chromatography (SiO$_2$, hexane/EtOAc 75:25) to give 58 (1.05 g, 43%). $^1$H NMR (400 MHz, CDCl$_3$) δ 7.29 (d, J=2.2 Hz, 1H), 6.90 (s, 1H), 3.89 (s, 3H). $^{13}$C NMR (126 MHz, CDCl$_3$) δ 151.16, 150.90, 149.00, 118.69, 116.33, 112.96, 110.09, 41.02.

Compound 44 was prepared according to the procedure described above for 28-32 (step 2-4).

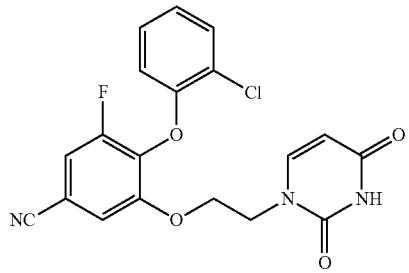 [SMILES: N#Cc1cc(F)c(Oc2ccccc2Cl)c(OCCn2ccc(=O)[nH]c2=O)c1]

4-(2-chlorophenoxy)-3-(2-(2,4-dioxo-3,4-dihydropyrimidin-1(2H)-yl)ethoxy)-5-fluorobenzonitrile 44

$^1$H NMR (500 MHz, CDCl$_3$) δ 8.14 (s, 1H), 7.41 (dt, J=7.7, 3.8 Hz, 1H), 7.17 (dd, J=8.8, 1.8 Hz, 1H), 7.07-6.91 (m, 3H), 6.80 (d, J=7.9 Hz, 1H), 6.45 (d, J=8.1 Hz, 1H), 5.27 (d, J=7.9 Hz, 1H), 4.22-4.07 (m, 2H), 4.01-3.89 (m, 2H). $^{13}$C NMR (126 MHz, CDCl$_3$) δ 163.27, 157.27, 155.25, 152.90, 150.72, 145.36, 131.36, 128.35, 124.63, 122.67, 115.25, 115.07, 114.65, 113.38, 110.03, 102.34, 67.97, 48.40. HR-MS (ES) calcd for C$_{19}$H$_{13}$ClFN$_3$O$_4$ [M+1]$^+$ 401.0579. found 401.0577.

Synthesis of Compound 45
Step 1

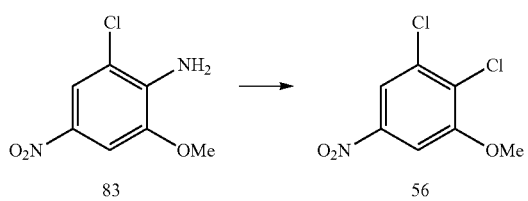 [SMILES: COc1cc([N+](=O)[O-])cc(Cl)c1N ; COc1cc([N+](=O)[O-])cc(Cl)c1Cl]

Compound 56 was prepared according to procedure described for 63a-b with 2-chloro-6-methoxy-4-nitroaniline (83) (2.62 g, 13 mmol), NaNO$_2$ (1.76 g, 26 mmol), CuCl (5.1 g, 39 mmol). (2.7 g, 94%): $^1$H NMR (400 MHz, CDCl$_3$) δ 7.88 (s, 1H), 7.66 (s, 1H), 3.89 (s, 3H).

Step 2

A solution of 56 (2.7 g, 12.2 mmol) in DMSO (10 mL) was treated with 2-chlorophenol (1.57 g, 12.2 mmol) and K$_2$CO$_3$ (1.69 g, 18.3 mmol) according to the procedure described for 66f. To afford 59 (2.5 g, 66%): $^1$H NMR (400 MHz, CDCl$_3$) δ 8.01 (s, 1H), 7.72 (s, 1H), 7.45 (dd, d, J=7.9 Hz, 1H), 7.22-6.99 (m, 3H), 3.89 (s, 3H).

Step 3

Compound 64 was prepared according to procedure described for 63 a-b. (1.5 g, 57%) $^1$H NMR (400 MHz, CDCl$_3$) δ 7.41 (dd, J=1.74, 7.74 Hz, 1H), 7.15 (d, J=2.20 Hz, 1H), 7.10-6.99 (m, 2H), 6.79 (d, J=2.20 Hz, 1H), 6.75 (dd, J=1.70, 7.94 Hz, 1H), 3.88 (s, 3H). HR-MS (ES) calcd for C$_{13}$H$_9$Cl$_3$O$_3$ [M+1]$^+$ 303.0129. found 303.0130.

Compound 45 was prepared according to the procedure described above for 28-32 (step 2-3). The uracil group was added as described for 40 (step 5).

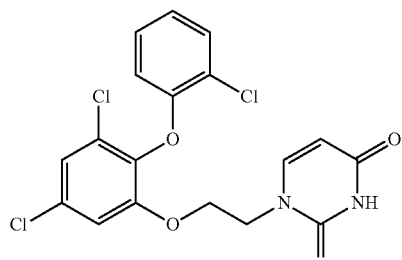

1-(2-(3,5-dichloro-2-(2-chlorophenoxy)phenoxy)ethyl)pyrimidine-2,4(1H,3H)-dione (45)

$^1$H NMR (400 MHz, CDCl$_3$) δ 7.84 (s, 1H), 7.41 (dd, J=1.74, 7.74 Hz, 1H), 7.10 (d, J=2.28 Hz, 1H), 7.06-6.90 (m, 2H), 6.81 (d, J=2.27 Hz, 1H), 6.75 (d, J=7.94 Hz, 1H), 6.34 (dd, J=1.48, 8.09 Hz, 1H), 5.20 (dd, J=2.38, 7.94 Hz, 1H), 4.13-4.06 (m, 2H), 3.93-3.87 (m, 2H). $^{13}$C NMR (126 MHz, CDCl$_3$) δ 163.00, 152.55, 151.93, 150.58, 144.90, 138.36, 131.66, 130.79, 130.11, 127.86, 123.46, 123.03, 121.87, 113.79, 112.99, 101.92, 67.26, 48.02. HR-MS (ES) calcd for C$_{18}$H$_{13}$Cl$_3$N$_2$O$_4$ [M+1]$^+$, 428.9964. found 428.9964.

Synthesis of Compound 46

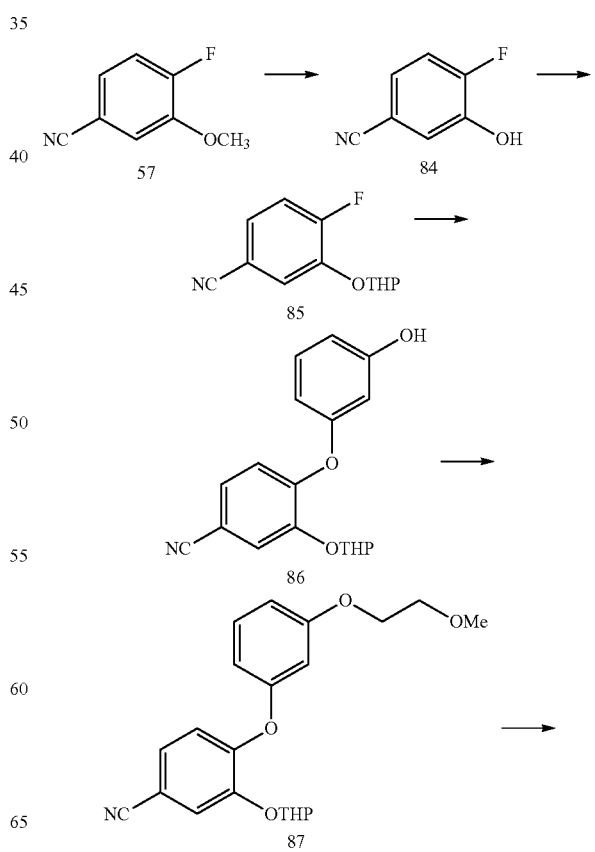

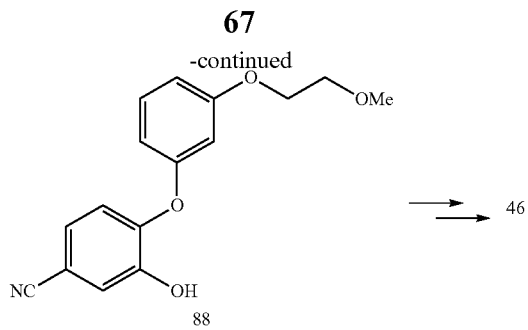

88

Compound 57 (3.0 g, 19.9 mmol) in DMF (25 mL) was treated with LiCl (3.36 g, 79.6 mmol) according to procedure described for compound 77, to give 4-fluoro-3-hydroxybenzonitrile 84 (2.6 g, 96%).

84 (2.6 g, 18.8 mmol) was dissolved in CH$_2$Cl$_2$ (5 mL) and 3,4-dihydro-2H-pyran (6 mL, 56 mmol) was added dropwise followed by pyridinium p-toluenesulfonate (0.4 g, 1.88 mmol) at 0° C. The reaction mixture was stirred at rt overnight. After completion, the reaction was quenched with water (5 mL) and EtOAC (10 mL). The aqueous layer was extracted with EtOAc (3×10 mL) and the combined organic layer was washed with brine (2×15 mL), dried over anhydrous Na$_2$SO$_4$, and concentrated in vacuo. The crude product was purified by column chromatography (SiO$_2$, hexane/EtOAc 80:20) to give 3-fluoro-4-((tetrahydro-2H-pyran-2-yl)oxy)benzonitrile (85) (3.52 g, 86%) $^1$H NMR (400 MHz, CDCl$_3$) δ 7.54 (d, J=7.58 Hz, 1H), 7.28 (dddd, J=3.13, 3.84, 9.10, 9.78 Hz, 1H), 7.22-7.10 (m, 1H), 5.47 (s, 1H), 4.13-3.90 (m, 2H), 2.18-1.86 (m, 2H), 1.86-1.68 (m, 2H), 1.68-1.33 (m, 2H).

85 (0.71 g, 3.27 mmol) was treated with resorcinol (0.39 g, 3.6 mmol) and K$_2$CO$_3$ (0.93 g, 6.54 mmol) in DMSO at 70° C. overnight. After completion, the reaction mixture was poured into ice water and was extracted with EtOAc (3×50 mL). The organic layer was sequentially washed with brine (2×75 mL), dried over anhydrous Na$_2$SO$_4$, and concentrated in vacuo. The residue was purified by column chromatography (SiO$_2$, hexane/EtOAc 60:40) to give 4-(3-hydroxyphenoxy)-3-((tetrahydro-2H-pyran-2-yl)oxy)benzonitrile (86) (0.21 g, 21%). $^1$H NMR (500 MHz, CDCl$_3$) δ 7.32-7.26 (m, 1H), 7.15 (d, J=9.90 Hz, 2H), 7.08 (dt, J=8.00, 15.34 Hz, 1H), 6.87-6.69 (m, 1H), 6.57 (s, 1H), 6.41 (d, J=10.03 Hz, 2H), 4.14 (d, J=7.12 Hz, 1H), 2.07-1.90 (m, 2H), 1.87 (dd, J=9.42, 26.70 Hz, 2H), 1.55 (s, 2H), 1.26 (dd, J=4.81, 9.43 Hz, 2H).

Compound 86 (0.21 g, 0.7 mmol), 1-chloro-2-methoxyethane (0.1 mL, 1 mmol), K$_2$CO$_3$ (0.14 g, 1 mmol) in acetonitrile was stirred at 80° C. for 72 h. The reaction mixture was diluted with EtOAc (5 mL) and washed with water (10 mL). The organic layer was washed with brine (2×15 mL), dried over anhydrous Na$_2$SO$_4$, and concentrated in vacuo. The crude product was purified by column chromatography (SiO$_2$, hexane/EtOAc 75:25) to give 87 (0.20 g, 80%) $^1$H NMR (500 MHz, CDCl$_3$) δ 7.52 (dd, J=1.90, 7.05 Hz, 1H), 7.29-7.26 (m, 1H), 7.21 (t, J=8.25 Hz, 1H), 7.09-7.01 (m, 1H), 6.75-6.67 (m, 1H), 6.58-6.51 (m, 2H), 4.11 (t, J=11.20 Hz, 2H), 3.84-3.69 (m, 3H), 3.38 (s, 3H), 2.03 (d, J=18.66 Hz, 2H), 1.83-1.43 (m, 6H).

A solution of 87 (0.20 g, 0.54 mmol) in MeOH (5 mL) was treated with VCl$_3$ (0.008 g, 0.054 mmol). The reaction mixture was stirred at rt for 30 min, filtered through celite and concentrated under vacuo. The crude was purified by column chromatography (SiO$_2$, hexane/EtOAc 70:30) to give 4-hydroxy-3-(3-(2-methoxyethoxy)phenoxy)benzonitrile 88 (0.06 g, 33%). $^1$H NMR (500 MHz, CDCl$_3$) δ 7.28 (dd, J=6.70, 8.65 Hz, 2H), 7.11 (s, 1H), 6.83 (d, J=8.41 Hz, 2H), 6.64 (d, J=2.31 Hz, 2H), 5.98 (s, 1H), 4.10 (dd, J=4.05, 5.15 Hz, 2H), 3.75 (dd, J=3.93, 5.24 Hz, 2H), 3.45 (s, 3H).

Compound 46 was obtained according to procedure described for 28-32 (step 2-3). The uracil group was added as described for 40 (step 5).

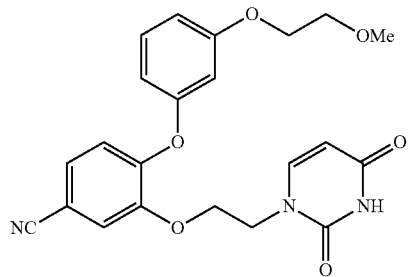 [SMILES: COCCOc1cccc(Oc2ccc(C#N)cc2OCCn2ccc(=O)[nH]c2=O)c1]

3-(2-(2,4-dioxo-3,4-dihydropyrimidin-1(2H)-yl)ethoxy)-4-(3-(2-methoxyethoxy)phenoxy)benzonitrile (46)

$^1$H NMR (500 MHz, CDCl$_3$) δ 8.47 (s, 1H), 7.31 (dd, J=8.3, 1.8 Hz, 1H), 7.22 (dd, J=13.3, 5.0 Hz, 2H), 7.04 (d, J=8.3 Hz, 1H), 6.97 (d, J=7.9 Hz, 1H), 6.68 (dd, J=8.1, 2.1 Hz, 1H), 6.50 (dd, J=7.9, 2.0 Hz, 1H), 6.41 (t, J=2.3 Hz, 1H), 5.38 (dd, J=7.9, 2.4 Hz, 1H), 4.27-4.20 (m, 2H), 4.09 (ddd, J=25.8, 6.9, 3.8 Hz, 4H), 3.78-3.73 (m, 2H), 3.46 (s, 3H). $^{13}$C NMR (126 MHz, CDCl$_3$) δ 163.05, 160.24, 157.42, 150.50, 149.98, 149.18, 145.21, 130.45, 127.23, 121.79, 118.21, 117.62, 109.79, 109.17, 108.27, 104.38, 101.67, 70.98, 67.39, 67.11, 59.23, 48.07. HR-MS (ES) calcd for C$_{22}$H$_{21}$N$_3$O$_6$ [M+1]$^+$ 424.2450. found 424.2448.

Synthesis of Compound 47

Step 1

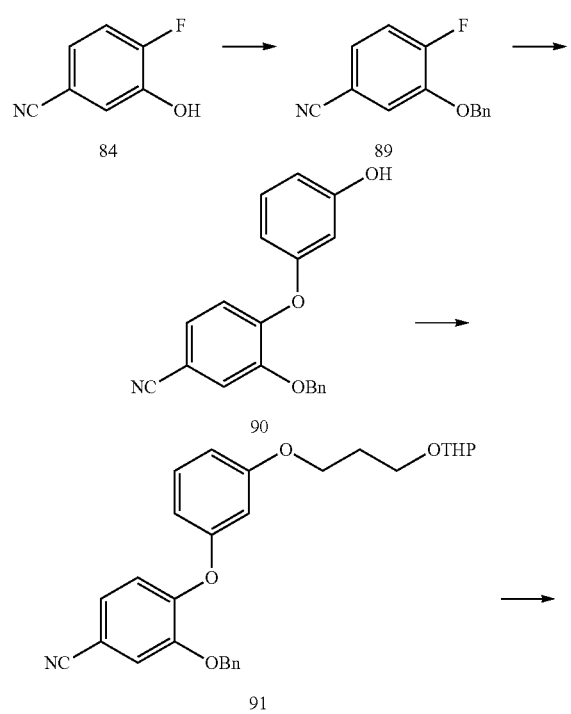

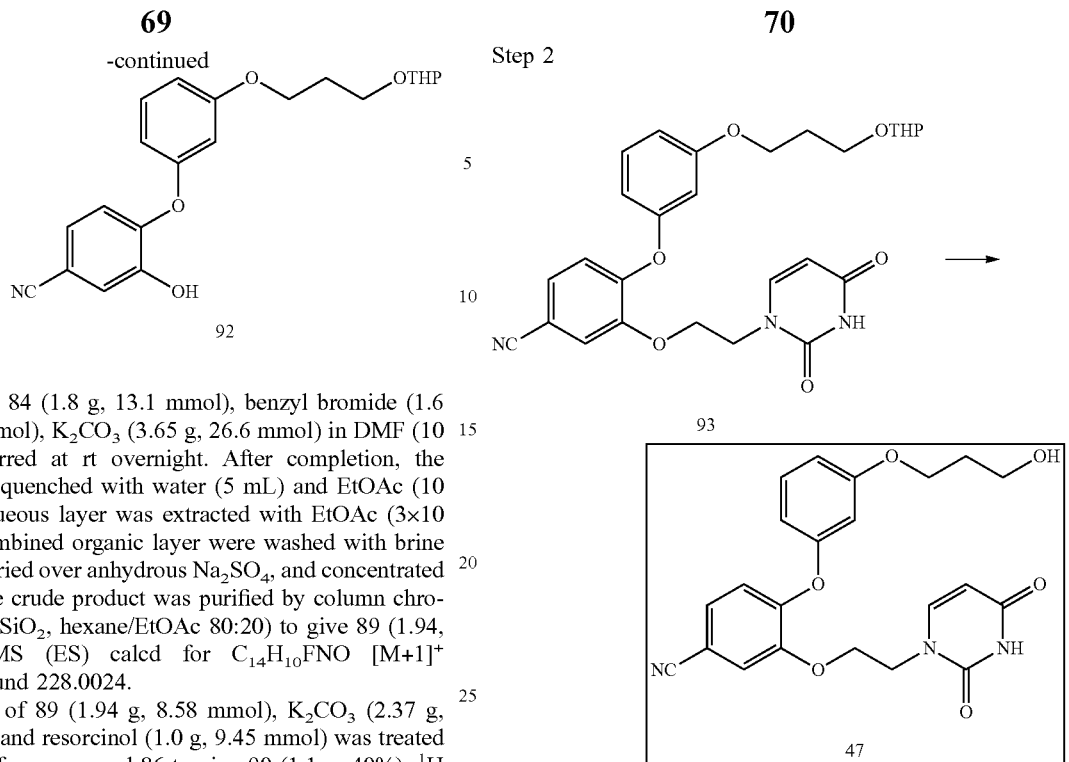

Compound 84 (1.8 g, 13.1 mmol), benzyl bromide (1.6 mL, 14.55 mmol), K$_2$CO$_3$ (3.65 g, 26.6 mmol) in DMF (10 mL) was stirred at rt overnight. After completion, the reaction was quenched with water (5 mL) and EtOAc (10 mL). The aqueous layer was extracted with EtOAc (3×10 mL). The combined organic layer were washed with brine (2×15 mL), dried over anhydrous Na$_2$SO$_4$, and concentrated in vacuo. The crude product was purified by column chromatography (SiO$_2$, hexane/EtOAc 80:20) to give 89 (1.94, 65%). HR-MS (ES) calcd for C$_{14}$H$_{10}$FNO [M+1]$^+$ 228.0023. found 228.0024.

A solution of 89 (1.94 g, 8.58 mmol), K$_2$CO$_3$ (2.37 g, 17.16 mmol) and resorcinol (1.0 g, 9.45 mmol) was treated as described for compound 86 to give 90 (1.1 g, 40%): $^1$H NMR (500 MHz, CDCl$_3$) δ 7.30 (dd, J=5.19, 7.84 Hz, 5H), 7.26-7.21 (m, 4H), 7.18 (dd, J=1.74, 8.24 Hz, 1H), 6.95 (t, J=8.80 Hz, 1H), 6.81-6.72 (m, 1H), 6.67-6.59 (m, 1H), 5.10 (s, 2H). HR-MS (ES) calcd for C$_{20}$H$_{15}$NO$_3$ [M+1]$^+$ 318.1593. found 318.1591.

A solution of 90 (0.42 g, 1.33 mmol), NaH (60% oil, 0.054 g, 2.26 mmol) in dry DMF was stirred under N$_2$ at 0° C. for 10 min. After this period, 2-(3-chloropropoxy)tetrahydro-2H-pyran (0.26 mL, 1.60 mmol) was added dropwise at the same temperature. The reaction mixture was allowed to warm at rt and stirred overnight. The mixture was poured into ice water and extracted with EtOAc (3×50 mL) the organic layer was sequentially washed with brine (2×75 mL), dried over anhydrous Na$_2$SO$_4$, and concentrated in vacuo. The residue was purified by column chromatography (SiO$_2$, hexane/EtOAc 80:20) to give 91 (0.62 g, 98%). $^1$H NMR (400 MHz, CDCl$_3$) δ 7.40-7.15 (m, 9H), 6.96 (d, J=8.25 Hz, 1H), 6.76 (dd, J=2.34, 8.23 Hz, 1H), 6.64 (d, J=2.29 Hz, 1H), 5.10 (s, 2H), 4.64-4.55 (m, 1H), 3.93-3.80 (m, 2H), 3.67 (t, J=6.42 Hz, 2H), 3.53 (dt, J=5.97, 9.97 Hz, 2H), 2.11-1.98 (m, 2H), 1.87-1.78 (m, 1H), 1.76-1.64 (m, 2H), 1.63-1.49 (m, 4H).

To a solution of 91 (0.62 g, 1.31 mmol) in MeOH (5 mL) and THF (5 mL) was added 10% palladium on carbon (0.07 g). The flask was evacuated and flushed with hydrogen two times and the reaction mixture stirred for two hours under hydrogen atmosphere. The completed reaction was diluted with ethyl acetate, filtered through celite, and partitioned between EtOAc and water washed with brine, dried over anhydrous Na$_2$SO$_4$, concentrated in vacuo. The residue was purified by column chromatography (SiO$_2$, Hexane/EtOAc 50:50) to afford 92 (0.57 g, 95%). $^1$H NMR (500 MHz, CDCl$_3$) δ 7.44 (dd, J=7.36, 15.61 Hz, 1H), 7.33 (d, J=1.95 Hz, 1H), 7.17 (dd, J=1.96, 8.40 Hz, 1H), 6.95-6.90 (m, 2H), 6.89 (d, J=8.40 Hz, 1H), 6.83 (dd, J=3.64, 5.95 Hz, 1H), 5.80 (s, 1H), 4.60 (s, 1H), 4.12 (d, J=7.17 Hz, 2H), 3.93-3.80 (m, 2H), 3.67 (t, J=6.39 Hz, 2H), 3.58-3.45 (m, 2H), 2.05 (dd, J=4.12, 8.23 Hz, 2H), 1.88-1.76 (m, 2H), 1.72 (ddd, J=4.76, 8.08, 12.80 Hz, 2H).

Compound 93 was obtained according to procedure described for 28-32 (step 2-3). The uracil group was added as described for 40 (step 5). Compound 47 was obtained by treatment of crude of 93 (0.010 g, 0.019 mmol) with VCl$_3$(0.001 g, 0.006 mmol) in MeOH (3 mL) as described for synthesis of compound 88. The crude product was purified by column chromatography (SiO$_2$, Hexane/EtOAc 10:90) to give 3-(2-(2,4-dioxo-3,4-dihydropyrimidin-1(2H)-yl)ethoxy)-4-(3-(3-hydroxypropoxy)phenoxy)benzonitrile (47) (0.034 g, 42%). $^1$H NMR (500 MHz, CDCl$_3$) δ 8.79 (s, 1H), 7.33 (dd, J=1.86, 8.27 Hz, 1H), 7.24 (d, J=1.76 Hz, 1H), 7.22 (d, J=8.24 Hz, 1H), 7.07 (d, J=8.26 Hz, 1H), 6.91 (d, J=7.91 Hz, 1H), 6.74-6.62 (m, 1H), 6.51 (ddd, J=0.70, 2.37, 8.18 Hz, 1H), 6.26 (t, J=2.34 Hz, 1H), 5.29 (d, J=7.90 Hz, 1H), 4.34-4.21 (m, 3H), 4.09-4.04 (m, 5H), 3.85 (t, J=5.39 Hz, 2H), 3.65 (s, 1H). $^{13}$C NMR (126 MHz, CDCl$_3$) δ 160.38, 157.63, 150.19, 145.30, 130.49, 127.35, 122.31, 117.85, 109.35, 109.03, 108.59, 103.46, 101.50, 67.10, 64.77, 59.11, 48.22, 31.81, 14.21. HR-MS (ES) calcd for C$_{22}$H$_{21}$N$_3$O$_6$ [M+1]$^+$ 423.1348. found 423.1350.

ABBREVIATIONS USED

HIV, human immunodeficiency virus; HIV-RT, HIV reverse transcriptase; NRTI, nucleoside inhibitor of HIV-RT; NNRTI, non-nucleoside inhibitor of HIV-RT; OPLS, optimized potentials for liquid simulations; OPLS-AA, OPLS all-atom; CM1A, charge model 1A; DIAD, diisopropyl azodicarboxylate.

REFERENCES

First Set (1) (a) Flexner, C. HIV drug development: the next 25 years. *Nature Rev. Drug Disc.* 2007, 6, 959-966. (b) De Clerq, E. The design of drugs for HIV and HCV. *Nature Rev. Drug*

(1) *Disc.* 2007, 6, 1001-1018. (c) Jochmans, D. Novel HIV-1 reverse transcriptase inhibitors. *Virus Res.* 2008, 134, 171-185.

(2) (a) Kohlstaedt L. A.; Wang J.; Friedman J. M.; Rice P. A.; Steitz T. A. Crystal Structure at 3.5 Å Resolution of HIV-1 Reverse Transcriptase Complexed with an Inhibitor. *Science* 1992, 256, 1783-1790. (b) For a review, see: Prajapati, D. G.; Ramajayam, R.; Yadav, M. R.; Giridhar, R. The search for potent, small molecule NNRTIs: A review. *Bioorg. Med. Chem.* 2009, 17, 5744-5762.

(3) (a) Adams, J.; Patel, N.; Mankaryous, N.; Tadros, M.; Miller, C. D. HIV/AIDS; Nonnucleoside Reverse Transcriptase Inhibitor Resistance and the Role of the Second-Generation Agents. *Ann. Pharmacotherapy* 2010, 44, 157-165. (b) Richman, D. D.; Margolis, D. M.; Delaney, M.; Greene, W. C.; Hazuda, D.; Pomerantz, R. J. The Challenge of Finding a Cure for HIV Infection. *Science* 2009, 323, 1304-1307.

(4) For a review, see: Jorgensen, W. L. Efficient Drug Lead Discovery and Optimization. *Acc. Chem. Res.* 2009, 42, 724-733.

(5) (a) Zeevaart, J. G.; Wang, L.; Thakur, V. V.; Leung, C. S.; Tirado-Rives, J.; Bailey, C. M.; Domaoal, R. A.; Anderson, K. S.; Jorgensen, W. L. Optimization of Azoles as Anti-HIV Agents Guided by Free-Energy Calculations. *J. Am. Chem. Soc.* 2008, 130, 9492-9499. (b) Leung, C. S.; Zeevaart, J. G.; Domaoal, R. A.; Bollini, M.; Thakur, V. V.; Spasov, K.; Anderson, K. S.; Jorgensen, W. L. Eastern extension of azoles as non-nucleoside inhibitors of HIV-1 reverse transcriptase; cyano group alternatives. *Bioorg. Med. Chem. Lett.* 2010, 20, 2485-2488.

(6) Nichols, S. E.; Domaoal, R. A.; Thakur, V. V.; Bailey, C. M.; Wang, L.; Tirado-Rives, J.; Anderson, K. S.; Jorgensen, W. L. Discovery of Wild-type and Y181C Mutant Non-nucleoside HIV-1 Reverse Transcriptase Inhibitors Using Virtual Screening with Multiple Protein Structures. *J. Chem. Inf. Model.* 2009, 49, 1272-1279.

(7) (a) Hopkins, A. L.; Ren, J.; Esnouf, R. M.; Willcox, B. E.; Jones, E. Y.; Ross, C.; Miyasaka, T.; walker, R. T.; Tanaka, H.; Stammers, D. K.; Stuart, D. I. Complexes of HIV-1 Reverse Transcriptase with Inhibitors of the HEPT Series Reveal Conformational Changes Relevant to the Design of Potent Non-Nucleoside Inhibitors. *J. Med. Chem.* 1996, 39, 1589-1600. (b) Ren, J.; Nichols, C.; Bird, L.; Chamberlain, P.; Weaver, K.; Short, S.; Stuart, D. I.; Stammers, D. K. *Structural mechanisms of drug resistance for mutations at codons 181 and 188 in HIV-1 reverse transcriptase and the improved resilience of second generation non-nucleoside inhibitors. J. Mol. Biol.* 2001, 312, 795-805.

(8) Himmel, D. M.; Das, K.; Clark, A. D.; Hughes, S. H.; Benjahad, A.; Oumouch, S.; Guillemont, J.; Coupa, S.; Poncelet, A.; Csoka, I.; Meyer, C.; Andries, K.; Nguyen, C. H.; Grierson, D. S.; Arnold, E. Crystal structures for HIV-1 reverse transcriptase in complexes with three pyridinone derivatives: a new class of non-nucleoside inhibitors effective against a broad range of drug-resistant strains. *J. Med. Chem.* 2005, 48, 7582-7591.

(9) Baba, M.; Tanaka, H.; Miyasaka, T.; Yuasa, S.; Ubasawa, M.; De Clercq, E. Hept derivatives: 6-Benzyl-1-ethoxymethyl-5-isopropyluracil (MKC-442). *Nucleosides Nucleotides* 1995, 14, 575-583.

(10) Jorgensen, W. L. *QikProp, v 3.0*; Schrödinger LLC: New York, 2006.

(11) McKay, A. F.; Baker, H. A.; Gaudry, R.; Garmaise, D. L.; Ranz R. J. Bacteriostats. VII. Substituted Benzylphenols. *J. Med. Chem.* 1963, 6, 816-817.

(12) Langer, R; Buysch, H. J. Verfahren zur Monobenzylierung von p-substituierten Phenolen. 1993, EP0538704.

(13) Novikov, M. S.; Ozerov, A. A. The Silyl Method for the Synthesis of 1[-2(Phenoxy)ethyl]uracils. *Chem. Het. Comp.* 2005, 41, 905-908.

(14) Frieden, M.; Giraud, M.; Reese, C. B.; Song, Q. Synthesis of 1-[cis-3-(hydroxymethyl)cyclobutyl]-uracil, -thymine and -cytosine. *J. Chem. Soc. Perkin Trans.* 1998, 1, 2827-2832.

(15) Reese, C. B.: Stewart, J. C. M. Methoxyacetyl as a protecting group in ribonucleoside chemistry. *Tetrahedron Lett.* 1968, 40, 4273-4276.

(16) Lin, T. S.; Luo, M. Z.; Liu, M. C.; Pai, S. B.; Dutschman, G. E.; Cheng, Y. C. Antiviral activity of 2',3'-dideoxy-β-L-5-fluorocytidine (β-L-EddC) and 2',3'-dideoxy-β-L-cytidine (β-L-ddC) against hepatitis B virus and human immunodeficiency virus type 1 in vitro. *Biochem. Pharmacol.* 1994, 47, 171-174.

(17) Ray, A. S.; Yang, Z.; Chu, C. K.; Anderson, K. S. Novel use of a guanosine prodrug approach to convert 2',3'-didehydro-2',3'-dideoxyguanosine into a viable antiviral agent. *Antimicrob. Agents Chemother.* 2002, 46, 887-891.

(18) Jorgensen, W. L.; Tirado-Rives, J. Molecular Modeling of Organic and Biomolecular Systems Using BOSS and MCPRO. *J. Comput. Chem.* 2005, 26, 1689-1700.

(19) For a review, see: Jorgensen, W. L.; Thomas, L. T. Perspective on Free-Energy Perturbation Calculations for Chemical Equilibria. *J. Chem. Theory Comput.* 2008, 4, 869-876.

(20) Jorgensen, W. L.; Maxwell, D. S.; Tirado-Rives, J. Development and Testing of the OPLS All-Atom Force Field on Conformational Energetics and Properties of Organic Liquids. *J. Am. Chem. Soc.* 1996, 118, 11225-11236.

(21) Jorgensen, W. L.; Tirado-Rives, J. Potential energy functions for atomic-level simulations of water, and organic and biomolecular systems. *Proc. Natl. Acad. Sci. U.S.A.* 2005, 102, 6665-6670.

(22) Jorgensen, W. L.; Chandrasekhar, J.; Madura, J. D.; Impey, R. W.; Klein, M. L. Comparison of Simple Potential Functions for Simulating Liquid Water. *J. Chem. Phys.* 1983, 79, 926-935.

(23) Tanaka, H.; Takashima, H.; Ubasawa, M.; Sekiya, K.; Inouye, N.; Baba, M.; Shigeta, S.; Walker, R. T.; De Clerq, E.; Miyasaka, T. Synthesis and Antiviral Activity of 6-Benzyl Analogs of 1-[(2-Hydroxyethoxy)methyl]-5-(phenylthio)thymine (HEPT) as Potent and Selective Anti-HIV-1 Agents. *J. Med. Chem.* 1995, 38, 2860-2865.

(24) Benjahad, A.; Guillemont, J.; Andries, K.; Nguyen, C. H.; Grierson, D. S. 3-Iodo-4-phenoxypyridinones (IOPY's), a new family of highly potent non-nucleoside inhibitors of HIV-1 reverse transcriptase. *Bioorg. Med. Chem. Lett.* 2003, 13, 4309-4312.

(25) Brameld, K. A.; Kuhn, B.; Reuter, D. C.; Stahl, M. Small Molecule Conformational Preferences Derived from Crystal Structure Data. A Medicinal Chemistry Focused Analysis. *J. Chem. Inf. Model.* 2008, 48, 1-24.

(26) Pierce, A. C.; Rao, G.; Bemis, G. W. BREED: Generating Novel Inhibitors through Hybridization of Known Ligands. Application to CDK2, P38, and HIV Protease. *J. Med. Chem.* 2004, 47, 2768-2775.

(27) Jorgensen, W. L.; Bollini, M.; Thakur, V. V.; Domaoal, R. A.; Spasov, K.; Anderson, K. S., Efficient Discovery of Potent Anti-HIV Agents Targeting the Tyr181Cys Variant of HIV Reverse Transcriptase, *J. Am. Chem. Soc.* 2011, 133, 0000-0000. In ASAP.

(28) Janssen, P. A. J.; Lewi, P. J.; Arnold, E.; Daeyaert, F.; de Jonge, M.; Heeres, J.; Koymans, L.; Vinkers, M.; Guillemont, J.; Pasquier, E.; Kukla, M.; Ludovici, D.; Andries, K.; de Bethune, M.-P.; Pauwels, R.; Das, K.; Clark, A. D., Jr.; Frenkel, Y. V.; Hughes, S. H.; Medaer, B.; De Knaep, F.; Bohets, H.; De Clerck, F.; Lampo, A.; Williams, P. & Stoffels, P. In search of a novel anti-HIV drug: multidisciplinary coordination in the discovery of 4-[[4-[[4-[(1E)-2-cyanoethenyl]-2,6-dimethylphenyl]amino]-2-pyrimidinyl]amino]benzonitrile (R278474, rilpivirine). *J. Med. Chem.* 2005, 48, 1901-1919. (b) Das, K.; Bauman, J. D.; Clark, A. D., Jr.; Frenkel, Y. V.; Lewi, P. J.; Shatkin, A. J.; Hughes, S. H.; Arnold, E. High-resolution structures of HIV-1 reverse transcriptase/TMC278 complexes: Strategic flexibility explains potency against resistance mutations. *Proc. Nat. Acad. Sci. USA* 2008, 105, 1466-1471.

(29) For a review, see: Politzer, P.; Murray, J. S.; Clark, T. Halogen bonding: an electrostatically-driven highly directional noncovalent interaction. *Phys. Chem. Chem. Phys.* 2010, 12, 7748-7757.

(30) Ibrahim, M. A. A. Molecular Modeling Study of Halogen Bonding in Drug Discovery. *J. Comput. Chem.* 2011, 32, 2564-2574.

(31) Hardegger, L. A.; Kuhn, B.; Spinnler, B.; Anselm, L.; Ecabert, R.; Stihle, M.; Gsell, B.; Thoma, R.; Diez, J.; Benz, J.; Plancher, J.-M.; Hartmann, G.; Banner, D. W.; Haap, W.; Diederich, F. *Angew. Chem. Int. Ed.* 2011, 50, 314-318.

(32) Tucker, T. J.; Saggar, S.; Sisko, J. T.; Tynebor, R. M.; Williams, T. M.; Felock, P. J.; Flynn, J. A.; Lai, M.-T.; Liang, Y.; McGaughey, G.; Liu, M.; Miller, M.; Moyer, G.; Munshi, V.; Perlow-Poehnelt, R.; Prasad, S.; Sanchez, R.; Torrent, M.; Vacca, J. P.; Wan, B.-L.; Yan. Y. The design and synthesis of diaryl ether second generation HIV-1 non-nucleoside reverse transcriptase inhibitors (NNRTIs) with enhanced potency versus key clinical mutations. *Bioorg. Med. Chem. Lett.* 2008, 18, 2959-2966.

(33) (a) Sweeney, Z. K.; Harris, S. F.; Arora, N.; Javanbakht, H.; Li, Y.; Fretland, J.; Davidson, J. P.; Billedeau, J. R.; Gleason, S. K.; Hirschfeld, D.; Kennedy-Smith, J. J.; Mirzadegan, T.; Roetz, R.; Smith, M.; Sperry, S.; Suh, J. M.; Wu, J.; Tsing, S.; Villasenor, A. G.; Paul, A.; Su, G.; Heilek, G.; Hang, J. Q.; Zhou, A. S.; Jernelius, J. A.; Zhang, F.-J.; Klumpp, K. Design of annulated pyrazoles as inhibitors of HIV-1 reverse transcriptase. *J. Med. Chem.* 2008, 51, 7449-7458. (b) Sweeney, Z. K.; Acharya, S.; Briggs, A.; Dunn, J. P.; Elworthy, T. R.; Fretland, J.; Giannetti, A. M.; Heilek, G.; Li, Y.; Kaiser, A. C.; Martin, M.; Saito, Y. D.; Smith, M.; Suh, J. M.; Swallow, S.; Wu, J.; Hang, J. Q.; Zhou, A. S.; Klumpp, K. Discovery and optimization of pyridazinone non-nucleoside inhibitors of HIV-1 reverse transcriptase. *Bioorg. Med. Chem. Lett.* 2008, 18, 4352-4354.

(34) Pelemans H.; Esnouf R.; De Clercq E.; Balzarini *J. Mol Pharmacol.* 2000 57, 54-60.

(35) Auwerx J.; Van Nieuwenhove J.; Rodríguez-Barrios F.; de Castro S.; Velázquez S.; Ceccherini-Silberstein F.; De Clercq E.; Camarasa M J.; Perno C F.; Gago F.; Balzarini J. *FEBS Lett.* 2005, 579, 2294-300.

REFERENCES

Second Set—Chemistry Experimental Section

1a McKay, A. F.; Baker, H. A.; Gaudry, R.; Garmaise, D. L.; Ranz R. J. Bacteriostats. VII. Substituted Benzylphenols. *J. Med. Chem.* 1963, 6, 816-817.

2a Langer, R; Buysch, H. J. Verfahren zur Monobenzylierung von p-substituierten Phenolen. 1993, EP0538704.

3a Novikov, M.; Ozerov, A., The Silyl Method for the Synthesis of 1[-2(Phenoxy)ethyl]uracils. *Chem Het Comp* 2005, 41, (7), 905-908.

4a Nichols, S. E.; Domaoal, R. A.; Thakur, V. V.; Tirado-Rives, J.; Anderson, K. S.; Jorgensen, W. L., Discovery of wild-type and Y181C mutant non-nucleoside HIV-1 reverse transcriptase inhibitors using virtual screening with multiple protein structures. *J Chem Inf Model* 2009, 49, (5), 1272-9.

5a Nerdinger, S.; Kendall, C.; Cai, X.; Marchart, R.; Riebel, P.; Johnson, M. R.; Yin, C. F.; Eltis, L. D.; Snieckus, V., Combined Directed ortho Metalation/Suzuki-Miyaura Cross-Coupling Strategies. Regiospecific Synthesis of Chlorodihydroxybiphenyls and Polychlorinated Biphenyls. *J Org Chem* 2007, 72, (16), 5960-5967.

6a Katz, L.; Cohen, M. S., Benzoxazol Derivatives. I. 2-Mercaptobenzoxazoles. *J Org Chem* 1954, 19, (5), 758-766.

7a Halley, F.; Sava, X., Synthesis of 5-Cyanoindazole and 1-Methyl and 1-Aryl-5-Cyanoindazoles. *Synthetic Communications* 1997, 27, (7), 1199-1207.

8a Jorgensen, W. L.; Bollini, M.; Thakur, V. V.; Domaoal, R. A.; Spasov, K.; Anderson, K. S., Efficient Discovery of Potent Anti-HIV Agents Targeting the Tyr181Cys Variant of HIV Reverse Transcriptase, submitted for publication.

9a Zbinden, K. G.; Banner, D. W.; Hilpert, K.; Himber, J.; Lavé, T.; Riederer, M. A.; Stahl, M.; Tschopp, T. B.; Obst-Sander, U., Dose-dependent antithrombotic activity of an orally active tissue factor/factor VIIa inhibitor without concomitant enhancement of bleeding propensity. *Bioorg. Med. Chem.* 2006, 14, (15), 5357-5369.

We claim:
1. A compound according to the chemical structure:

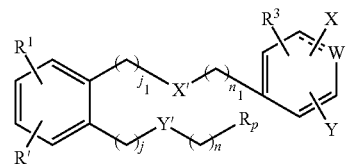

wherein $R^1$ is H, OH, a halogen, CN, $NO_2$, morpholinylethoxy, an optionally substituted alkyl group, an optionally substituted $C_2$-$C_6$ alkene group, an optionally substituted $C_2$-$C_6$ alkyne group, —$(CH_2)_m$—$NR^AR^B$, —$(CH_2)_m$—$C(O)NR^AR^{B1}$, —$(CH_2)_m$—$NR^AC(O)R^C$, —$(CH_2)_m$—O—$(C_1$-$C_6)$ alkyl which is optionally substituted, —O—$(CH_2)_m$—O—$(C_1$-$C_6)$ alkyl which is optionally substituted, —$(CH_2)_m$—O—$(CH_2)_m$—O—$(C_1$-$C_6)$ alkyl which is optionally substituted, —$(CH_2)_m$—C(O)—$(C_1$-$C_6)$ alkyl which is optionally substituted, —$(CH_2)_m$—OC(O)—$C_1$-$C_6$ alkyl which is optionally substituted, or —$(CH_2)_m$—C(O)O—$C_1$-$C_6$ alkyl which is optionally substituted;

$R^A$ and $R^B$ are each independently H or an optionally substituted $C_1$-$C_6$ alkyl group;

$R^{B1}$ is H, an optionally substituted $C_1$-$C_6$ alkyl group or an optionally substituted —$(CH_2)_m$—O—$(C_1$-$C_6)$ alkyl group;

R$^C$ is H, an optionally substituted C$_1$-C$_6$ alkyl group, or an optionally substituted —(CH$_2$)$_m$—O—(C$_1$-C$_6$) alkyl group;

R' is H, OH, a halogen, CN, NO$_2$, an optionally substituted C$_1$-C$_6$ alkyl group, —(CH$_2$)$_m$—O—(C$_1$-C$_6$) alkyl which is optionally substituted, —O—(CH$_2$)$_m$—O—(C$_1$-C$_6$) alkyl which is optionally substituted, —(CH$_2$)$_m$—C(O)—(C$_1$-C$_6$) alkyl which is optionally substituted, —(CH$_2$)$_m$—OC(O)—C$_1$-C$_6$ alkyl which is optionally substituted, or —(CH$_2$)$_m$—C(O)O—C$_1$-C$_6$ alkyl which is optionally substituted;

X' and Y' are each independently a bond (absent), O, S, S(O) (sulfoxide) or S(O)(O)(sulfone);

R$^3$ is H, OH, a C$_1$-C$_3$ alkyl group which is optionally substituted with up to three halogens, —O—C$_1$-C$_3$ alkyl, which is optionally substituted with up to three halogens, a halogen, NO$_2$ or CN;

j, j$_1$, m, n and n$_1$ are each independently 0, 1, 2 or 3;

X and Y are each independently H, OH, a halogen, CN, NO$_2$, an optionally substituted C$_1$-C$_6$ alkyl group, an optionally substituted C$_2$-C$_6$ alkene group, an optionally substituted C$_2$-C$_6$ alkyne group, —(CH$_2$)$_m$—NR$^A$R$^B$, —(CH$_2$)$_m$—C(O)NR$^A$R$^{B1}$, —(CH$_2$)$_m$—NR$^A$C(O)R$^C$, —(CH$_2$)$_m$—O—(C$_1$-C$_6$) alkyl which is optionally substituted, —O—(CH$_2$)$_m$—O—(C$_1$-C$_6$) alkyl which is optionally substituted, —(CH$_2$)$_m$—C(O)—(C$_1$-C$_6$) alkyl which is optionally substituted, —(CH$_2$)$_m$—OC(O)—C$_1$-C$_6$ alkyl which is optionally substituted, or —(CH$_2$)$_m$—C(O)O—C$_1$-C$_6$ alkyl which is optionally substituted, or X and Y, together with W, form an optionally substituted pyrrole ring, an optionally substituted dihydrofuran ring or an optionally substituted dihydropyrrole ring;

W is N or C, wherein when W is N, W, X and Y together form an optionally substituted five-membered pyrrole ring and when W is C, C is optionally substituted with X, Y or R$^3$, or alternatively, W, X and Y form an optionally substituted dihydrofuran ring or an optionally substituted dihydropyrrole ring; and R$_p$ is an optionally substituted C$_1$-C$_6$ alkyl group or an optionally substituted 6 membered heteroaryl group, or a pharmaceutically acceptable salt, enantiomer, stereoisomer, solvate or polymorph thereof.

2. The compound according to claim 1 wherein R$^1$ and is H, halogen, CN, NO$_2$, NH$_2$, NHCH$_3$, or morpholinylethoxy.

3. The compound according to claim 1 wherein either of R$^1$ or R' is H.

4. The compound according to claim 1 wherein R$^1$ and R' are each independently H or a halogen.

5. The compound according to claim 4 wherein R$^1$ is Cl or F and R' is H.

6. The compound according to claim 1 wherein X and Y are each independently H, halogen, CN, NO$_2$, (E)-cyanovinyl, methoxyethoxy or 3-hydroxypropan-1-oxy.

7. The compound according to claim 1 wherein X' and Y' are both O, j, j$_1$ and n$_1$ are each 0 and n is 1 or 2.

8. The compound according to claim 1 wherein Rp is a pyrimidine group attached at the N-1 position of the pyrimidine group and contains a substituent R$^{2a}$, attached at the 5- or 6-position of the pyrimidine group, wherein the R$^{2a}$ is H, CH$_3$, F, Cl, Br or I.

9. The compound according to claim 1 wherein Rp is a uracil group attached at the N-1 position of the uracil group and contains a substituent R$^{2a}$, attached at the 5-position of the uracil group, wherein the R$^{2a}$ is H or CH$_3$.

10. The compound according to claim 1 wherein the compound is

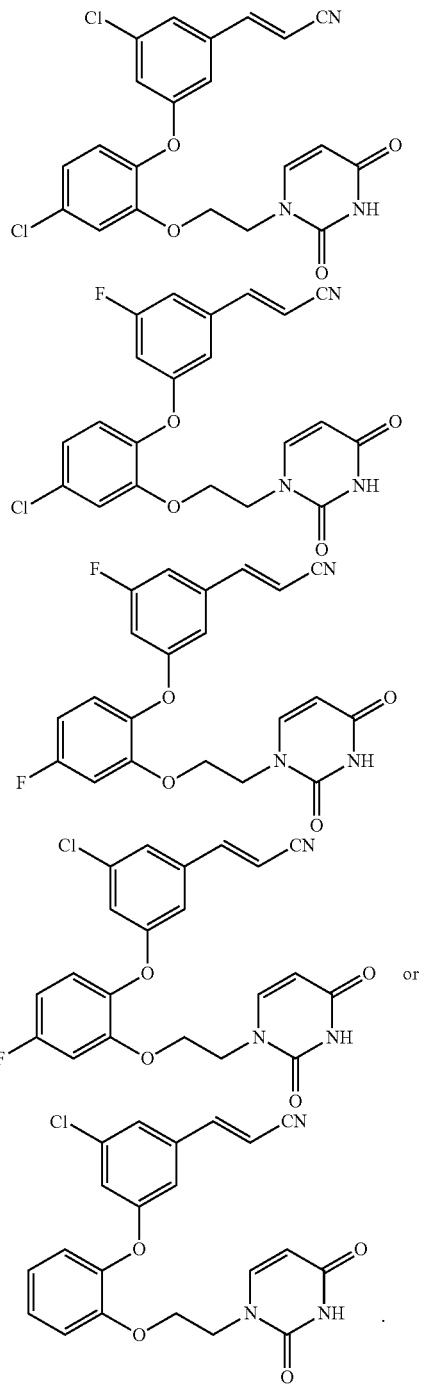

or

11. A compound according to the chemical structure:

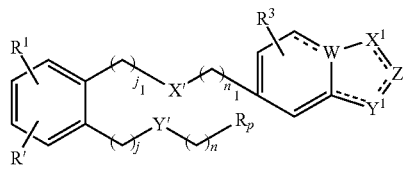

wherein W is N or C;

R¹ is H, OH, a halogen, a morpholinylethoxy group, an optionally substituted alkyl group, an optionally substituted $C_2$-$C_6$ alkene group, an optionally substituted $C_2$-$C_6$ alkyne group, —$(CH_2)_m$—$NR^A R^B$, —$(CH_2)_m$—$C(O)NR^A R^{B1}$, —$(CH_2)_m$—$NR^A C(O)R^C$, —$(CH_2)_m$—O—($C_1$-$C_6$) alkyl which is optionally substituted, —O—$(CH_2)_m$—O—($C_1$-$C_6$) alkyl which is optionally substituted, —$(CH_2)_m$—O—$(CH_2)_m$—O—($C_1$-$C_6$) alkyl which is optionally substituted, —$(CH_2)_m$—C(O)—($C_1$-$C_6$) alkyl which is optionally substituted, —$(CH_2)_m$—OC(O)—$C_1$-$C_6$ alkyl which is optionally substituted, or —$(CH_2)_m$—C(O)O—$C_1$-$C_6$ alkyl which is optionally substituted;

$R^A$ and $R^B$ are each independently H or an optionally substituted $C_1$-$C_6$ alkyl group;

$R^{B1}$ is H, an optionally substituted $C_1$-$C_6$ alkyl group, or an optionally substituted —$(CH_2)_m$—O—($C_1$-$C_6$) alkyl group;

$R^C$ is H, an optionally substituted $C_1$-$C_6$ alkyl group or an optionally substituted —$(CH_2)_m$—O—($C_1$-$C_6$) alkyl group;

R' is H, OH, a halogen, CN, $NO_2$, an optionally substituted $C_1$-$C_6$ alkyl group, —$(CH_2)_m$—O—($C_1$-$C_6$) alkyl which is optionally substituted, —O—$(CH_2)_m$—O—($C_1$-$C_6$) alkyl which is optionally substituted, —$(CH_2)_m$—C(O)—($C_1$-$C_6$) alkyl which is optionally substituted, —$(CH_2)_m$—OC(O)—$C_1$-$C_6$ alkyl which is optionally substituted, or —$(CH_2)_m$—C(O)O—$C_1$-$C_6$ alkyl which is optionally substituted;

X' and Y' are each independently a bond (absent), O, S, S(O) (sulfoxide) or S(O)(O)(sulfone);

$R^3$ is H, OH, a $C_1$-$C_3$ alkyl group which is optionally substituted with up to three halogens, —O—$C_1$-$C_3$ alkyl which is optionally substituted with up to three halogens, a halogen, $NO_2$ or CN;

$j, j_1, m, n$ and $n_1$ are each independently 0, 1, 2 or 3;

$X^1$ is

or N—$R^X$ when W is C, or

when W is N;

Z is

Y¹ is

O or N—$R^Y$ when W is C, or

when W is N;

$R^2$ is H, a $C_1$-$C_3$ alkyl optionally substituted with up to three fluorines, CN or halogen; and $R^X$ and $R^Y$ are each independently H or a $C_1$-$C_6$ alkyl (or a $C_1$-$C_3$ alkyl) group, optionally substituted with one or two hydroxyl groups, and $R_p$ is an optionally substituted 5- or 6-membered heterocyclic group, or a pharmaceutically acceptable salt, enantiomer, stereoisomer, solvate or polymorph thereof.

12. The compound according to claim 11 wherein $R^1$ is H, halogen, CN, $NO_2$, $NH_2$, $NHCH_3$, or a morpholinylethoxy group.

13. The compound according to claim 11 wherein $R^1$ and R' are each independently H or a halogen.

14. The compound according to claim 13 wherein $R^1$ is Cl or F and R' is H.

15. The compound according to claim 11 wherein $R^3$ is H, a halogen or CN.

16. The compound according to claim 11 wherein X' and Y' are both O, j, $j_1$ and $n_1$ are each 0 and n is 1 or 2.

17. The compound according to claim 11 wherein Rp is a pyrimidine attached at the N-1 position and contains substituent $R^{2a}$, attached at the 5-position of the pyrimidine wherein the $R^{2a}$ is H, $CH_3$, F or Cl.

18. The compound according to claim 11 wherein Rp is a uracil group attached at the N-1 position and contains a substituted $R^{2a}$, attached at the 5-position of the uracil group, wherein the $R^{2a}$ is H or $CH_3$.

19. The compound according to claim 11 wherein the compound according to the chemical structure:

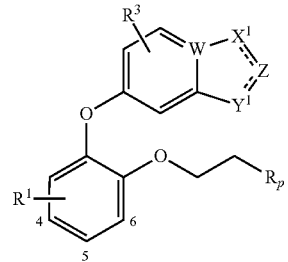

wherein $R^1$ is H, a halogen, CN, $NO_2$, or an optionally substituted alkyl group;

Each $R^2$ is independently H, a $C_1$-$C_3$ alkyl optionally substituted with up to three fluorines, CN or a halogen;

$R^3$ is H, OH, a $C_1$-$C_3$ alkyl group which is optionally substituted with up to 3 halogens, a halogen, $NO_2$ or CN;

Rp is an optionally substituted pyrimidine linked at the 1-position of the pyrimidine optionally substituted at the 5- or 6-position with a substituent $R^{2a}$;

$R^{2a}$ is H, halogen, optionally substituted $C_1$-$C_3$ alkyl, optionally substituted —O—($C_1$-$C_3$) alkyl or CN;

W is N or C;

$X^1$ is

O or N—$R^X$ when W is C, or

when W is N;

Z is

;

Y$^1$ is

O or N—R$^Y$ when W is C, or

when W is N; and

R$^X$ and R$^Y$ are each independently H or a C$_1$-C$_6$ alkyl group, optionally substituted with one or two hydroxyl groups;

or a pharmaceutically acceptable salt, solvate or polymorph thereof.

20. The compound according to claim 19 wherein R$^{2a}$ is H.

21. The compound according to claim 19 wherein R$^1$ is H, a halogen or a CN group.

22. The compound according to claim 19 wherein R$^3$ is H, a halogen or CN.

23. The compound according to claim 19 wherein R$_p$ is a uracil group.

24. The compound according to claim 19 wherein R$_p$ is a uracil group and R$^{2a}$ is H, a halogen or CH$_3$.

25. The compound according to claim 19 wherein W is N.

26. The compound according to claim 19 wherein W is C.

27. The compound according to claim 19 wherein the compound is

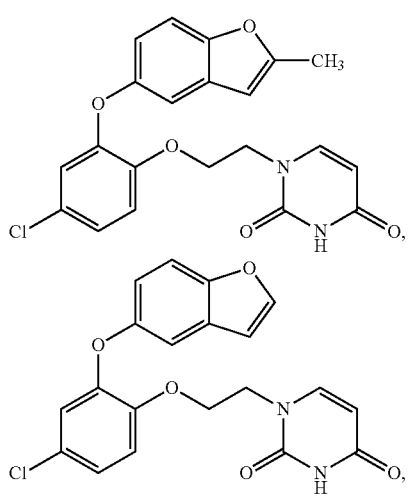

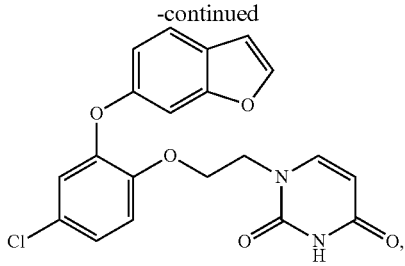

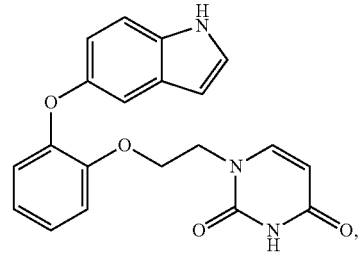

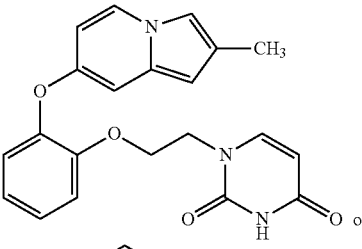

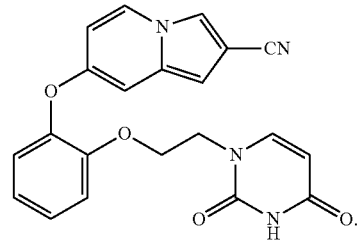

28. A pharmaceutical composition comprising an effective amount of a compound according to claim 1 or claim 11 in combination with a pharmaceutically acceptable carrier, additive or excipient.

29. The composition according to claim 28 wherein said compound is combined with another anti-HIV agent.

30. The composition according to claim 29 wherein said anti-HIV agent is selected from the group consisting of nucleoside reverse transcriptase inhibitors (NRTI), other non-nucleoside reverse transcriptase inhibitors, protease inhibitors, fusion inhibitors and mixtures thereof.

31. The composition according to claim 29 wherein said another anti-HIV agent is selected from the group consisting of 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), a fusion inhibitor and a mixture thereof.

32. The composition according to claim 29 wherein said another anti-HIV agent is nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate 5-chloro-3-(phenylsulfinyl)-2'-indolecarboxamide, U-104489 (PNU-104489), Capravirine (AG-1549, S-1153), atevirdine (U-87201E), aurin tricarboxylic acid (SD-095345), 1-[(6-Cyano-2-indoylyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl) carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea, N-{2-(2,6-Difluorophenethyl]-N'-[2-(5-methylpyridyl)]thiourea, N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl(pypridin-2(1H)-thione, 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38, UC-84 or a mixture thereof.

33. The compound according to claim 19 wherein $R^1$ and $R^3$ are each F, W is N, $R^2$ is H or CN and Rp is an optionally substituted pyrimidine linked at the 1-position of the pyrimidine optionally substituted at the 5- or 6-position with a substituent $R^{2a}$ wherein the $R^{2a}$ is H, F or Cl.

34. The compound according to claim 33 wherein $R^2$ in $X^1$ is H, $R^2$ in Z is CN, $R^2$ in $Y^1$ is H and said pyrimidine is uracil.

35. A pharmaceutical composition comprising an effective amount of a compound according to claim 34 in combination with a pharmaceutically acceptable carrier, additive or excipient.

36. The composition according to claim 35 wherein said compound is combined with another anti-HIV agent.

37. The composition according to claim 36 wherein said anti-HIV agent is selected from the group consisting of nucleoside reverse transcriptase inhibitors (NRTI), other non-nucleoside reverse transcriptase inhibitors, protease inhibitors, fusion inhibitors and mixtures thereof.

38. The composition according to claim 36 wherein said another anti-HIV agent is selected from the group consisting of 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), a fusion inhibitor and a mixture thereof.

39. The composition according to claim 36 wherein said another anti-HIV agent is nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3 (methoxycarbonyl)phenyl)hept-1-enyl)-2-methoxybenzoate, 5-chloro-3-(phenylsulfinyl)-2'-indolecarboxamide, U-104489 (PNU-104489), Capravirine (AG-1549, S-1153), atevirdine (U-87201E), aurin tricarboxylic acid (SD-095345), 1-[(6-Cyano-2-indoylyl)carbonyl]-4-[3-(isopropylamino)-2-pyridinyl]piperazine, 1-[5-RN-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl) carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (14(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea, N-{2-(2,6-Difluorophenethyl]-N'-[2-(5-bromopyridyl)]thiourea, N-{2-(2,6-Difluorophenethyl]-N'-[2-(5-methylpyridyl)]thiourea, N-[2-(3-Fluorofuranyl)ethyl]-N'-[2-(5-chloropyridyl)thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl]-5-ethyl-6-methyl(pypridin-2(1H)-thione, 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38, UC-84 or a mixture thereof.

* * * * *

UNITED STATES PATENT AND TRADEMARK OFFICE
CERTIFICATE OF CORRECTION

PATENT NO. : 9,487,476 B2  
APPLICATION NO. : 14/348952  
DATED : November 8, 2016  
INVENTOR(S) : Jorgensen et al.

Page 1 of 1

It is certified that error appears in the above-identified patent and that said Letters Patent is hereby corrected as shown below:

Column 1, Line 16 to Line 19, the sentence reading:
The subject matter of this application was supported by grant nos. AI044616, GM032136 and GM049551 of the National Institutes of Health. Consequently, the government retains rights in the invention.

Should read:
This invention was made with government support under GM049551, GM032136 and AI044616 awarded by National Institutes of Health. The government has certain rights in the invention.

Signed and Sealed this
Ninth Day of October, 2018

Andrei Iancu
*Director of the United States Patent and Trademark Office*